United States Patent
Young et al.

(10) Patent No.: US 7,031,838 B1
(45) Date of Patent: Apr. 18, 2006

(54) SYSTEM AND METHOD FOR A CRADLE-TO-GRAVE SOLUTION FOR INVESTIGATION AND CLEANUP OF HAZARDOUS WASTE IMPACTED PROPERTY AND ENVIRONMENTAL MEDIA

(75) Inventors: Michael Y. Young, Irvine, CA (US); Yeong-Hwa Shih, Irvine, CA (US); Sheng Quan Tan, Aliso Viejo, CA (US)

(73) Assignee: Integrated Environmental Services. Inc., Lake Forest, CA (US)

( * ) Notice: Subject to any disclaimer, the term of this patent is extended or adjusted under 35 U.S.C. 154(b) by 33 days.

(21) Appl. No.: 10/807,237

(22) Filed: Mar. 24, 2004

Related U.S. Application Data

(60) Provisional application No. 60/456,964, filed on Mar. 25, 2003.

(51) Int. Cl.
*G06F 19/00* (2006.01)
*G06Q 50/00* (2006.01)

(52) U.S. Cl. .............................................. 702/2; 702/5
(58) Field of Classification Search ................. 702/2–5
See application file for complete search history.

(56) References Cited

U.S. PATENT DOCUMENTS

| | | |
|---|---|---|
| 4,845,653 A | 7/1989 | Conrad et al. |
| 4,970,682 A | 11/1990 | Beckwith, Jr. et al. |
| 5,010,776 A | 4/1991 | Lucero et al. |
| 5,321,613 A | 6/1994 | Porter et al. |
| 5,553,492 A | 9/1996 | Barrett et al. |
| 5,666,490 A | 9/1997 | Gillings et al. |
| 5,671,381 A | 9/1997 | Strasnick et al. |
| 5,687,093 A | 11/1997 | Long et al. |
| 5,699,244 A | 12/1997 | Clark, Jr. et al. |
| 5,724,255 A * | 3/1998 | Smith et al. ................. 700/266 |
| 5,808,916 A | 9/1998 | Orr et al. |
| 5,978,804 A | 11/1999 | Dietzman |
| 6,012,016 A | 1/2000 | Bilden et al. |
| 6,023,223 A * | 2/2000 | Baxter, Jr. ................... 340/531 |
| 6,083,353 A | 7/2000 | Alexander, Jr. |
| 6,084,510 A * | 7/2000 | Lemelson et al. ...... 340/539.13 |
| 6,219,805 B1 | 4/2001 | Jones et al. |
| 6,223,143 B1 | 4/2001 | Weinstock et al. |

(Continued)

*Primary Examiner*—Donald McElheny, Jr.
(74) *Attorney, Agent, or Firm*—Andrews Kurth LLP

(57) ABSTRACT

A system and method for environmental data management. The system includes an application including a mapping module that a generates an interactive graphical mapping interface of the site, the interactive mapping interface including links to environmental data from a site and related documents, an analysis module that analyzes the environmental data, the environmental data including contaminants of potential concern (COPC) data, a risk assessment module that assesses the human health risks caused by COPCs at the site, and a remediation module that screens remedial technology for cleaning up COPCs.

85 Claims, 49 Drawing Sheets

U.S. PATENT DOCUMENTS

| | | |
|---|---|---|
| 6,229,546 B1 | 5/2001 | Lancaster et al. |
| 6,341,287 B1 | 1/2002 | Sziklai et al. |
| 6,343,290 B1 | 1/2002 | Cossins et al. |
| 6,363,320 B1 | 3/2002 | Chou |
| 6,385,533 B1 | 5/2002 | Halt et al. |
| 6,430,547 B1 | 8/2002 | Busche et al. |
| 6,542,077 B1 | 4/2003 | Joao |
| 6,574,561 B1 * | 6/2003 | Alexander et al. .............. 702/5 |
| 6,735,630 B1 * | 5/2004 | Gelvin et al. ................ 709/224 |
| 6,816,878 B1 * | 11/2004 | Zimmers et al. ............ 709/200 |
| 2001/0027388 A1 * | 10/2001 | Beverina et al. .............. 703/22 |
| 2001/0027389 A1 * | 10/2001 | Beverina et al. .............. 703/22 |
| 2002/0120642 A1 * | 8/2002 | Fetherston .................. 707/500 |
| 2002/0138197 A1 * | 9/2002 | Schramke et al. .......... 701/213 |
| 2002/0188522 A1 * | 12/2002 | McCall et al. ................ 705/26 |
| 2004/0103431 A1 * | 5/2004 | Davenport et al. ........... 725/33 |

* cited by examiner

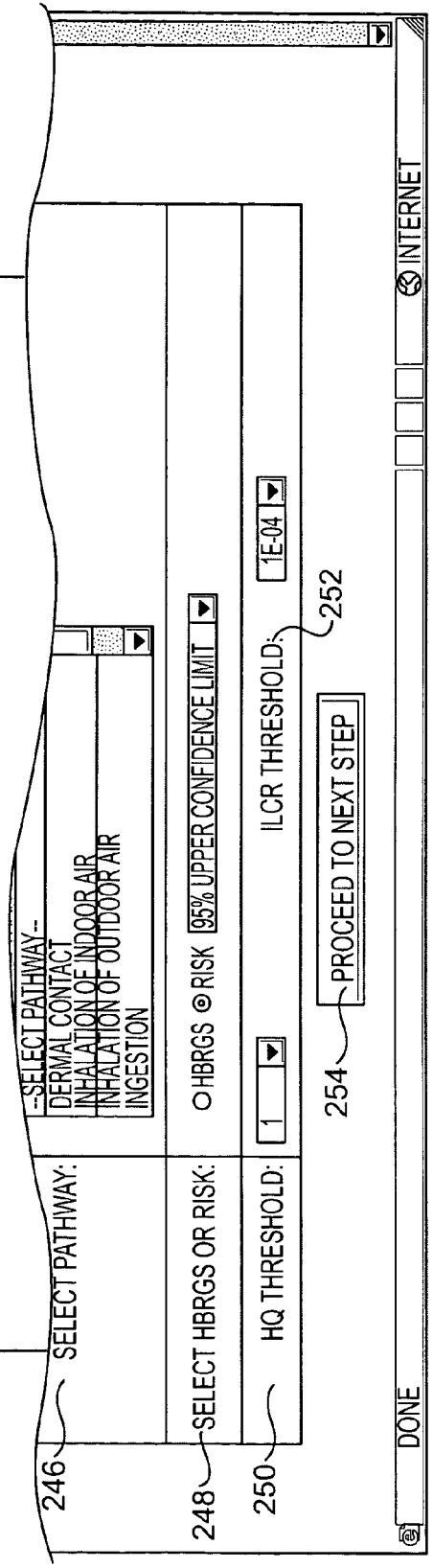

RECEPTORS PARAMETERS - MICROSOFT INTERNET EXPLORER

FILE EDIT VIEW FAVORITES TOOLS HELP     LINKS >>

PLEASE REVIEW THE RECEPTOR PARAMETERS BASED ON THE CONDITION YOU HAVE JUST SELECTED.

RECEPTOR PARAMETERS

| RECEPTOR | EFD | EFINH | EFING | EDC | EDN | BW | IR | AF | SA | ETIN |
|---|---|---|---|---|---|---|---|---|---|---|
| COMMERCIAL WORKER | 0 | 250 | 250 | 70 | 25 | 70 | 1.25 | 1 | 5800 | 8 |
| CONSTRUCTION WORKER | 250 | 250 | 250 | 70 | 1 | 70 | 1.5 | 1 | 3760 | 0 |
| RESIDENTIAL ADULT | 400 | 350 | 350 | 70 | 30 | 70 | 0.83 | 1 | 5860 | 16 |

[RETURN TO PREVIOUS STEP]  [MAKE CHANGES]  [CONTINUE]

NOTES:
EFD: EXPOSURE FREQUENCY DERMAL (DAYS/YEAR)
EFINH: EXPOSURE FREQUENCY INHALATION (DAYS/YEAR)
EFING: EXPOSURE FREQUENCY INGESTION (DAYS/YEAR)
EDC: EXPOSURE DURATION FOR CARCINOGENS (YEARS)
EDN: EXPOSURE DURATION FOR NON-CARCINOGENS (YEARS)
BW: BODY WEIGHT (kg)
IR: INHALATION RATE (INDOOR/OUTDOOR AIR) (m^3/HOUR)
IRS: INGESTION RATE OF SOIL (mg/DAY)
AF: SOIL TO SKIN ADHERENCE FACTOR (mg/cm^2)
SA: SKIN SURFACE AREA (cm^2)
ETOUT: EXPOSURE TIME OUTDOORS (HOURS/DAY)
ETIN: EXPOSURE TIME INDOORS (HOURS/DAY)

FIG. 13b

RECEPTOR PARAMETERS

PLEASE TYPE OVER THE RECEPTOR PARAMETER THAT YOU WOULD LIKE TO CHANGE.

| RECEPTOR | EFD | EFING | EDC | EDN | BW | IR | AF | SA | ETIN |
|---|---|---|---|---|---|---|---|---|---|
| COMMERCIAL WORKER | 0 | 250 | 70 | 25 | 70 | 1.25 | 1 | 5800 | 8 |
| CONSTRUCTION WORKER | 250 | 250 | 70 | 1 | 70 | 1.5 | 1 | 3760 | 0 |
| RESIDENTIAL ADULT | 400 | 350 | 70 | 30 | 70 | 0.83 | 1 | 5800 | 16 |

ACCEPT CHANGES    CANCEL CHANGES

NOTES:
EFD: EXPOSURE FREQUENCY DERMAL (DAYS/YEAR)
EFINH: EXPOSURE FREQUENCY INHALATION (DAYS/YEAR)
EFING: EXPOSURE FREQUENCY INGESTION (DAYS/YEAR)
EDC: EXPOSURE DURATION FOR CARCINOGENS (YEARS)
EDN: EXPOSURE DURATION FOR NON-CARCINOGENS (YEARS)
BW: BODY WEIGHT (kg)
IR: INHALATION RATE (INDOOR/OUTDOOR AIR) (m^3/HOUR)
IRS: INGESTION RATE OF SOIL (mg/DAY)
AF: SOIL TO SKIN ADHERENCE FACTOR (mg/cm^2)
SA: SKIN SURFACE AREA (cm^2)
ETOUT: EXPOSURE TIME OUTDOORS (HOURS/DAY)
ETIN: EXPOSURE TIME INDOORS (HOURS/DAY)

HQ/ILCR REPORT - MICROSOFT INTERNET EXPLORER
FILE EDIT VIEW FAVORITES TOOLS HELP | LINKS >>

HQ/ILCR PRELIMINARY REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/12/2004 8:36:29 PM
RECEPTOR: COMMERCIAL WORKER, CONSTRUCTION WORKER, RESIDENTIAL ADULT
PATHWAY: DERMAL CONTACT, INHALATION OF INDOOR AIR
RISK - CONCENTRATION BASIS: 95% UPPER CONFIDENCE LIMIT - HQ THRESHOLD: 1.E+0 - ILCR THRESHOLD: 1.E-4

| RECEPTOR/PATHWAY | COMPOUND | CONCENT-RATION (mg/kg) | HQ CALCULATION | | | ILCR CALCULATION | | | |
|---|---|---|---|---|---|---|---|---|---|
| | | | CDI (mg/kg*DAY) | RFD (mg/kg*DAY) | HQ (UNITLESS) | CDI (mg/kg*DAY) | CSF (kg*DAY/mg) | ILCR (UNITLESS) |
| RECEPTOR: COMERCIAL WORKER | | | | | | | | | |
| INHALATION OF INDOOR AIR | BENZENE | 1.23E+0 | 1.23E+0 | 1.71E-3 | 6.34E-1 | 9.13E-4 | 1.E-1 | 9.13E-5 | |
| INHALATION OF INDOOR AIR | ETHYL BENZINE | 2.61e+0 | 2.61e+0 | 2.9E-1 | 2.05E-3 | 5.95E-4 | 3.85E-3 | 2.29E-6 | |
| INHALATION OF INDOOR AIR | PHC AS DIESEL FUEL | 4.E+2 | 4.e+2 | NA | NA | NA | NA | NA | |
| INHALATION OF INDOOR AIR | PHC AS GASOLINE | 3.25E-2 | 3.25E-2 | NA | NA | NA | NA | NA | |
| INHALATION OF INDOOR AIR | TETRACHLOROETHYLENE(PCE) | 1.84E-1 | 1.84E-1 | 1.7E-1 | 1.97E-3 | 3.34E-4 | 1.5E-1 | 5.02E-5 | |
| INHALATION OF INDOOR AIR | TOLUENE | 4.22E+0 | 4.22E+0 | 1.1E-1 | 1.37E-2 | 1.51E-3 | NA | NA | |
| INHALATION OF INDOOR AIR | TRICHLOROETHYLENE(TCE) | 1.44E-1 | 1.44E-1 | 1.E-2 | 1.72E-2 | 1.72E-4 | 1.E-2 | 1.72E-6 | |
| INHALATION OF INDOOR AIR | XYLENES, TOTAL | 8.43+0 | 8.43+0 | 2.9E-2 | NA | NA | NA | NA | |
| RECEPTOR: CONSTRUCTION WORKER | | | | | | | | | |
| DERMAL CONTACT | BENZENE | 1.23E+0 | 4.52E-7 | 3.E-3 | 1.61E-4 | 4.6E-7 | 16.6E-2 | 2.49E-8 | |
| DERMAL CONTACT | ETHYL BENZINE | 2.61e+0 | 9.6E-7 | 1.07E-1 | 8.97E-6 | 9.6E-7 | 3.85E-3 | 3.69E-9 | |
| DERMAL CONTACT | PHC AS DIESEL FUEL | 4.E+2 | NA | NA | NA | NA | NA | NA | |
| DERMAL CONTACT | PHC AS GASOLINE | 3.25E-2 | NA | NA | NA | NA | NA | NA | |
| DERMAL CONTACT | TETRACHLOROETHYLENE(PCE) | 1.84E-1 | 6.78E-8 | 1.E-1 | 6.78E-7 | 6.78E-8 | 5.2E-2 | 3.53E-9 | |
| DERMAL CONTACT | TOLUENE | 4.22E+0 | 1.55E-6 | 1.6E+0 | 9.71E-7 | 1.66E-6 | NA | NA | |
| DERMAL CONTACT | TRICHLOROETHYLENE(TCE) | 1.44E-1 | 5.3E-8 | 3.E-4 | 1.77E-4 | 5.3E-8 | 4.E-1 | 2.12E-8 | |

PAGE 1 OF 3

| COMPOUND | CUMULATIVE HQ SUMMARY ||||| CUMULATIVE ILCR SUMMARY |||||
| | INGESTION | DERMAL | OUTDOOR AIR | INDOOR AIR | ALL PATHWAYS | INGESTION | DERMAL | OUTDOOR AIR | INDOOR AIR | ALL PATHWAYS |
|---|---|---|---|---|---|---|---|---|---|---|
| COMMERCIAL WORKER 3020 | | | | | | | | | | |
| BENZENE 3024 | N/A | 1.51E-4 | N/A | 5.34E-1 | 5.34E-1 | N/A | N/A | N/A | 9.13E-5 | 9.13E-5 |
| ETHYLBENZENE | N/A | 8.97E-6 | N/A | 2.05E-3 | 2.05E-3 | N/A | N/A | N/A | 2.28E-8 | 2.28E-8 |
| PHC AS DIESEL FUEL | N/A | N/A | N/A | N/A | N/A | N/A | N/A | N/A | N/A | N/A |
| PHC AS GASOLINE 302 | N/A | N/A | N/A | N/A | N/A | N/A | N/A | N/A | N/A | N/A |
| TETRACHLOROETHYLENE(PCE) | N/A | N/A | N/A | 1.97E-3 | 1.97E-3 | N/A | N/A | N/A | 5.02E-5 | 5.02E-5 |
| TOLUENE | N/A | N/A | N/A | 1.37E-2 | 1.37E-2 | N/A | N/A | N/A | N/A | N/A |
| TRICHLOROETHYLENE(TCE) | N/A | N/A | N/A | 1.72E-2 | 1.72E-2 | N/A | N/A | N/A | 1.72E-8 | 1.72E-8 |
| XYLENES, TOTAL | N/A | N/A | N/A | N/A | N/A | N/A | N/A | N/A | N/A | N/A |
| CUMULATIVE HQ/ILCR | N/A | N/A | N/A | -5.69E-1 | -5.69E-1 | N/A | N/A | N/A | 1.45E-4 | -1.45E-4 |
| COMMERCIAL WORKER | | | | | | | | | | |
| BENZENE | N/A | 1.51E-4 | N/A | N/A | 1.51E-4 | N/A | N/A | N/A | N/A | 2.49E-8 |
| ETHYLBENZENE | N/A | 8.97E-6 | N/A | N/A | 8.97E-6 | N/A | 2.49E-8 | N/A | N/A | 3.69E-9 |
| PHC AS DIESEL FUEL | N/A | N/A | N/A | N/A | N/A | N/A | 3.69E-9 | N/A | N/A | N/A |
| PHC AS GASOLINE | N/A | N/A | N/A | N/A | N/A | N/A | N/A | N/A | N/A | N/A |
| TETRACHLOROETHYLENE(PCE) | N/A | 6.78E-7 | N/A | N/A | 6.78E-7 | N/A | 3.53E-9 | N/A | N/A | 3.53E-9 |

RISK CHARACTERIZATION SUMMARY REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/12/2004 8:36:29 PM
RECEPTOR: COMMERCIAL WORKER, CONSTRUCTION WORKER, RESIDENTIAL ADULT
PATHWAY: DERMAL CONTACT, INHALATION OF INDOOR AIR
RISK - CONCENTRATION BASIS: 95% UPPER CONFIDENCE LIMIT - HQ THRESHOLD: 1.E+0 - ILCR THRESHOLD: 1.E-4

PAGE 1 OF 2

FIG. 13e

TOXICITY VALUES - MICROSOFT INTERNET EXPLORER

FILE EDIT VIEW FAVORITES TOOLS HELP

LINKS >>

TOXICITY VALUES USED REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/12/2004 8:40:14 PM
RECEPTOR: COMMERCIAL WORKER, CONSTRUCTION WORKER, RESIDENTIAL ADULT
PATHWAY: DERMAL CONTACT, INHALATION OF INDOOR AIR
RISK - CONCENTRATION BASIS: 95% UPPER CONFIDENCE LIMIT - HQ THRESHOLD: 1.E+0 - ILCR THRESHOLD: 1.E-4

| RECEPTOR/PATHWAY | COMPOUND | TOXICITY NAME | TOXICITY DESCRIPTION | TOXICITY VALUE |
|---|---|---|---|---|
| COMMERCIAL WORKER | | | | |
| INHALATION OF INDOOR AIR | BENZENE | RfDi | NCEA | 1.71E-3 |
| INHALATION OF INDOOR AIR | BENZENE | SFi | CA | 1.E-1 |
| INHALATION OF INDOOR AIR | ETHYLBENZINE | RfDi | IRIS | 2.9E-1 |
| INHALATION OF INDOOR AIR | ETHYLBENZINE | SFi | HEAST | 3.85E-3 |
| INHALATION OF INDOOR AIR | PHC AS DIESEL FUEL | | | 0.E+0 |
| INHALATION OF INDOOR AIR | PHC AS GASOLINE | | | 0.E+0 |
| INHALATION OF INDOOR AIR | TETRACHLOROETHYLENE(PCE) | RfDi | NCEA | 1.7E-1 |
| INHALATION OF INDOOR AIR | TETRACHLOROETHYLENE(PCE) | SFi | CA | 1.5E-1 |
| INHALATION OF INDOOR AIR | TOLUENE | RfDi | IRIS | 1.1E-1 |
| INHALATION OF INDOOR AIR | TOLUENE | SFi | | 0.E+0 |
| INHALATION OF INDOOR AIR | TRICHLOROETHYLENE(TCE) | RfDi | NCEA | 1.E-2 |
| INHALATION OF INDOOR AIR | TRICHLOROETHYLENE(TCE) | SFi | CA | 1.E-2 |
| INHALATION OF INDOOR AIR | XYLENES, TOTAL | RfDi | IRIS | 2.9E-2 |
| INHALATION OF INDOOR AIR | XYLENES, TOTAL | SFi | | 0.E+0 |
| CONSTRUCTION WORKER | | | | |
| DERMAL CONTACT | BENZENE | SubRfDd | OTHER | 3.E-3 |

PAGE 1 OF 4

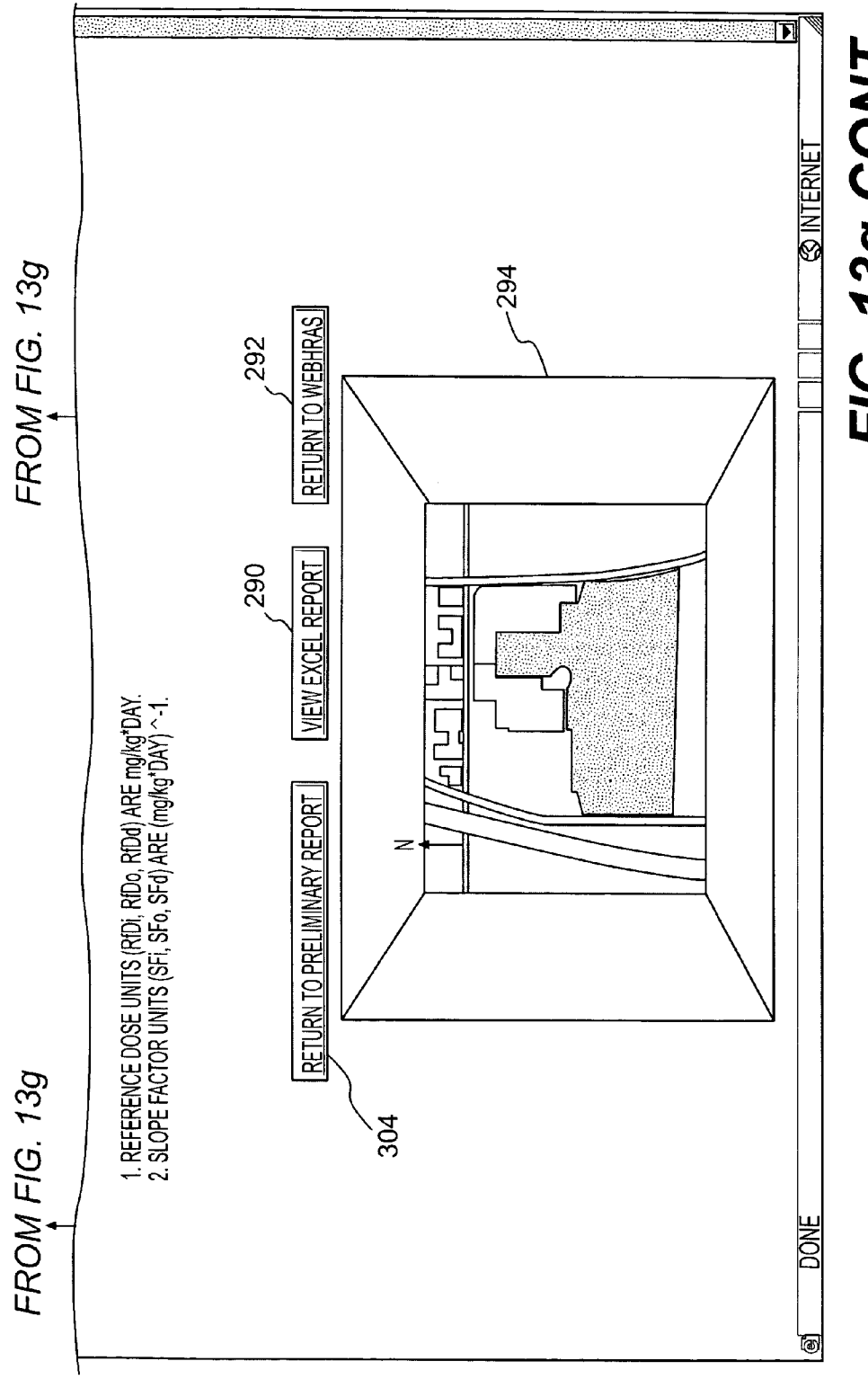

| | A | B | C | D | E | F | G | H | I | J |
|---|---|---|---|---|---|---|---|---|---|---|
| 1 | | HQ/ILCR PRELIMINARY REPORT | | | | | | | | |
| 2 | | SITE NAME : CARSON TOWN CENTER - JOB NAME : SOUTH QUADRANT | | | | | | | | |
| 3 | | ROI NAME : TEST SITE AREA 2 -START DATE : 8/1/1985 12:00:00 PM - END DATE : 7/3/2003 12:0 | | | | | | | | |
| 4 | | MEDIA : SOIL - SOIL TYPE : SILT - REPORT DATE/TIME : 1/12/2004 8:47:46 PM | | | | | | | | |
| 5 | | RECEPTOR : COMMERCIAL WORKER, CONSTRUCTION WORKER, RESIDENTIAL ADULT | | | | | | | | |
| 6 | | PATHWAY : DERMAL CONTACT, INHALATION OF INDOOR AIR | | | | | | | | |
| 7 | | RISK - CONCENTRATION BASIS : 95% UPPER CONFIDENCE LIMIT - HQ THRESHOLD : 1.E+0 - ILCR TH | | | | | | | | |
| 8 | | | | | | | | | | |
| 9 | | | | | | HQ CALCULATION | | ILCR CALCULATION | | |
| 10 | RECEPTOR | PATHWAY | COMPOUND | CONCENTRATION | CDI(mg/kg | RfD(mg/kg | HQ (untitle | CDI(mg/kg | CSF (kg*d | ILCR |
| 11 | COMMERCIAL WORK | INHALATION OF INDOOR | BENZENE | 1.228371028 | 0.000913 | 0.00171 | 0.533737 | 0.000913 | 0.1 | 9.13E |
| 12 | COMMERCIAL WORK | INHALATION OF INDOOR | ETHYLBENZENE | 2.608454599 | 0.000595 | 0.29 | 0.00205 | 0.000595 | 0.00385 | 2.29E |
| 13 | COMMERCIAL WORK | INHALATION OF INDOOR | PHC AS DIESEL FU | 399.9914476 | | | | | | |
| 14 | COMMERCIAL WORK | INHALATION OF INDOOR | PHC AS GASOLINE | 325.1535332 | | | | | | |
| 15 | COMMERCIAL WORK | INHALATION OF INDOOR | TETRACHLOROETH | 0.18427058 | 0.0000334 | 0.17 | 0.001967 | 0.000334 | 0.15 | 5.02E |
| 16 | COMMERCIAL WORK | INHALATION OF INDOOR | TOLUENE | 4.221836238 | 0.001507 | 0.11 | 0.013697 | 0.001507 | | |
| 17 | COMMERCIAL WORK | INHALATION OF INDOOR | TRICHLOROETHYLE | 0.144122158 | 0.000172 | 0.01 | 0.017152 | 0.000172 | 0.01 | 1.72E |

| | | | | | | | |
|---|---|---|---|---|---|---|---|
| 20 | COMMERCIAL WORK | INHALATION OF INDOOR | XYLENES, TOTAL | 8.429169314 | | 0.029 | |
| 21 | CONSTRUCTION WORK | DERMAL CONTACT | BENZENE | 1.228371028 | 4.52E-07 | 0.003 | 0.000151 | 4.52E-07 | 0.055 | 2.49E |
| 22 | CONSTRUCTION WORK | DERMAL CONTACT | ETHYLBENZENE | 2.608454599 | 9.6E-07 | 0.107 | 8.97 E-06 | 9.6E-07 | 0.00385 | 3.69E |
| 23 | CONSTRUCTION WORK | DERMAL CONTACT | PHC AS DIESEL FU | 399.9914476 | | | | | | |
| 24 | CONSTRUCTION WORK | DERMAL CONTACT | PHC AS GASOLINE | 325.1535332 | | | | | | |

CONT. FROM FIG 13h

CONT. FROM FIG 13h

Risk Assessment - Microsoft Internet Explorer webHRAS

SITE NAME: CARSON TOWN CENTER
JOB NAME: SOUTH QUADRANT
ROI NAME: TEST SITE AREA 2 — START DATE: 8/1/1985 - END DATE: 7/3/2003 - REMARK
SELECT JUST ONE MEDIA ONLY.
SELECT MEDIA: SOIL — SI-SILT

○ MANUALLY SELECT ⦿ ALL DETECTED COPCs ○ MAX CONC>IND PRGs ○ MAX CONC.> MCL
YOU WILL NOT BE ABLE TO CHANGE THE SELECTED COPC LIST WITH THIS OPTION

SELECT COMPOUND:
--SELECT COMPOUND--
BENZENE
ETHYLBENZENE
PHCAS:DIESEL-FUEL
PHCAS:GASOLINE

TOXICITY: ○ FEDERAL ⦿ STATE CALIFORNIA

SELECT RECEPTOR: TO SELECT MORE THAN ONE RECEPTOR, HOLD DOWN THE CTRL KEY WHILE MAKING SELECTIONS
--SELECT RECEPTOR--
COMMERCIAL WORKER
RESIDENTIAL CHILD
CONSTRUCTION WORKER
RESIDENTIAL ADULT

SELECT PATHWAY: TO SELECT MORE THAN ONE PATHWAY, HOLD DOWN THE CTRL KEY WHILE MAKING SELECTIONS
--SELECT PATHWAY--
DERMAL CONTACT
INHALATION OF INDOOR AIR
INHALATION OF OUTDOOR AIR
INGESTION

SELECT HBRGs OR RISK: ⦿ HBRGs ○ RISK
HQ THRESHOLD: 1    ILCR THRESHOLD: 1E-04    PROCEED TO NEXT STEP

HQ/ILCR PRELIMINARY REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/29/2004 4:31:23 PM
RECEPTOR: COMMERCIAL WORKER, RESIDENTIAL CHILD
PATHWAY: DERMAL CONTACT, INHALATION OF INDOOR AIR
HBRG - CONCENTRATION BASIS: UNITY - HQ THRESHOLD: 1.E+0 - ILCR THRESHOLD: 1.E-4

| RECEPTOR/PATHWAY | COMPOUND | CONCENT-RATION (mg/kg) | HQ CALCULATION | | | | ILCR CALCULATION | | |
|---|---|---|---|---|---|---|---|---|---|
| | | | CDI (mg/kg*DAY) | RfD (mg/kg*DAY) | HQ (UNITLESS) | | CDI (mg/kg*DAY) | CSF (kg*DAY/mg) | ILCR (UNITLESS) |
| RECEPTOR: COMMERCIAL WORKER | | | | | | | | | |
| INHALATION OF INDOOR AIR | BENZENE | 1.E+0 | 7.52E-4 | 1.71E+3 | 4.4E+1 | | 7.62E-4 | 1.E+1 | 7.62E-6 |
| INHALATION OF INDOOR AIR | ETHYL BENZENE | 1.E+0 | 2.67E-4 | 2.9E+1 | 9.2E+4 | | 2.67E-4 | 3.85E+3 | 1.03E-5 |
| INHALATION OF INDOOR AIR | PHC AS DIESEL FUEL | 1.E+0 | NA | NA | NA | | NA | NA | NA |
| INHALATION OF INDOOR AIR | PHC AS GASOLINE | 1.E+0 | NA | NA | NA | | NA | NA | NA |
| INHALATION OF INDOOR AIR | TETRACHLOROETHYLENE(PCE) | 1.E+0 | 1.16E-3 | 1.7E+1 | 6.81E-3 | | 1.16E+3 | 1.5E+1 | 1.74E-4 |
| INHALATION OF INDOOR AIR | TOLUENE | 1.E+0 | 4.01E-4 | 1.1E+1 | 3.64E-3 | | 4.01E-4 | NA | NA |
| INHALATION OF INDOOR AIR | TRICHLOROETHYLENE(TCE) | 1.E+0 | 6.61E-4 | 1.E-2 | 6.61E+2 | | 6.61E-4 | 1.E+2 | 6.61E-6 |
| INHALATION OF INDOOR AIR | XYLENES, TOTAL | 1.E+0 | NA | 2.9E-2 | NA | | NA | NA | NA |
| RECEPTOR: RESIDENTIAL CHILD | | | | | | | | | |
| DERMAL CONTACT | BENZENE | 1.E+0 | 1.28E-6 | 3.E-3 | 4.26-4 | | 1.28E-6 | 5.67E+2 | 7.25E-8 |
| DERMAL CONTACT | ETHYL BENZINE | 1.E+0 | NA | 9.7E+2 | 1.32E+5 | | NA | 3.85E+3 | 4.92E+9 |
| DERMAL CONTACT | PHC AS DIESEL FUEL | 1.E+0 | NA | NA | NA | | NA | NA | NA |
| DERMAL CONTACT | PHC AS GASOLINE | 1.E+0 | NA | NA | NA | | NA | NA | NA |
| DERMAL CONTACT | TETRACHLOROETHYLENE(PCE) | 1.E+0 | 1.28E-6 | 1.E-2 | 1.28E-4 | | 1.28E-6 | 5.2E+2 | 6.65E-8 |
| DERMAL CONTACT | TOLUENE | 1.E+0 | 1.28E-6 | 1.55E+1 | 7.99E-6 | | 1.28E-6 | NA | NA |
| DERMAL CONTACT | TRICHLOROETHYLENE(TCE) | 1.E+0 | 1.28E-6 | 9.E-4 | 1.42E-3 | | 1.28E-6 | 7.33E+2 | 9.37E-8 |

PAGE 1 OF 2

FIG. 14b

SUMMARY REPORT - MICROSOFT INTERNET EXPLORER

HBRG SUMMARY REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/29/2004 4:36:41 PM
RECEPTOR: COMMERCIAL WORKER, RESIDENTIAL CHILD
PATHWAY: DERMAL CONTACT, INHALATION OF INDOOR AIR
HBRG - CONCENTRATION BASIS: UNITY - HQ THRESHOLD: 1.E+0 - ILCR THRESHOLD: 1.E-4

| COMPOUND | THEORETICAL SCALED CONCENTRATION (HQ-BASED) HBRG (mg/kg) | | | | | THEORETICAL SCALED CONCENTRATION (ILCR-BASED) HBRG (mg/kg) | | | | |
|---|---|---|---|---|---|---|---|---|---|---|
| | INGESTION | DERMAL | OUTDOOR AIR | INDOOR AIR | ALL PATHWAYS | INGESTION | DERMAL | OUTDOOR AIR | INDOOR AIR | ALL PATHWAYS |
| COMMERCIAL WORKER | | | | | | | | | | |
| BENZENE | NA | NA | NA | 2.27E+0 | 2.27E+0 | NA | NA | NA | 1.33E+0 | 1.33E+0 |
| ETHYL BENZENE | NA | 2.35E+3 | NA | 1.09E+3 | 1.09E+3 | NA | NA | NA | 9.74E+1 | 9.74E+1 |
| PHC AS DIESEL FUEL | NA | 7.59E+4 | NA | NA | NA | NA | NA | NA | NA | NA |
| PHC AS GASOLINE | NA | NA | NA | NA | NA | NA | NA | NA | NA | NA |
| TETRACHLOROETHYLENE(PCE) | NA | NA | NA | 1.47E+2 | 1.47E+2 | NA | NA | NA | 5.76E+1 | 5.76E+1 |
| TOLUENE | NA | NA | NA | 2.74E+2 | 2.74E+2 | NA | NA | NA | NA | NA |
| TRICHLOROETHYLENE(TCE) | NA | NA | NA | 1.51E+1 | 1.51E+1 | NA | NA | 1.38E+3 | 1.51E+1 | 1.51E+1 |
| XYLENES, TOTAL | NA | 7.82E+3 | NA | NA | NA | NA | NA | 2.03E+4 | NA | NA |
| RESIDENTIAL CHILD | | | | | | | | | | |
| BENZENE | NA | NA | NA | 3.62E+1 | 3.62E+1 | NA | NA | NA | 2.12E+1 | 2.12E+1 |
| ETHYL BENZENE | NA | NA | NA | 1.73E+2 | 1.73E+2 | NA | NA | NA | 1.55E+1 | 1.55E+1 |
| PHC AS DIESEL FUEL | NA | NA | NA | NA | NA | NA | NA | NA | NA | NA |
| PHC AS GASOLINE | NA | NA | NA | NA | NA | NA | NA | 1.5E+3 | NA | NA |
| TETRACHLOROETHYLENE(PCE) | NA | NA | NA | 2.34E+1 | 2.34E+1 | NA | NA | NA | 9.18E+2 | 9.18E-2 |

PAGE 1 OF 2

FIG. 14c

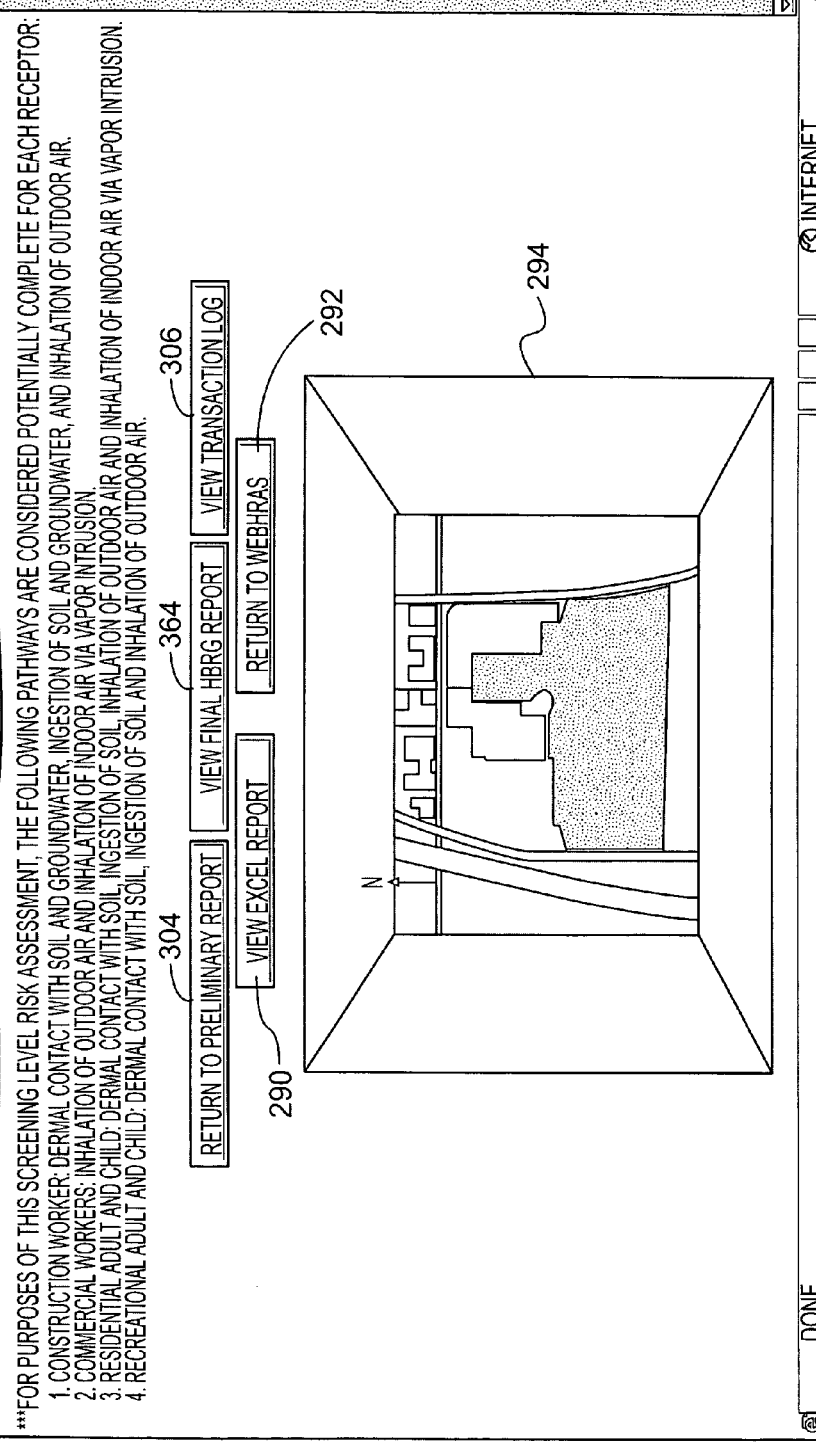

FINAL HBRG REPORT
SITE NAME: CARSON TOWN CENTER - JOB NAME: SOUTH QUADRANT
ROI NAME: TEST SITE AREA 2 - START DATE: 8/1/1985 12:00:00 PM - END DATE: 7/3/2003 12:00:00 PM
MEDIA: SOIL - SOIL TYPE: SILT - REPORT DATE/TIME: 1/29/2004 4:45:50 PM
RECEPTOR: COMMERCIAL WORKER, RESIDENTIAL CHILD
PATHWAY: DERMAL CONTACT, INHALATION OF INDOOR AIR
HBRG - CONCENTRATION BASIS: UNITY - HQ THRESHOLD: 1.E+0 - ILCR THRESHOLD: 1.E-4

| COMPOUND | INITIAL HBRG (mg/kg) | SATURATION | FINAL HBRG (mg/kg) |
|---|---|---|---|
| COMMERCIAL WORKER | | | |
| BENZENE | 1.35E+0 | 2.45E+3 | 1.35E+0 |
| ETHYL BENZINE | 9.74E+1 | 1.27E+3 | 9.74E+1 |
| PHC AS DIESEL FUEL | -1.E+0 | 3.91E+3 | -1.E+0 |
| PHC AS GASOLINE | -1.E+0 | 3.91E+3 | -1.E+0 |
| TETRACHLOROETHYLENE(PCE) | 5.76E-1 | 6.73E+2 | 5.76E-1 |
| TOLUENE | 2.74E+2 | 2.03E+3 | 2.74E+2 |
| TRICHLOROETHYLENE(TCE) | 1.51E+1 | 3.91E+3 | 1.51E+1 |
| XYLENES, TOTAL | 1.E+0 | | 1.E+0 |
| RESIDENTIAL CHILD | | | |
| BENZENE | 2.12E-1 | 2.45E+3 | 2.12E-1 |
| ETHYL BENZINE | 1.55E+1 | 1.27E+3 | 1.55E+1 |
| PHC AS DIESEL FUEL | -1.E+0 | 3.91E+3 | -1.E+0 |
| PHC AS GASOLINE | -1.E+0 | 3.91E+3 | -1.E+0 |
| TETRACHLOROETHYLENE(PCE) | 9.18E-2 | 6.73E+2 | 9.18E-2 |
| TOLUENE | 4.38E+1 | 2.03E+3 | 4.38E+1 |
| TETRACHLOROETHYLENE(PCE) | 2.41E+0 | 3.91E+3 | 2.41E+0 |

PAGE 1 OF 2

*FIG. 14d*

INITIAL REMEDIAL TECHNOLOGY SCREENING RESULTS *

SELECTION OF APPLICABLE REMEDIAL TECHNOLOGY AND RANKING IS DEFINED USING BASIC SITE KNOWLEDGE: MEDIA, CONTAMINANT TYPE AND CONTAMINANT (95% UCL)

REGION OF INTEREST (ROI): TEST SITE AREA 2
CONTAMINATION PLUME ID: 66
MEDIA: SOIL
CONTAMINANT TYPE: FUELS, HALOGENATED VOCs
DATA/TIME OF SCREENING RUN: JAN 13 2004 10:58AM
DATA RANGE OF DATA USED FOR SCREENING: 08/01/1985 TO 07/03/2003

| APPLICABLE REMEDIAL TECHNOLOGY | RANKING ** | PARAMETERS REQUIRED TO CONDUCT COMPREHENSIVE REMEDIAL TECHNOLOGY SCREENING |
|---|---|---|
| 4.1 IN-SITU SOIL VAPOR EXTRACTION | 2.0 | THICKNESS OF UNSATURATED ZONE, DEPTH OF CONTAMINATION BELOW GROUND SURFACE, DEPTH TO SATURATED ZONE, VOLUME EXTENT OF CONTAMINATION, SOIL BULK DENSITY, WATER FILLED POROSITY, AIR FILLED POROSITY, SOIL-WATER PARTITION COEFFICIENT FOR CONTAMINANT, HERRY'S LAW CONSTANT FOR CONTAMINANT, VAPOR PERMEABILITY FOR UNSATURATED ZONE |
| 4.6 IN-SITU BIOVENTING | 2.0 | DEPTH OF CONTAMINATION BELOW GROUND SURFACE, THICKNESS EXTENT OF CONTAMINATION (Z-DIRECTION), TEMPERATURE OF MEDIA pH DEGRADATION RATE CONSTANT FOR CONTAMINANT |
| 4.7 IN-SITU ENHANCED BIOREMEDIATION | 2.0 | TEMPERATURE OF MEDIA pH DEGRADATION RATE CONSTANT FOR CONTAMINANT |
| 4.8 IN-SITU NATURAL ATTENUATION | 2.0 | TEMPERATURE OF MEDIA pH DEGRADATION RATE CONSTANT FOR CONTAMINANT |
| 4.10 CONTAINMENT CAPPING | 2.0 | SURFACE AREA EXTENT OF CONTAMINATION, DEPTH OF CONTAMINATION BELOW GROUND SURFACE, THICKNESS EXTENT OF CONTAMINATION (Z-DIRECTION), DEPTH TO SATURATED ZONE |
| 5.1 EX-SITU SOIL VAPOR EXTRACTION | 2.0 | POROSITY, SOIL-WATER PARTION VOLUME EXTENT OF CONTAMINATION, SOIL BULK DENSITY, WATER FILLED POROSITY, AIR FILLED COEFFICIENT FOR CONTAMINANT, HERRY'S LAW CONSTANT FOR CONTAMINANT |

FROM FIG16b →

FROM FIG16b →

| | | |
|---|---|---|
| 5.6 EX-SITU INCINERATION | 2.0 | VOLUME EXTENT OF CONTAMINATION |
| 5.7 EX-SITU THERMAL DESORPTION | 2.0 | VOLUME EXTENT OF CONTAMINATION |
| 4.6 IN-SITU THERMALLY ENHANCED SOIL VAPOR EXTRACTION | 2.0 | THICKNESS OF UNSATURATED ZONE, DEPTH OF CONTAMINATION, BELOW GROUND SURFACE. DEPTH TO SATURATED ZONE. VOLUME EXTENT OF CONTAMINATION, SOIL BULK DENSITY, MOISTURE CONTENT AIR FILLED POROSITY, SOIL-WATER PARTITION COEFFICIENT FOR CONTAMINANT, HERRY'S LAW CONSTANT FOR CONTAMINATION, VAPOR PERMEABILITY FOR SATURATED ZONE |
| 4.9 IN-SITU PHYTOREMDIATION | 1.7 | THICKNESS EXTENT OF CONTAMINATION (Z-DIRECTION), DEPTH OF CONTAMINATION BELOW GROUND SURFACE, SOIL BULK DENSITY, SOIL-WATER PARTITION COEFFICIENT FOR CONTAMINANT, OCTANOL WATER PARTITION COEFFICIENT FOR CONTAMINANT |
| 5.2 EX-SITU SOIL WASHING | 1.7 | VOLUME EXTENT OF CONTAMINATION, SOIL BULK DENSITY |
| 5.9 EX-SITU BIOPILES | 1.7 | VOLUME EXLENT OF CONTAMINATION, DEGRADATION RATE CONSTANT FOR CONTAMINANT |

FIG.16b CONT.

COMPREHENSIVE REMEDIAL TECHNOLOGY SCREENING RESULTS *

SELECTION OF APPLICABLE REMEDIAL TECHNOLOGY AND RANKING IS DEFINED USING DETAILED SITE KNOWLEDGE:
SITE-SPECIFIC, CHEMICAL AND GEOPHYSICAL PARAMETERS

REGION OF INTEREST (ROI): TEST SITE AREA 2
CONTAMINATION PLUME ID: 66
MEDIA: SOIL
CONTAMINANT TYPE: FUELS HALOGENATED VOCs

DATE/TIME OF SCREENING RUN: JAN 13 2004 10:58AM
DATA RANGE OF DATA USED FOR SCREENING: 08/01/1995 TO 07/03/2003

| APPLICABLE REMEDIAL TECHNOLOGY | RANKING ** | IS THE REMEDIAL TECHNOLOGY CAPABLE OF ACHIEVING REMEDIAL OBJECTIVE FOR EACH CONTAMINANT TYPE** | ROUGH ORDER OF MAGNITUDE TIME ESTIMATE (YEARS)*** |
|---|---|---|---|
| 4.10 CONTAINMENT CAPPING | 2.0 | NO (BENZENE, THRICHLOROETHYLENE (ICE)) | 0.4 |
| 4.1 IN-SITU SOIL VAPOR EXTRACTION | 2.0 | YES | 22.8 |
| 4.6 IN-SITU BIOVENTING | 2.0 | YES | N/A |
| 4.7 IN-SITU ENHANCED BIOREMEDIATION | 2.0 | YES | N/A |
| 4.8 IN-SITU NATURAL ATTENUATION | 2.0 | YES | N/A |
| 5.1 EX-SITU SOIL VAPOR EXTRACTION | 2.0 | YES | 0.1 |
| 5.6 EX-SITU INCINERATION | 2.0 | YES | 7.1 |
| 5.7 EX-SITU THERMAL DESORPTION | 2.0 | YES | 18.3 |

FROM FIG16c

| | | |
|---|---|---|
| 4.5 IN-SITU THERMALLY ENHANCED SOIL VAPOR EXTRACTION | 1.7 | YES | 8.6 |
| 5.2 EX-SITU SOIL WASHING | 1.7 | YES | 15.7 |
| 5.9 EX-SITU BIOPILES | 1.7 | YES | 1.1 |

\* ALGORITHM IS BASED ON GUIDENCE FROM THE FRTR REMEDIATION TECHNOLOGIES SCREENING MATRIX AND REFERENCE GUIDE, VERSION 4.0 (JAN 2002)
\*\* RANKING RANGE IS FROM 2.0 (MOST APPLICABLE) TO 0.0 (LEAST APPLICABLE)
\*\*\* BASED ON IDEAL EFFICIENCY FACTORS. CHEMICAL FOR WHICH THE REMEDIATION OBJECTIVE IS NOT ACHIEVED ARE LISTED IN PARENTHESIS
\*\*\*\* REMEDIAL TIME ESTIMATES BASED ON EQUATIONS PRESENTED IN PUBLIC DOMAIN LITERATURE (E.G. GWRTAC, USEPA, FRTR, ITRC AND AFCEE)

GWRTAC- GROUND WATER REMEDIATION TECHNOLOGIES ANALYSIS CENTER
USEPA- UNITED STATES ENVIRONMENTAL PROTECTION AGENCY
FRTR- FEDERAL REMEDIATION TECHNOLOGIES ROUNDTABLE

FIG.16c CONT.

COMPREHENSIVE REMEDIAL TECHNOLOGY SCREENING RESULTS

REGION OF INTEREST (ROI): TEST SITE AREA 2
TIME INTERVAL: FROM 8/1/1985 12:00:00 PM TO 7/3/2003 12:00:00 PM
USERNAME: SQT
ROI CREATED DATE: JAN 13 2004 10:58 AM
PLUME ID: 66
MEDIA: SOIL
IMPACT AREA: 54173.324 M2
IMPACT VOLUME: 310025.1 M3
CONTAMINANT TYPE: FUELS, HALOGENATED VOCs

| APPLICABLE REMEDIAL TECHNOLOGY | RANKING (2-0) | TECHNOLOGY LIMITATIONS | ROUGH ORDER OF MAGNITUDE TIME ESTIMATE (YEARS) | UNIT PRICE | | UNIT | | COST ESTIMATE (UNIT PRICE * IMPACT VOLUME) |
|---|---|---|---|---|---|---|---|---|
| 4.10 CONTAINMENT CAPPING | 2.0 | NO (BENZENE, TRICHLORO ETHYLENE (TCE)) | 0.4 | 35.50 | | M2 ▶ | = | $1,923,153 |
| 4.1 IN-SITU SOIL VAPOR EXTRACTION | 2.0 | YES | 22.8 | | | M3 ▶ | = | |
| 4.6 IN-SITU BIOVENTING | 2.0 | YES | N/A | | | M3 ▶ | = | |
| 4.7 IN-SITU ENHANCED BIOREMEDIATION | 2.0 | YES | N/A | | | M3 ▶ | = | |
| 4.8 IN-SITU NATURAL ATTENUATION | 2.0 | YES | N/A | | | M3 ▶ | = | |
| 5.1 EX-SITU SOIL VAPOR EXTRACTION | 2.0 | YES | 0.1 | 150.25 | | M3 ▶ | = | $46,581,271 |
| 5.6 EX-SITU INCINERATION | 2.0 | YES | 7.1 | | | M3 ▶ | = | |
| 5.7 EX-SITU THERMAL DESORPTION | 2.0 | YES | 18.3 | | | M3 ▶ | = | |
| 4.5 IN-SITU THERMALLY ENHANCED SOIL VAPOR EXTRACTION | 1.7 | YES | 8.6 | | | M3 ▶ | = | |
| 5.2 EX-SITU SOIL WASHING | 1.7 | YES | 15.7 | | | M3 ▶ | = | |
| 5.9 EX-SITU BIOPILES | 1.7 | YES | 1.1 | | | M3 ▶ | = | |

REGION OF INTEREST (ROI) INFORMATION

REGION OF INTEREST (ROI): TEST SITE AREA 2
TIME INTERVAL: FROM 8/1/1985 12:00:00 PM TO 7/3/2003 12:00:00 PM
USERNAME: SQT
ROI CREATED DATE: JAN 13 2004 10:58 AM
REMARK:
MEDIA TYPE: SOIL

REGION OF INTEREST (ROI) REPORTS

INITIAL SCREENING PDF FILE (NON-NAPL)
INITIAL SCREENING LOG FILE (NON-NAPL)
COMPREHENSIVE SCREENING PDF FILE (NON-NAPL)
COMPREHENSIVE SCREENING LOG FILE (NON-NAPL)

SYSTEM AND METHOD FOR A CRADLE-TO-GRAVE SOLUTION FOR INVESTIGATION AND CLEANUP OF HAZARDOUS WASTE IMPACTED PROPERTY AND ENVIRONMENTAL MEDIA

CROSS REFERENCE TO RELATED APPLICATION(S)

This application claims priority of provisional application No. 60/456,964, filed Mar.25, 2003, entitled "SYSTEM AND METHOD FOR A CRADLE-TO-GRAVE SOLUTION FOR THE INVESTIGATION AND CLEANUP OF HAZARDOUS WASTE IMPACTED PROPERTY/MEDIA," of which the subject matter is herein incorporated by reference in its entirety.

BACKGROUND

Since the 1970's, the United States has passed numerous federal and state laws stipulating elaborate and often costly processes for the study and cleanup of environmental media (soil, surface water, groundwater, and/or air) impaired by hazardous chemicals. These processes often become large and complex.

Due to prolonged periods of site investigation and cleanup which generally coincide with changes of personnel in the property owner's organization, project consultants, and regulatory agencies, many hard-earned site studies, environmental data and/or reports are partial, fragmented and at times redundant in scope, paper bound, and not available to the entire project team. Moreover, these data and documents very often are in various forms (text, spreadsheets, drawings, photos, etc) and stored in multiple databases, in different formats, with different versions and usually without any standards. Prior to the present system, software applications that perform discrete sets of functions have been developed separately in the market. However, site data has to be specially processed in order to meet input requirements of each of these applications. These separate applications are not compatible and therefore cannot be integrated to provide users with a thorough assessment of the entire site.

The above-stated situations render the environmental data, that cost millions of dollars to collect, of little value to the property owners. Using existing applications, property owners cannot use the environmental data to their full advantage. The inaccessibility of project data, the lack of a centralized project data/information repository system, and the inability to identify impediments to site closure commonly forces the responsible parties to spend more money than should be necessary in the remedial investigation and site cleanup. This in turn hinders the overall project goals and delays site closure. Ultimately, these factors slow down the progress of cleaning up hazardous waste contaminated sites at both the state and national levels.

Until the below described embodiments, there has been no all-in-one application, web-based or desktop, capable of performing Query, Analysis, Data Visualization, Health Risk Assessment, Remediation Technology Screening and Remediation Cost Estimation sequentially or concurrently using a single uniform database.

SUMMARY

A system and method for environmental data management are described herein. The system and method overcome disadvantages of the prior art. Advantages include providing a fully integrated computer software system application that offers a cradle-to-grave solution to the remedial investigation/feasibility study (RI/FS) and cleanup of hazardous waste impacted property: from the storing, organizing and retrieving of environmental data to estimating costs of the applicable and appropriate remediation technologies for site cleanup.

An additional advantage of certain embodiments is that the RI/FS process can be performed over the Internet and provide real time information to project personnel who reside in different geographical areas. Advantages further include allowing users to enjoy the full and continuing benefits of their investment spent on data collection and assisting responsible parties in effectively managing their project information, data and documents during the investigation and cleanup of hazardous waste contaminated sites. Other advantages include allowing users to understand otherwise complicated site conditions, define regulatory agency acceptable end-state of the project site, identify impediments to site closure, strategize the best course of action, and execute projects efficiently and effectively.

The embodiments described are effective in allowing users to query and analyze data by medium, region of interest (ROI) and time frame (i.e., spatially and temporally) on-the-fly. They provide an all-in-one, easy to work with solution to identify hotspots and foresee remedial results. Moreover, the embodiments allow solutions that fail to be reversed to reveal the source of the failure. Therefore, embodiments enable users to evaluate remedial alternatives and see and plan their remedial strategy before expensive field operations begin, among other features.

Certain embodiments are in response to the need for a web-based all-in-one project data management tool that has the advantage of providing the following capabilities real time:

i) Storing, retrieving, displaying, and sharing project information from a central location in real time among project team members, regulatory communities, and other stakeholders who are geographically dispersed across the globe using the Internet;

ii) Querying site features, analyzing project data and providing real time charts and graphs for easy understanding and formulation or development of general consensus;

iii) Allowing users to query, analyze and display project data by sampling time period both in its entirety and by specific areas of the site with any shapes;

iv) Allowing users to view and analyze site features in three-dimensions to gain common understanding of site conditions, and to identify impediments to site closure and offer a menu of workable solutions;

v) Calculating remedial goals and performing human health risk and ecological risk assessments of any user-defined site land-use conditions resulting from site chemical contamination; and vi) Enabling users to estimate potential health risks associated with the site before expensive field operations, to compare pros and cons of remedial alternatives and to streamline the process of identifying the acceptable end state of the site so that the most appropriate remedial technology to cleanup a property in a cost effective and timely manner can be identified.

The system and method collect, store, and organize information of a project site. Information collected is streamlined to a standardized format that is applicable and immediately useable without reprocessing by the various modules of the system. A standardized data format empowers users with quick implementation and use of project data resulting in greater efficiency and productivity in data analysis and decision making.

The above stated advantages are achieved by a system and method integrating the various regulated mandated processes needed to cleanup hazardous waste from impacted property or media. Project information stored in the same centralized database is utilized and shared by different modules. Thus, preventing redundancy of data processing and significantly enhancing the value of collected data.

These and other advantages are achieved, for example, by a system for environmental data management. The system includes an application including a mapping module that a generates an interactive graphical mapping interface of the site, the interactive mapping interface including links to environmental data from a site and related documents, an analysis module that analyzes the environmental data, the environmental data including contaminants of potential concern (COPC) data, a risk assessment module that assesses the human health risks caused by COPCs at the site, and a remediation module that screens remedial technology for cleaning up COPCs.

These and other advantages are achieved, for example, by a system for providing homeland security. The system includes a mapping module that a generates an interactive graphical mapping interface of the site, the interactive mapping interface including links to environmental data, the environmental data including contaminants of potential concern (COPC) data, a plurality of site monitoring systems that monitor COPC readings on the site, wherein the site monitoring systems provide real-time COPC readings, and a continuous monitoring system module that provides a user interface to the site monitoring systems and the real-time COPC readings from the site monitoring systems.

These and other advantages are achieved, for example, by a method for environmental data management. The method includes analyzing contaminants of potential concern (COPC) data for an object of a site, generating a three-dimensional (3D) display of the site, receiving a selection of a region-of-interest (ROI) in the 3D display, assessing health risks from COPCs in the ROI, and screening remedial technologies for cleaning up the COPCs in the ROI. The object represents a physical location on the site for which COPC data is measured and stored. The 3D display illustrates concentrations of COPCs at the site.

These and other advantages are achieved, for example, by a computer-readable medium comprising instructions for performing methods for environmental data management described herein.

These and other advantages are achieved, for example, by a graphical user interface (GUI) for environmental data management. The GUI includes an interactive geographic information system (GIS) map of the site, a site data section that includes site data, an object data section that includes data about a selected object from the site, and a plurality of selectable buttons corresponding to modules. The map includes links to objects displayed on the map. An object represents a physical location on the site for which environmental data is measured and stored. The modules corresponding to the selectable buttons include an analysis module that analyzes environmental data from a site, the environmental data including contaminants of potential concern (COPC) data, a three-dimensional (3D) viewer module that generates a 3D display of the site and the environmental data, a risk assessment module that assesses the human health risks caused by COPCs at the site, and a remediation module that screens remedial technology for cleaning up COPCs.

DESCRIPTION OF THE DRAWINGS

The detailed description will refer to the following drawings, wherein like numerals refer to like elements, and wherein:

FIG. 9 is a screen shot illustrating an interface for a calendar element of an embodiment;

FIGS. 11a–b are screen shots illustrating an exemplary central interface, a site analysis interface, and different kinds of analysis that can be performed for an entire site;

FIGS. 13a–h and 14a–d are screen shots illustrating exemplary human health risk assessment interfaces and different selection criteria and functions used in assessing potential health impacts related to site contamination;

FIGS. 16a–f are screen shots illustrating an exemplary remediation interface and a partial listing of appropriate remedial technologies screened and selected with associated remedial costs for each technology based on user determined unit price.

DETAILED DESCRIPTION

Embodiments of a method and system for a cradle-to-grave investigation and cleanup of hazardous waste impacted property (e.g., a hazardous waste site) will be understood more fully from the detailed description given below and from the accompanying drawings of embodiments, which, however, should not be taken to limit the method and system to a specific embodiment, but are for explanation and understanding only.

Embodiments include a web-based application that enables environmental data to be visually displayed, on screens including a graphical mapping user interface (e.g., a Geographic Information Systems (GIS) map), and accessed from a central database using a web browser. This web functionality may be used, for example, over a local intranet connection or through an Internet connection using the latest secure encryption technology to ensure complete data confidentiality and integrity. The central database may reside, for example, either locally within a local area network (LAN) or wide area network (WAN) or may be hosted externally. This web functionality is preferably accessed via webpages, or other graphical user interfaces (GUIs). A preferred embodiment sets itself apart with the innovative concept of organizing massive amounts of project data by location and by subject and making it available from one central location. The organization of project data in such a manner makes it possible to perform the necessary functions in a remedial investigation/feasibility study, hence, offering a cradle-to-grave solution. Project data relating to location or spatial information is organized using GIS technology. Project data relating to the chemical, hydrological, geological nature of the project site is organized by subject matter using a database.

With GIS technology, the project site data can be organized by layers. Each layer represents a different type of geographical objects such as a point, a line or a polygon. An object may represent, for example, a monitoring well (point), a pipeline (line), or a building (polygon). By placing objects into different layers, the objects themselves can be better organized. For example, the current gas pipeline network can be easily differentiated with the current sewer pipeline network which in turn can be easily discerned from the proposed sewer pipeline network.

Project data stored in a database is preferably associated to objects. The project data is more valuable when it is connected to the location of the object and vice versa. In order to perform the functions of a cradle-to-grave investigation and cleanup of hazardous waste impacted property/media, the project data in the database needs to be linked to the corresponding object. This is accomplished by creating a unique identifier for each individual object and assigning it to each data record in the database that relates to that object. This unique identifier is the link to the system 5 described below for FIG. 1.

Figure 1:
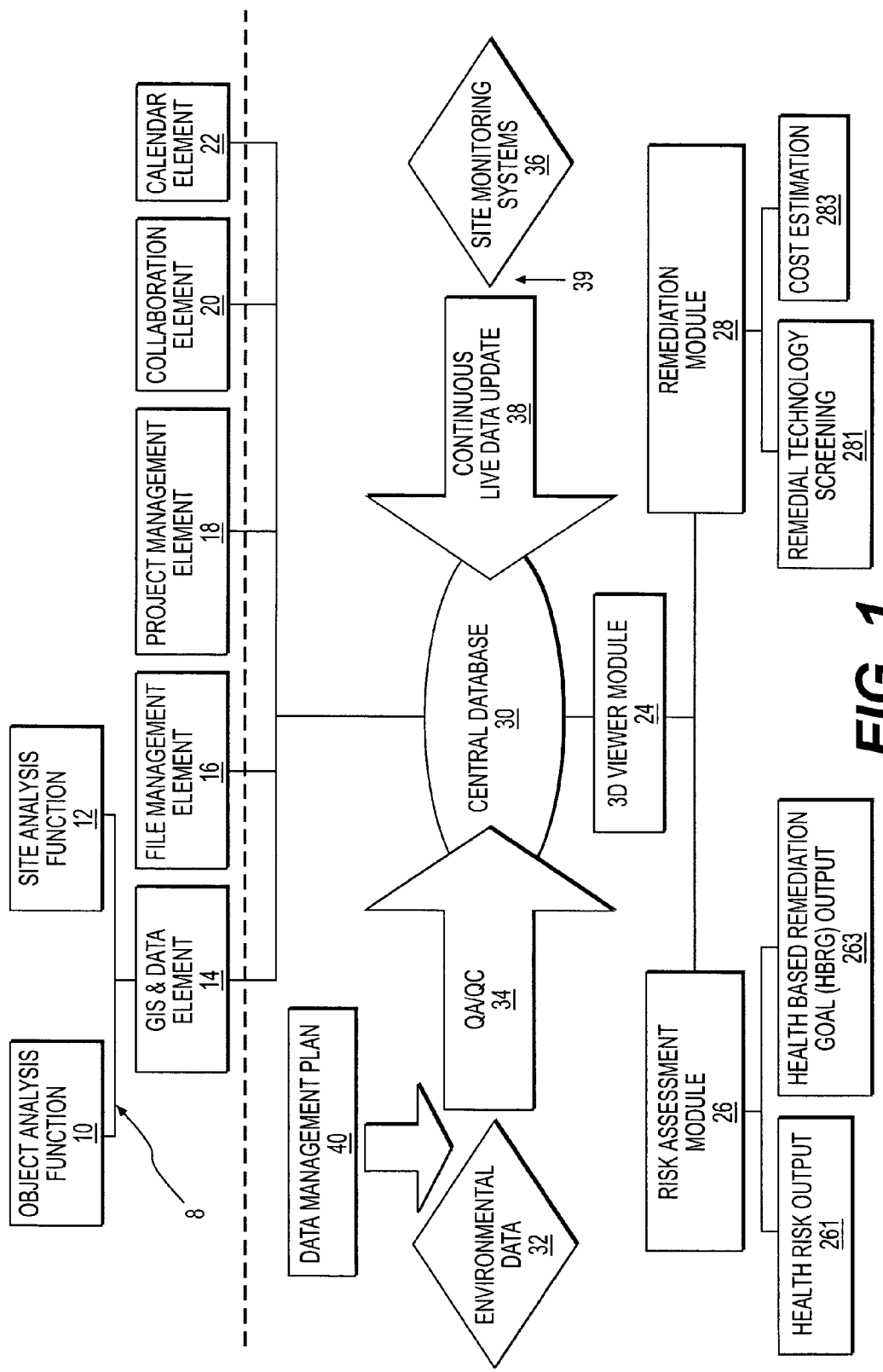
FIG. 1 is a diagram of an embodiment of a system for a cradle-to-grave investigation and cleanup of hazardous waste impacted property and environmental media.

FIG. 1 illustrates an fully integrated environmental data management system (EDMS) 5 for a cradle-to-grave investigation and cleanup of hazardous waste impacted property/media. Shown are various preferred components of the system 5 and their relation to one another. The components preferably include various software modules 8–28 that together, with the other modules, submodules, elements, functions, webpages, etc., described herein, comprise an EDMS application of the system 5. While described as separate modules, elements or functions, the functionality of modules 8–28 described herein may, for example, be combined into fewer modules, spread among more modules, or organized into different organizational components. The organization of the functionality described herein is illustrative.

These software modules preferably include an analysis module 8, a GIS and data element 14, a file management element 16, a project management element 18, a collaboration element 20, a calendar element 22, a three-dimensional (3D) viewer module 24, a risk assessment module 26, and a remediation module 28.

The EDMS application is preferably a web-based application loaded on an application server and run on user machines (e.g., see FIG. 2) that are accessing the system 5 through a web browser. Alternatively, the EDMS application may be loaded and run on a user machine that has access to the necessary file and database servers. Alternatively, the modules may be distributed over multiple user machines and/or servers. Either way, the modules are preferably all in communication with central database 30, from which relevant data is retrieved by the modules.

The modules 8–28 preferably enable the EDMS application of the system 5 to perform the following tasks seamlessly, among others, for example:

i) store, sort, query, and display chemical (and other contaminants), hydrological, geological, and other environmental data temporally and spatially from a hazardous waste project site;

ii) link project data, documents, reports, drawings, photos, and various files together, to be sorted by geo-referenced objects (e.g., representing monitoring wells) and accessible through those objects on a displayed GIS map;

iii) compute the extent of contamination including mass, volume, and impact area of contaminants;

iv) provide three-dimensional (3D) visualization of the site data to facilitate the understanding of complex site conditions;

v) calculate potential human health risks and develop remedial goals based on cleanup levels and land-use conditions specified by the user;

vi) follow U.S. Environmental Protection Agency (US EPA) algorithms and approach in determining appropriate remedial technologies for the cleanup of the site;

vii) calculate an estimate of site clean up cost;

viii) respond to client's queries on a real time basis, and strategize "what-if" scenarios effectively before taking actions in the field; and ix) allow a user to trace back the source (i.e., location, concentration, time) of exceedance if a user-defined what-if scenario fails the test or exceeds the regulatory standards.

These functions make the EDMS application a powerful tool in the execution and management of environmental projects. As such, the EDMS application keeps the project team focused, enhances the team's productivity and allows stakeholders to think and plan before they act. By making all the project data available, the project team is able to comprehend complicated site conditions, quickly and correctly identify impediments to project progress and offer scientific based workable solutions that guide the site to agency-approved closure. By having the ability to plan ahead and armed with comprehensive solutions to site closure, considerable cost savings can be attained, and closure approved in a shorter period of time.

Figure 5A:
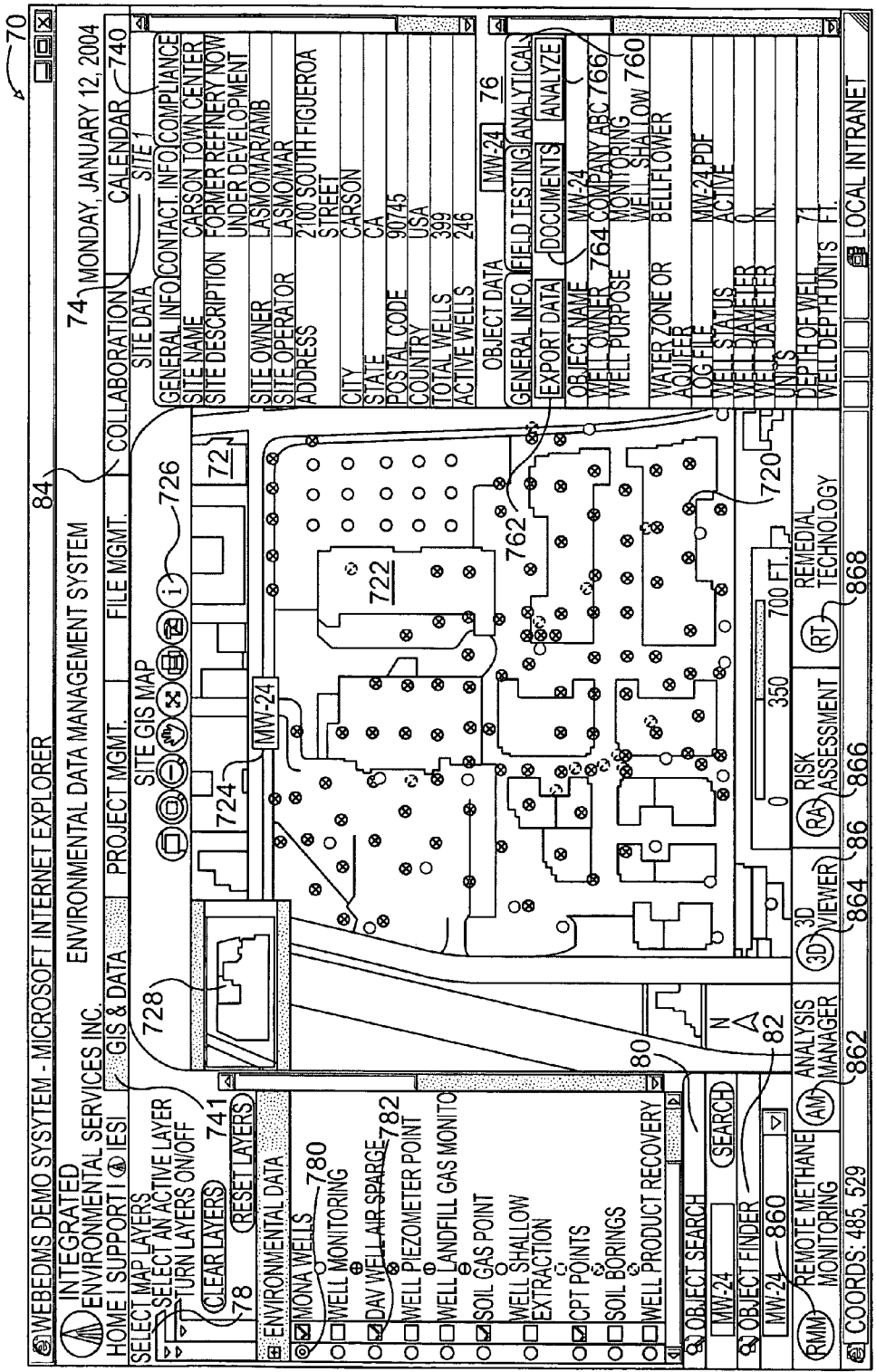
FIG. 5a is a screen shot illustrating an exemplary central interface and various ways to query project data and files spatially and temporally.

The analysis module 8 preferably analyzes environmental data 32 for individual project site objects or for an entire project site. Accordingly, with reference again to FIG. 1, the analysis module 8 preferably includes two sub-modules, an object analysis function 10 and a site analysis function 12. The object analysis function 10 analyzes project data for individual objects, e.g., selected through the GIS map, while the site analysis function 12 analyzes project data on an entire site basis. An example of a GIS map 72 is seen in FIG. 5a.

An object is a selectable item in the displayed GIS map that preferably represents a physical location on the project site for which environmental data has been (and is continuing to be) measured and stored. The environmental data at each object may be measured by any known means, such as, e.g., emission monitoring stations, monitoring wells, soil borings, soil vapor collection points, air dike probes, piezometer wells and vapor extraction wells (collectively, site monitoring systems 36). Site monitoring systems 36 may include sophisticated monitoring sensors that are able to collect and store the data remotely. Typically, there are multiple objects for each project site.

The site analysis function 12 preferably performs analyses on environmental data on a sitewide basis. For example, the site analysis function 12 preferably responds to user defined criteria and calculates the concentration and distribution of contaminants in the various media of the site. The site analysis function 12 preferably performs these calculations on the basis of object environmental data and analyses performed by the object analysis function 10. The site analysis function 12 preferably passes the sitewide environmental data and analyses' results to the 3D viewer module 24 for creation of the 3D display.

The analysis module 8 preferably includes, and may display on a screen generated by the EDMS application, state and federal regulatory levels for various chemicals and other contaminants (e.g., biological, radiological, or explosive hazards) according to standards and guidelines developed by the U.S. Environmental Protection Agency (US EPA) and state agencies. These regulatory levels preferably include various values that indicate that a hazard exists for the chemical or other contaminant or values that specify a regulatory limit for the chemical or other contaminant. The analysis module 8 preferably analyzes the environmental data for the individual objects or for the entire project site by comparing this data to the values of the state and/or federal regulatory levels or to user-defined values. Other analyses that can be performed, but are not limited to, include identifying hits or detection of contaminants of potential concern (COPCs) and displaying field testing results. The analysis module 8 may dynamically generate graphical charts and/or spreadsheets (e.g., in Microsoft Excel® format) in order to display the comparison results, e.g., on a screen generated by the EDMS application. The analysis module 8 preferably receives the environmental data 32 it analyzes through the GIS and data element 14.

With continuing reference to FIG. 1, the GIS and data element 14 preferably generates the interactive graphical mapping interface, the GIS map, to display a project site's environmental data and retrieves data/files from the central database and file server 30 using known GIS map generation methods. The data files retrieved from the central database and file server 30 may be of a variety of multiple formats and types, including but not limited to: text files, datasheets, Computer Aided Design (CAD) drawings, photos, notes, documents, schedules, etc. A project site's environmental data 32 preferably includes not only the chemical, or other contaminant (e.g., biological, radiological, or explosive) data, but also the geological data, hydrological data, and other physical data that describes the site (e.g., an aerial photograph or map of the site, site conditions, and other site data) or other planning data that describes project schedules. The physical data preferably includes the locations of objects on the site, which objects are preferably linked to their chemical data and geological data. From their linked locations on the GIS map, the chemical data linked to each object may be displayed when the displayed object is selected on the GIS map.

When an object is selected, the GIS and data element 14 preferably queries the central database 30 for the linked environmental data. Likewise, as described below, a user may also select only a subset of the objects of a site for display on the GIS map. Accordingly, the GIS and data element preferably queries the central database 30 for the environmental data (e.g., including the location of the object on the GIS map) linked to the selected objects. Moreover, when a user wants to analyze environmental data, the GIS and data element 14 queries the central database 30 for the data, retrieves the requested data, and passes the retrieved data to the analysis module 8. Consequently, the GIS and data element 14 may also be referred to as a query module. The user may request the GIS and data element 14 to spatially (e.g., by object location from the map) and/or temporally (e.g., by time period) query the environmental data for individual objects or the entire site.

With continuing reference to FIG. 1, the file management element 16, the project management element 18, the collaboration element 20 and the calendar element 22 are tools available in the EDMS application of the system 5 that are designed to help improve communication between project team members and enhance project productivity. The file management element 16 is preferably used to directly access, manage and organize project data and other files in a standardized directory structure. Preferably, the file management element 16 provides a secured file management system and only users with administrative privileges (e.g., administrators) are able to add or delete files or to modify attributes of the files.

The project management element 18 is used to view, manage, set and determine project resources, schedules and deadlines or other types of planning data. Planning data preferably includes project tasks, duration, cost, project team members that are preferably linked to project tasks. From the project tasks, the associated duration, costs, team members may be displayed when the displayed task is selected. The project management element 18, therefore, enables project team members, for example, to stay abreast of the status of the project, to view available project resources, to determine whether a task will be completed on time, to re-allocate project resources to better or more efficiently complete tasks, to keep track of project milestones, etc. The project management element may be built for example, upon Microsoft® Project, or other similar systems, but is not limited thereto.

With continuing reference to FIG. 1, the collaboration element 20 provides a centralized online area for project team members to share non-project related files, discuss topics, exchange information, and conduct online meetings. Accordingly, the collaboration element 20 preferably provides one or more chat rooms and bulletin boards, discussion forums, instant messaging and/or electronic mail capabilities.

The calendar element 22 provides an archival calendar for the project. The calendar highlights, e.g., project appointments, scheduled project meetings, and project milestones. The calendar may also include the deadlines set with the project management element 18. The calendar provides a simple way to share meeting schedules among project team members. Calendar appointments can also be added, modified or deleted with ease. Appointments that are added to the calendar may be automatically emailed to the selected team members.

With continued reference to FIG. 1, the modules 8–28 are preferably linked together to provide core functionality for the EDMS application. The modules 8–22 are preferably all accessible from the same central or main webpage displayed by the EDMS application (note: a webpage, as used herein, may mean a webpage, page, window, graphic user interface (GUI) or any other similar interface display means as would be known to one of ordinary skill in the art). FIG. 5a is a screen illustrating an exemplary central or main webpage 70 of the EDMS application. As seen in FIG. 5a, the central webpage 70 has selectable tabs corresponding to each of the modules 14–22 (note: to select, as used herein with regards to webpages, sections, menus, buttons, tabs, check boxes, radio buttons, etc., means to click, double-click, right-click, or any other similar means of selecting as would be known to one of ordinary skill in the art). Consequently, the modules 8–22 may be referred to as EDMS Central.

Modules 24–28 are preferably also accessible through the central webpage 70 displayed by the EDMS application as seen in FIG. 5a below. When these modules 24–28 are accessed through the central webpage 70, a new webpage is preferably displayed for each module. See, for example, FIGS. 6 to 16f.

With reference again to FIG. 1, the 3D viewer module 24 is a data visualization module that displays and models environmental data, preferably retrieved by the query module 14, in 3D space. The 3D Viewer module 24 preferably displays the characteristics of the ground surface by reading in a digital elevation model (DEM) of the site. The 3D viewer module 24 also preferably displays the 3D nature and extent of contamination of one or more chemicals and/or other contaminants in the site media (e.g., soil, groundwater, air, buildings). The 3D viewer module 24 may generate the display based on data and results received from the site analysis function 12 using known 3D display generation methods.

Figure 12A:
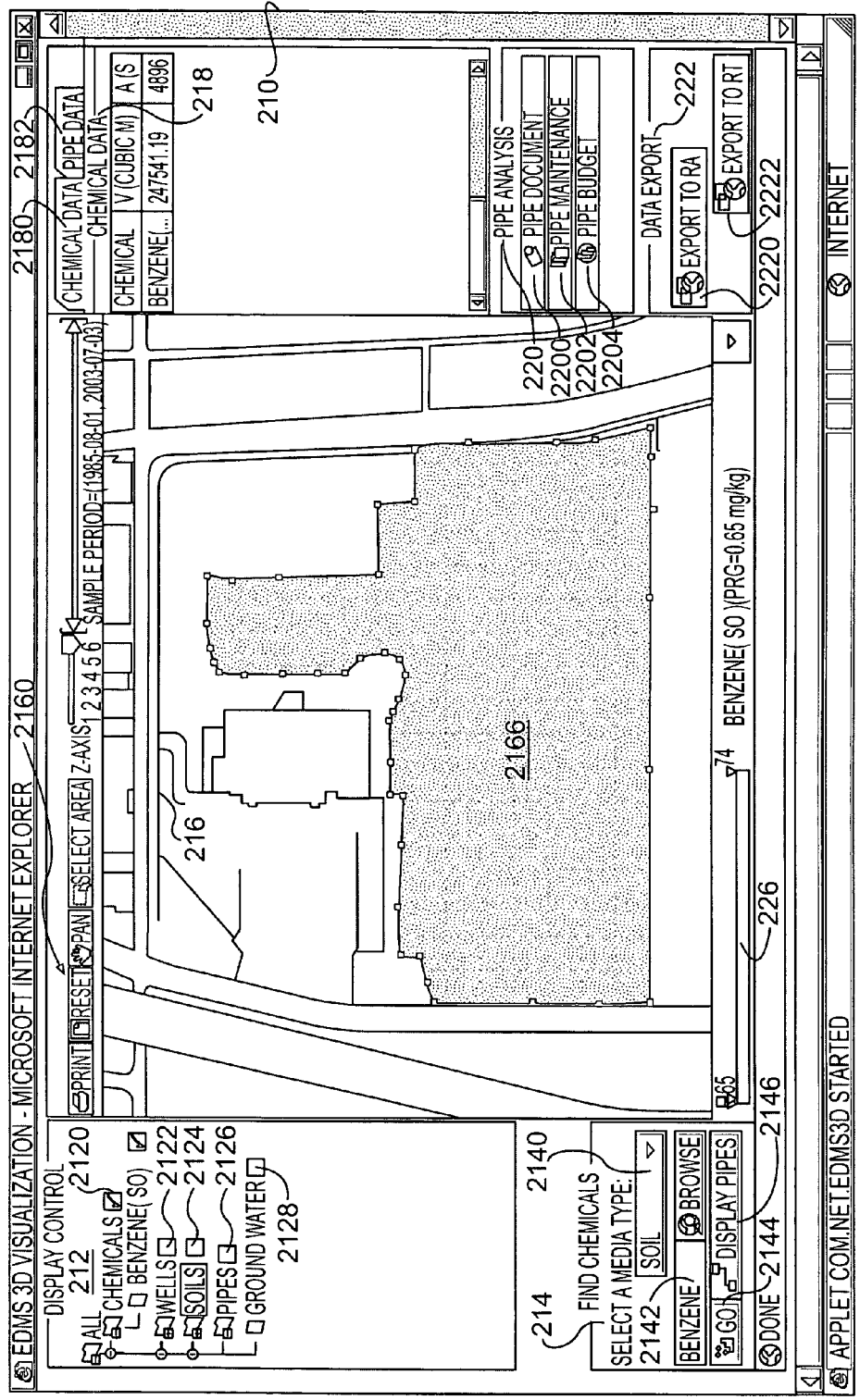
FIGS. 12a–b are screen shots illustrating subsurface site conditions such as monitoring well locations, underground piping, soil types, sample locations and concentrations, and possible extent of any selected chemical contaminant in soil underneath a project site area.
Figure 12B:

An example of a 3D display generated by the 3D viewer module 24 is shown in FIGS. 12a and 12b. FIG. 12a and 12b are screens illustrating a 3D display webpage 210 displaying the 3D nature and extent of benzene contamination below ground. The 3D display allows users to better comprehend the environmental data by visualizing the patterns of the contaminants and the selected environmental medium at each depth of sampling location. The environmental data displayed by the 3D display may be filtered, for example, by contaminant, sampling period (temporal queries), or region of interest (ROI). Using temporal queries, the environmental data can be displayed to show how contaminants have evolved over a given time period and to show the effectiveness of current or past remediation technologies.

The 3D viewer module 24 may also determine and display the 3D characteristics of monitoring wells, underground utilities and other underground (or aboveground) structures determined from the physical site data retrieved from the central database 30. The user may select which of these are displayed in the 3D display. The 3D viewer module 24 may also compute the mass, volume, and impact area of subsurface (or above-surface for air) contamination of one or more chemicals and/or other contaminants. These computational results are preferably passed as parameters to the risk assessment module 26 and the remediation module 28 for further analysis.

The 3D viewer module 24 also enables a user to spatially select a subset of environmental data by defining a ROI in the 3D display and having further analysis performed on the ROI. The ROI may be defined by the user outlining a shape (e.g., a polygon) in the displayed 3D data. The user may define the shape by clicking and dragging across the 3D display. The application preferably filters the environmental data to the ROI and creates a 3D visualization model of the ROI. By defining a ROI, users can focus their attention to a specific area of the site and perform a more detailed analysis. The 3D viewer module 24 may perform the above computations on this selected ROI. As stated above, these computational results are preferably passed as parameters to the risk assessment module 26 and the remediation module 28 for further analysis. Furthermore, when a ROI is defined for a site, the ROI and associated data (e.g., the computations and other environmental data) may be stored in the central database 30. The ROI and associated data are preferably linked to the site in the central database 30. Other modules, including the risk assessment module 26 and the remediation module 28 may later retrieve the ROI and associated data for further analysis.

Figure 15A:
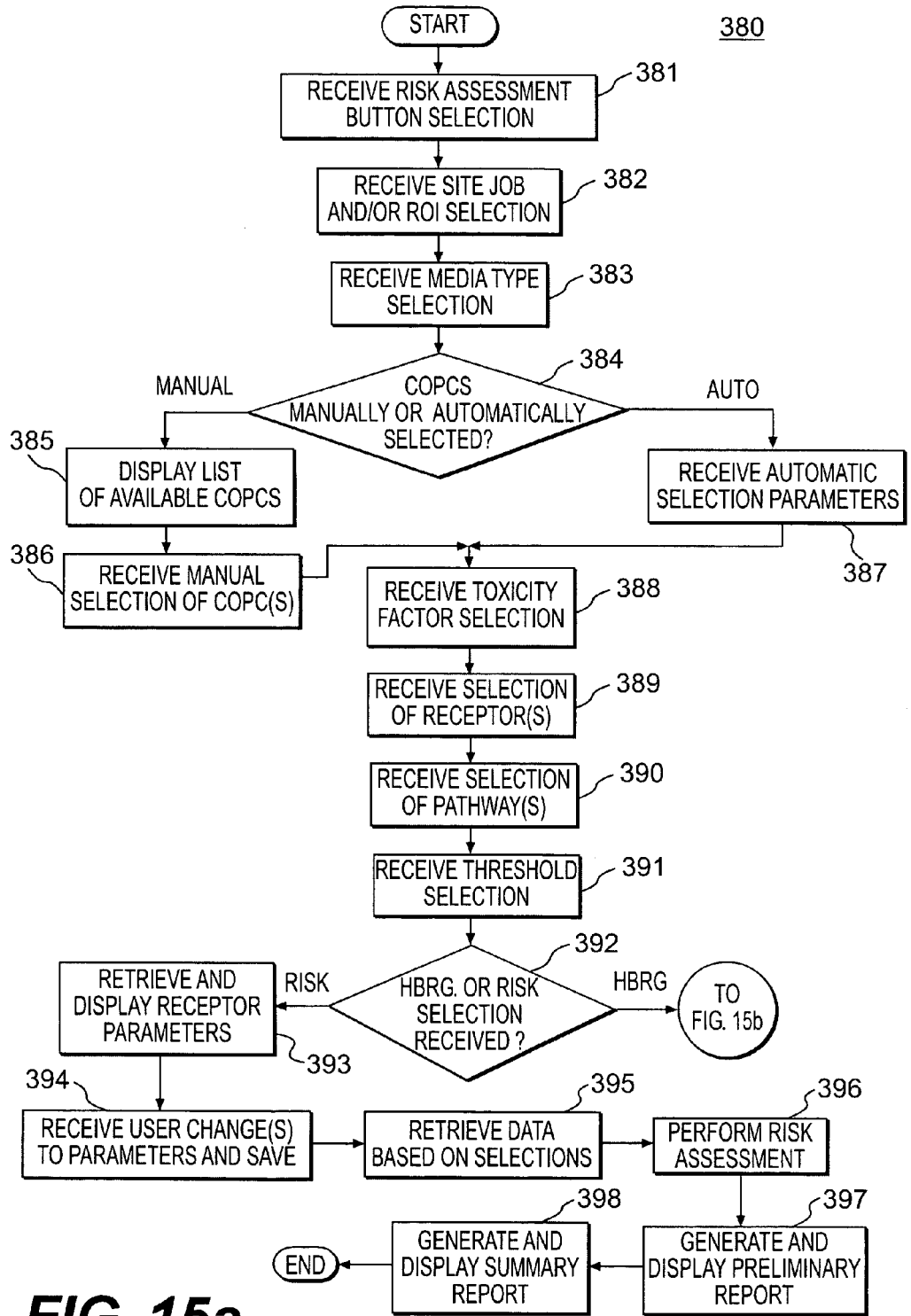
FIGS. 15a and b are flowcharts illustrating an embodiment of a risk assessment method.
Figure 15B:
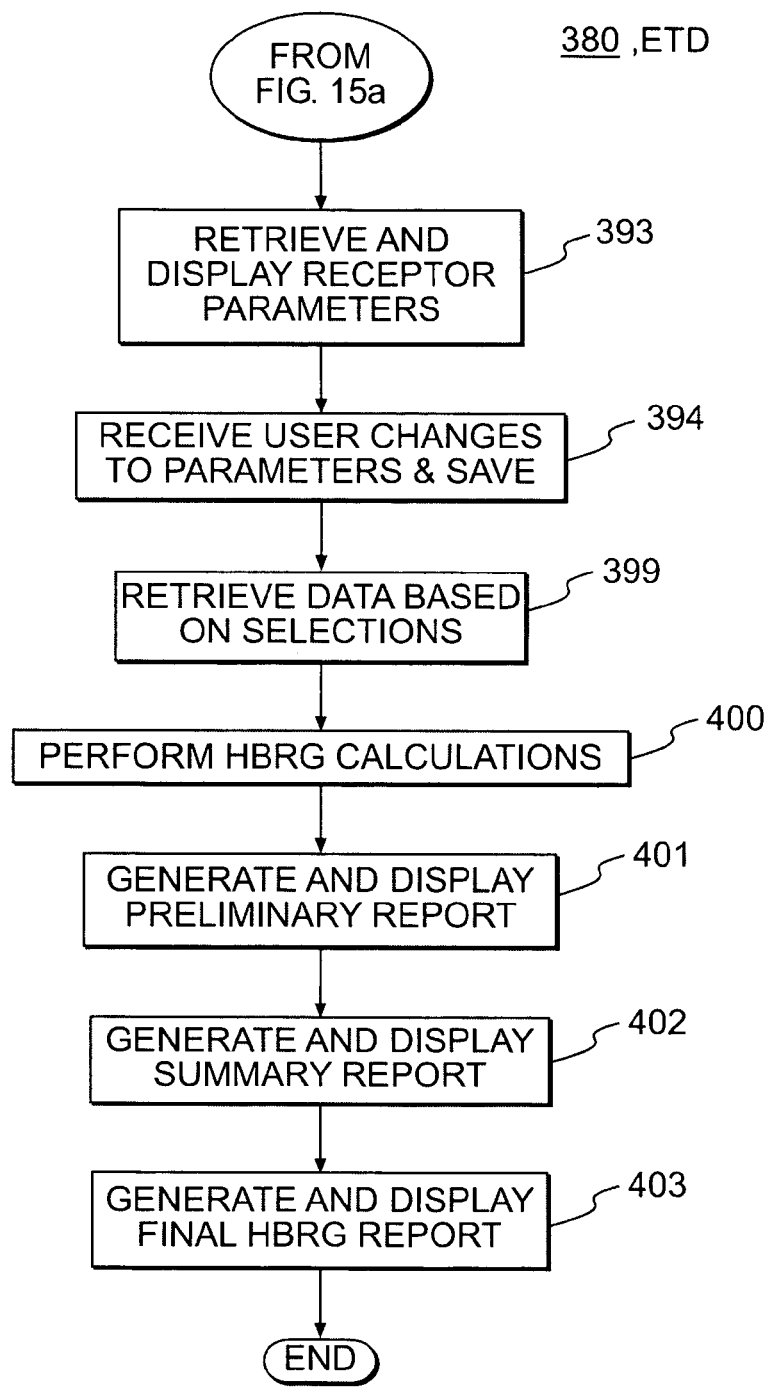

With continuing reference to FIG. 1, the risk assessment module 26 preferably calculates, in real-time, potential risks to human health derived from the site contamination. The risk assessment module 26 preferably also calculates the maximum allowable residual chemical concentrations or acceptable environmental cleanup levels (health based remedial goals (HBRGs)) for the site. These calculations are preferably based on the user-defined site landuse conditions, receptor type, exposure pathway as well as computations of mass, volume, and impact area of site contamination from one or more contaminants obtained from the 3D viewer module 24 and other site data obtained from the central database 30. The risk assessment module 26 may also be referred to as a web-based health risk assessment screening (webHRAS) module. FIGS. 15a–b illustrate an exemplary flow process of the risk assessment module 26, as described below.

In determining toxicity values and standards, the risk assessment module 26 preferably incorporates and automates complex chemical dose—receptor response relation algorithms stipulated by federal and state agencies. These algorithms include, for example, those outlined by the US EPA in the following publications: Superfund Exposure Assessment Manual, USEPA, Office of Remedial Response, Washington, D.C., EPA/540/1-88/001 (1988); *Guidance for Conducting Remedial Investigations and Feasibility Studies Under CERCLA,* USEPA, Office of Emergency and Remedial Response, Washington, D.C. 20460, EPA-540/G-89/004 (October 1988); "Human Health Evaluation Manual (Part A)," Volume 1, In *Risk Assessment Guidance for Superfund,* USEPA, Office of Emergency and Remedial Response, Washington, D.C., EPA-540/1-89/043 (December 1989); and, "Environmental Evaluation Manual," Volume II, in *Risk Assessment Guidance for Superfund,* Interim Final, USEPA, Office of Emergency and Remedial Response, EPA 540/1-89/001 (March 1989), which are all herein incorporated by reference. As such, the risk assessment module 26 preferably calculates the potential health risks or HBRGs, for selected exposed receptors and for selected exposure pathways, by executing one or more such algorithms on environmental data (e.g., the computations from the 3D viewer) contained in the entire site or from a ROI defined by the user.

Figure 13A:
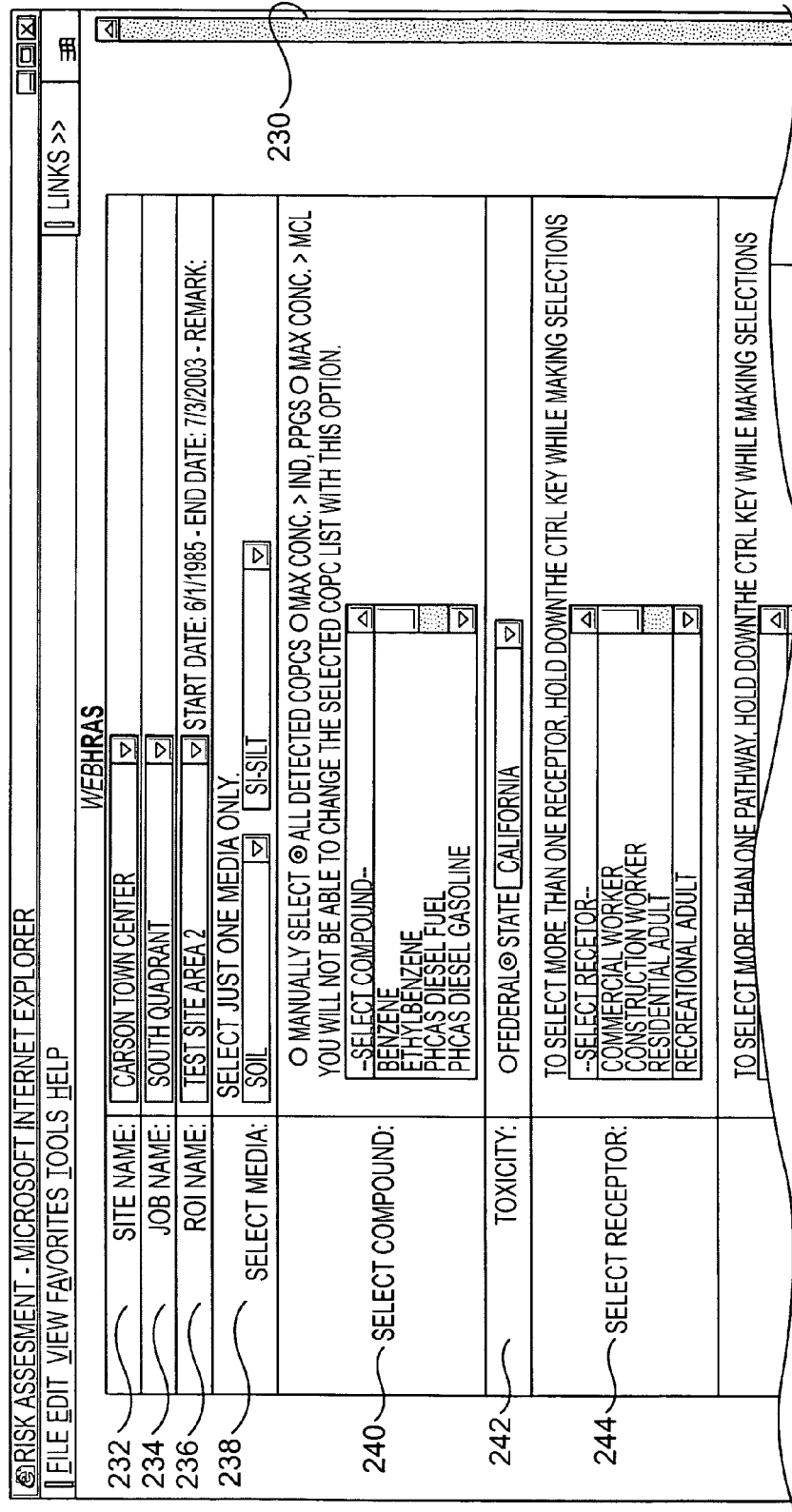

With continued reference to FIG. 1, the risk assessment module 26 preferably enables the user to select the site, a job name, the ROI, and the media (e.g., soil, groundwater, air), as well as the specific type of selected media (e.g., silt, clay, etc.), for the calculation. The risk assessment module 26 preferably performs the calculation based on, for example, all the COPCs in the site or ROI, a user-selected subset of the COPCs, or COPCs that have a concentration exceeding an allowable maximum in the media (e.g., according to the Projected Remediation Goal (PRG) of the selected algorithm). FIG. 13a is a screen depicting a main risk assessment that enables the user to make these selections, as well as the following selections, for the calculation. The risk assessment module 26 preferably performs the calculation for one or more user-selected receptors, e.g., commercial worker, construction worker, residential adult, recreational adult, residential child, recreational child, etc. Each type of receptor has certain US EPA default exposure parameters that are preferably set by the selected algorithm, as illustrated by the screen in FIG. 13b. Alternatively, these receptor parameters may be set or modified by the user. FIGS. 13c is a screen for modifying receptor exposure parameters. This allows the risk assessment to be more specific to the negotiated exposure conditions. Likewise, the risk assessment module 26 preferably performs the calculation for one or more user-selected exposure pathways, e.g., inhalation of indoor air, dermal contact, inhalation of outdoor air, ingestion, etc., as defined by the selected algorithm(s).

Additionally, the risk assessment module 26 preferably enables the user to characterize the chemical derived site-wide risk or ROI-related risk to human health. This risk assessment module 26 also determines the type of output produced (e.g., risk or HBRG). For example, the risk assessment module 26 may enable the user to select a risk-type output 261 or HBRG-type output 263 for the calculation. If a risk-type output 261 is selected, the risk assessment module 26 will then calculate the site contamination related health risk (e.g., carcinogenic risks, non-carcinogenic risks), for the selected receptor(s) and pathway(s) using the selected algorithm. The risk assessment module 26 may enable the user to select how the environmental data is statistically treated for the risk calculations. For example, a 95% Upper Confidence Limit (UCL) would require the risk assessment module 26 to calculate the risk using 95% upper confidence limit of detected chemical concentrations. Other statistical analysis such as average, maximum or minimum may be selected. If a HBRG-type output 263 is selected, the risk assessment module 26 will calculate HBRGs for the chemical-, receptor- and exposure pathway-specific scenarios using the selected algorithm. The HBRGs preferably are the maximum allowable residual chemical concentrations allowable in soil and/or groundwater based on the user-defined site conditions and target risk threshold levels.

With continued reference to FIG. 1, the risk assessment may also be characterized by an incremental lifetime cancer risk (ILCR) posed by the chemical contamination of the site. The ILCR is a numerical estimate of the carcinogenic potential as measured by a summary statistic. See, e.g., "Risk Assessment for Chemicals in the Environment," Burmaster, David, Ph.D and Wilson, Jeanne, Ph.D, D.A.B.T, incorporated herein by reference. The user may select a risk output 261 and the risk assessment module 26 will then calculate the cumulative ILCRs derived from a receptor exposed to COPCs present in the pathways identified. The risk assessment may also be characterized by a non-carcinogenic hazard quotient (HQ). The HQ is the comparison of the estimated intake level or dose of a chemical in air, water, or soil with its reference dose or concentration, expressed as a ratio. An HQ of less than one indicates that the exposure is unlikely to cause adverse non-cancer health effects. Similarly, the user may select a risk output 261 and the risk assessment module 26 will then calculate the cumulative HQs derived for a receptor exposed to COPCs present in the pathways identified.

Based on the selections described above, the risk assessment module 26 filters the ROI, media, contaminants, receptors, pathways, etc. and performs the risk assessment calculations as defined by the user. The results of the risk assessment calculations are preferably passed to the remediation module 28.

Figure 13D:
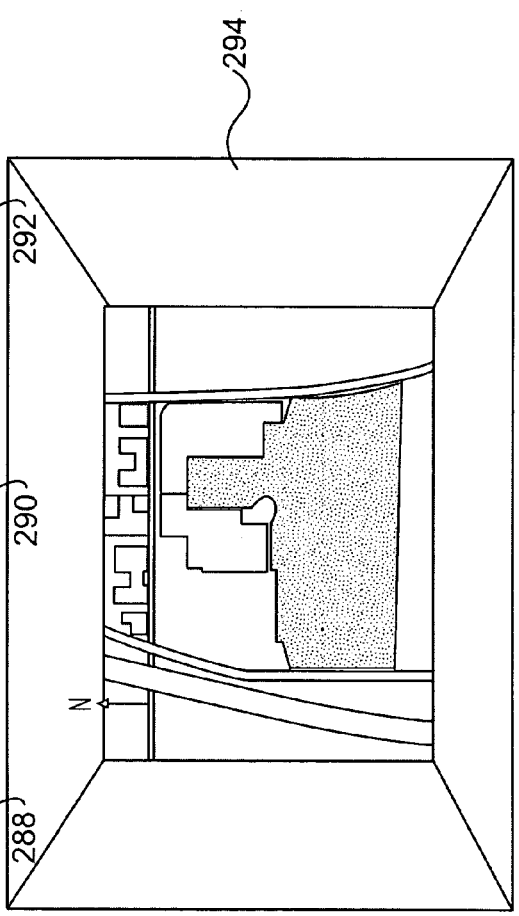

If a risk-type output 261 is selected, the risk assessment module 26 preferably produces a preliminary risk report listing each selected receptor, pathway, name and concentration of the contaminant, and COPC-, pathway-, and receptor-specific HQ and ILCR. Using algorithms of chronic daily intake (CDI) and reference dose (RfD), HQ is calculated. CDI refers to the amount of chemical intake over a long period of time measured by body weight and by duration. A reference dose is the daily exposure level which would not cause appreciable adverse non-cancer health effects after chronic exposures. Similarly, using algorithms of the CDI and cancer slope factor (CSF), ILCR is calculated. The CSF is the upper bound, approximating a 95% confidence limit, on the increased cancer risk from a lifetime exposure to an agent. This estimate, usually expressed in units of proportion (of a population) affected per mg/kg/day, is generally reserved for use in the low-dose region of the dose-response relationship, that is, for exposures corresponding to risks less than 1 in 100. See, e.g., "EPA Air Toxics Community Assessment and Risk Reduction Projects Database," herein incorporated by reference. An example of such a risk report is shown in FIG. 13d. FIG. 13d illustrates a screen including a portion of a first page of a Receptor and Pathway specific HQ/ILCR report for COPCs at a site ("Carson Town Center"), for job "South Quadrant," in silt-type soil, for dermal contact and inhalation of indoor air pathways. The risk report was prepared based on 95% Upper Confidence limit of measured COPC concentrations. As shown, the report includes results for commercial worker, construction worker, and residential adult receptors. The screen of FIG. 13d lists the dermal contact risk calculation results for COPCs for a commercial worker. The term "N/A" for the HQ or ILCR results shown in FIG. 13d means that a value for the CDI, RfD, and/or CSF is not available. Therefore, the corresponding HQ or ILCR cannot be calculated.

Figure 14B:
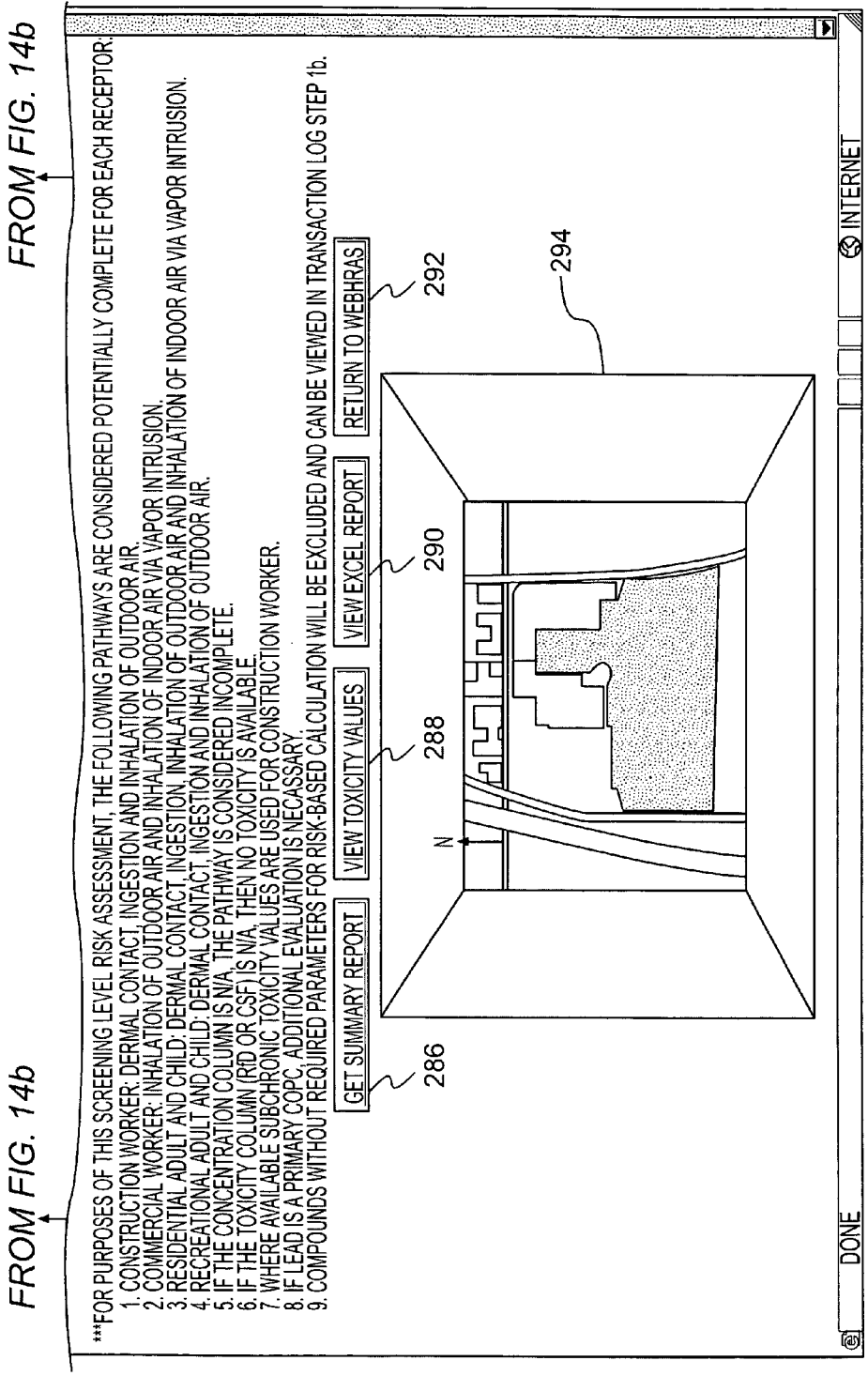
Figure 14D:
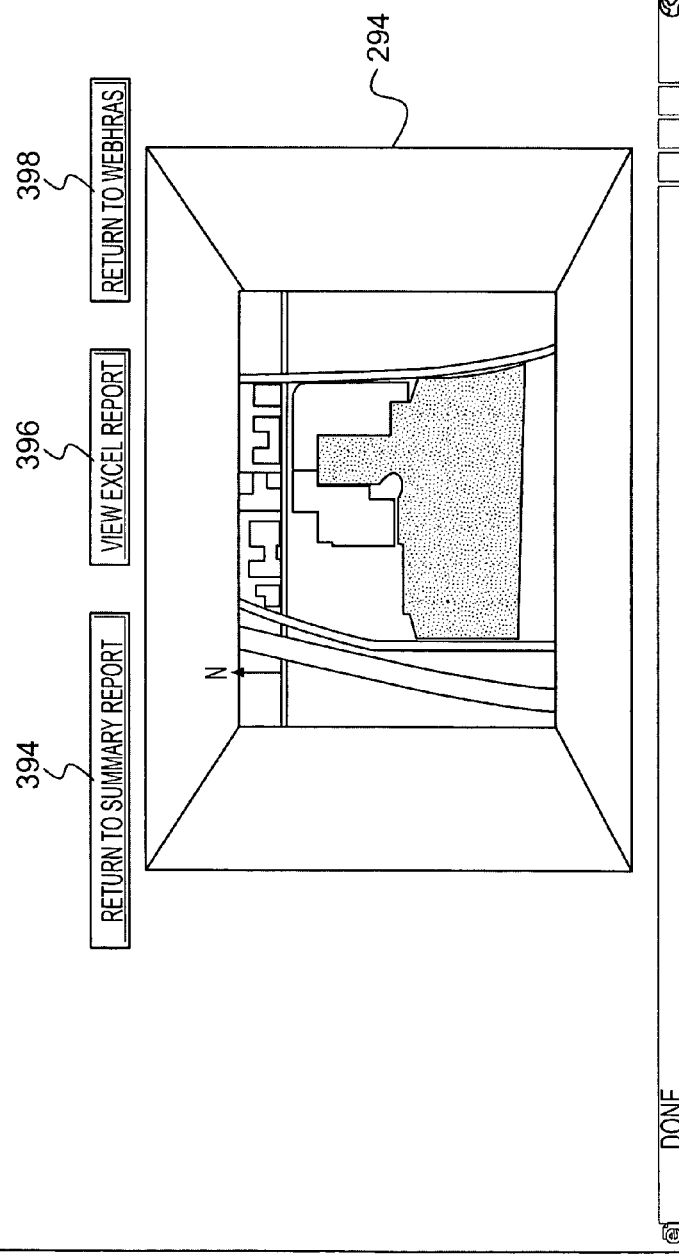

Alternatively, if a HBRG-type output 263 is selected, the risk assessment module 26 preferably produces a preliminary HBRG report listing the receptor-specific and pathway specific, non-carcinogenic (HQ-based) and carcinogenic (ILCR-based) HBRG for each chemical present in the user-defined ROI. An illustration of an example of a preliminary HBRG report 350 is shown in FIG. 14b. An example of a final HBRG report 370 is shown in FIG. 14d. FIG. 14d is a screen illustrating a final HBRG report for soil media for commercial worker, and residential child receptors for COPCs including benzene, ethylbenzene, toluene, xylenes, etc.

In the HBRG report, the risk assessment module 26 preferably lists the saturation concentration of the COPC in the medium identified and the receptor-, pathway-, and cleanup level-specific initial HBRG and final HBRG. HBRG is the maximum allowable concentration of each applicable COPC that may be present in the environment of the project site without posing an unacceptable health risk to a selected receptor. FIG. 14d is a screen illustrating a final HBRG report 370 for soil media for COPCs benzene, ethylbenzene, petroleum hydrocarbons (PHC) as diesel fuel, PHC as gasoline, perchloroethylene (PCE), Toluene, trichloroethylene (TCE) and total Xylenes for a commercial worker and benzene, ethylbenzene, PHC as diesel fuel, PHC as gasoline, PCE, Toluene, and TCE for a residential child.

Embodiments of the EDMS application, hence the system 5, may also include ecological and radiological risk assessment screening modules. These modules perform functions similar to the chemical health risk assessment module 26, although specifically for ecological risks or radiological risks. The results from such modules could likewise be passed to the remediation module 28 for remediation technology selection and costs estimates pertaining to remediating ecological and radiological risks present at the site. These modules can be applied to a homeland security embodiment of this application by identifying risk factors of potential targets such as facilities handling radioactive material.

With reference again to FIG. 1, the remediation module 28 preferably screens and selects appropriate remedial (cleanup) technologies based on results generated by and obtained from the 3D viewer module 24. The remediation module 28 also preferably estimates the costs of an environmental cleanup using the selected remedial technologies. Accordingly, an embodiment of the remediation module 28 performs two primary functions: a remedial technology screening 281, that screens and selects the remedial technologies, and a cost estimation 283, that estimates the costs to implement the different the types of applicable remediation technologies. The remediation module 28 may include separate sub-modules that perform the remedial technology screening 281 and the cost estimation 283.

Based on the HBRGs described above, the remediation module 28 uses the site's environmental data from the central database 30 to assist the user in selecting appropriate remedial technologies. The remediation module 28 preferably performs the screening and selecting of remedial technologies appropriate for meeting the HBRGs or PRGs stored in the central database 30 using the remedial technology selection approach and algorithms from the US EPA's *Remediation Technologies Screening Matrix and Reference Guide, 4$^{th}$ Edition,* which is hereby incorporated by reference. This screening matrix and reference guide is adopted by federal and state agencies and industries alike. The remediation module 28 preferably screens available remedial technologies and selects the appropriate remedial technologies for each contaminant or class of contaminants and affected media based on a host of parameters including technical feasibility, chemical (and/or other contaminant), geological properties of the site such as soil type and density and gas permeability and hydrological conditions of the site such as groundwater flow rate and hydraulic conductivity and regulatory acceptance of the technology. Based on the volume and concentrations of contaminants and affected media characteristics, the remediation module 28 preferably calculates cost and time estimates for the appropriate remedial technologies.

Figure 17:
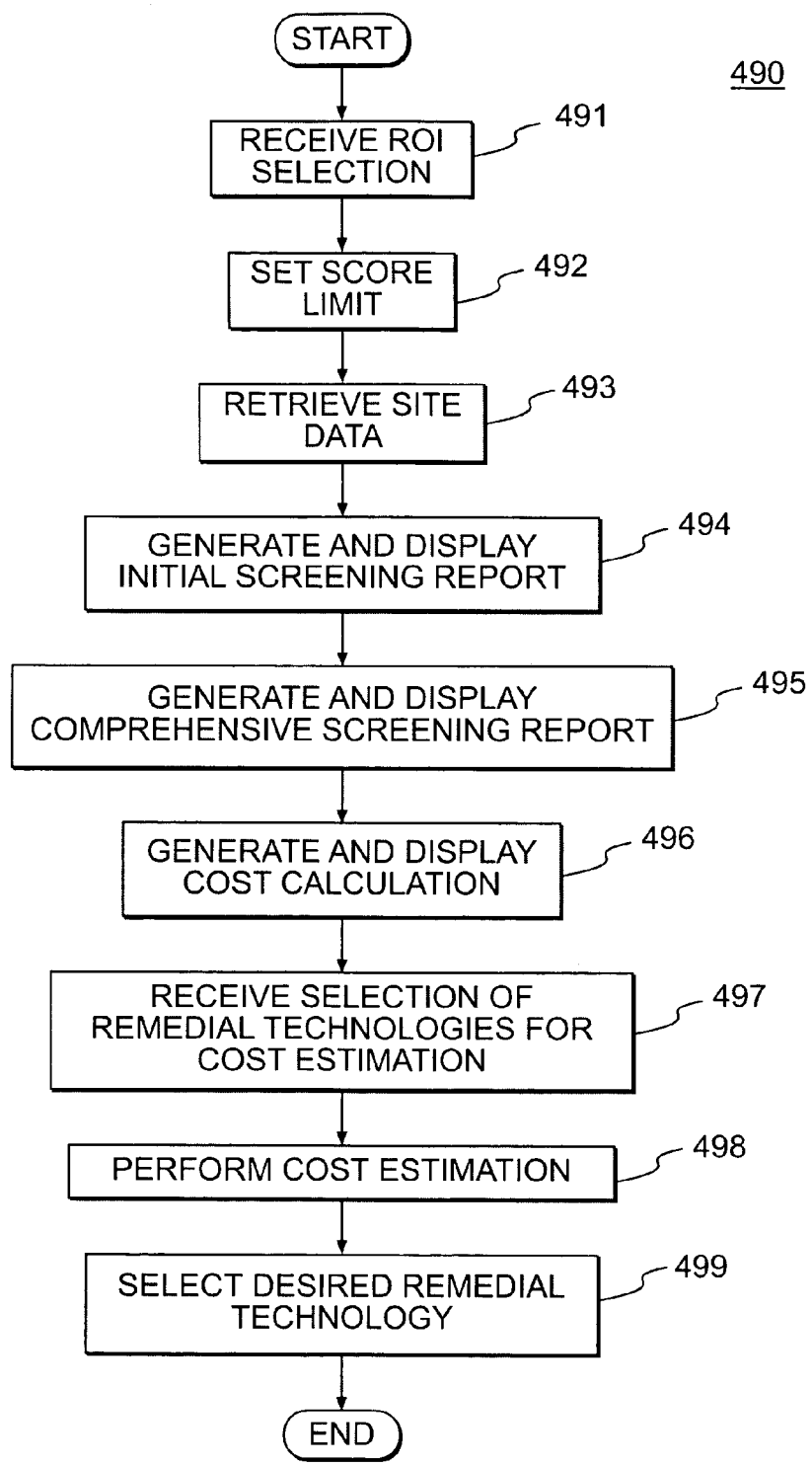
FIG. 17 is a flowchart illustrating an embodiment of a remediation method.

The remediation module 28 preferably generates an initial screening report, a comprehensive screening report, a cost calculator and transaction logs. These reports, and hence the remediation calculations, are preferably performed on a site-wide or ROI-basis. FIG. 17 illustrates an exemplary flow process of the remediation technology screening module, as described below.

Figure 16A:
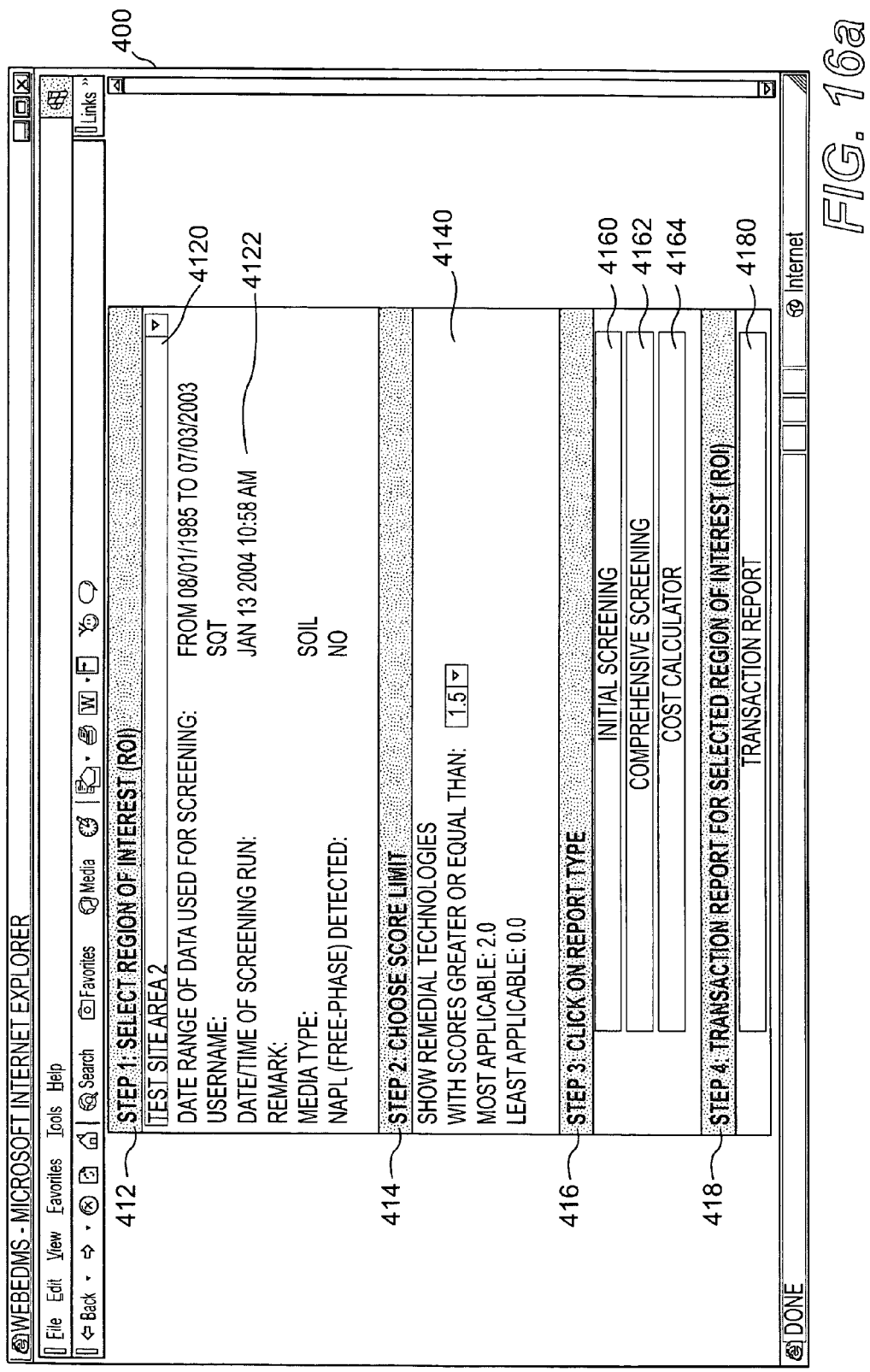

The screening process preferably assigns a rank or score indicating a level of applicability for each remedial technology. For example, the most applicable remedial technology is assigned a value of 2 and the least applicable remedial technology is assigned a value of 0. The remediation module 28 preferably enables the user to select a score limit that causes the remediation module 28 to only list remedial technologies with a score greater than or equal to the score limit in the reports, as illustrated in FIG. 16*a*.

The initial screening report generated by the remediation module 28 preferably lists the applicable remedial technology or technologies and their applicability score. The applicability score is based on the affected media type, contaminant type, contaminant concentrations, and other site-specific environmental data (e.g., chemical, hydrology and geology parameters) and known parameters of the remedial technology. The initial screening report may also list the required site specific parameter inputs required for comprehensive screening for each remedial technology. Such inputs include, for example, mass, area, volume, type and concentration of contaminants, non-acqueous phase liquid (NAPL) or non-NAPL technologies. FIG. 16*b* is a screen illustrating an exemplary initial screening report, as described herein.

The comprehensive screening report generated by the remediation module 28 preferably lists the applicable remedial technology(ies) and their applicability score from the initial screening report and a time estimate for completing the remediation for each remedial technology. The time estimate is preferably a rough order of magnitude time estimate based on the site-specific chemical, geophysical and geohydrological parameters. The comprehensive screening report may also include limitations on the applicability of the remedial technologies. FIG. 16*c* is a screen illustrating an exemplary comprehensive screening report, as described herein.

The cost calculator generated by the remediation module 28 preferably lists the information listed in the comprehensive screening report and performs the cost estimation 283 based on a user-entered unit price and the contaminant volume in the affected media (preferably calculated as described above with reference to the 3D viewer module 24). Alternatively, the unit price may be determined automatically, e.g., from a database of prices for remedial technologies. Likewise, the estimate may be calculated on a basis other than contaminant volume. FIG. 16*d* is a screen illustrating an exemplary cost calculator, as described herein.

Figure 16F:
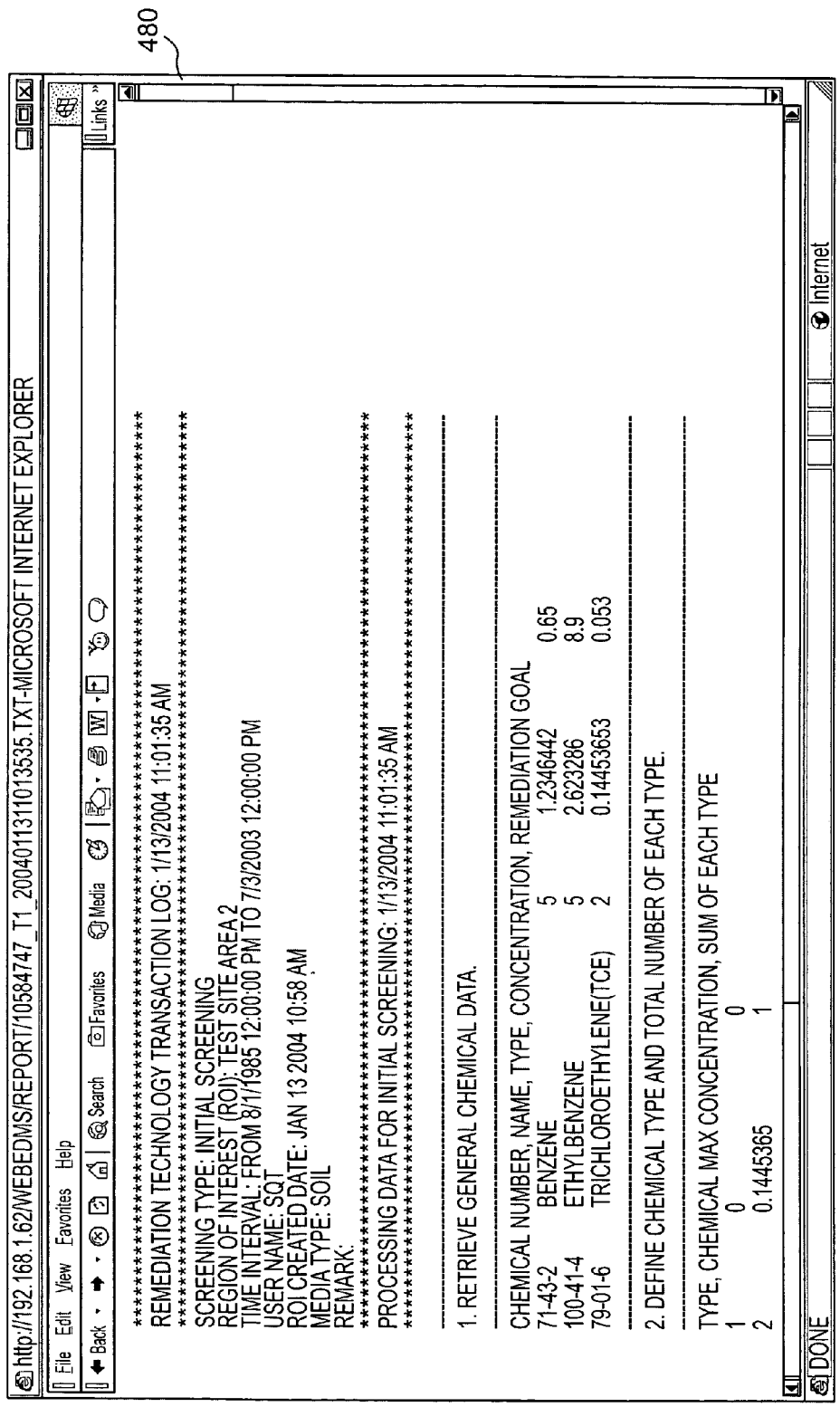

The transaction logs generated by the remediation module 28 preferably write out in detail the process, variables and calculations utilized in each report to arrive at a technology screening selection. FIG. 16*e* is a screen illustrating which transaction logs are available and FIG. 16*f* is a screen illustrating a transaction log, as described herein.

With reference again to FIG. 1, an important feature is the collection and storage of project site data in a central location. An exemplary central location is the central database 30. The central database 30 is preferably a relational database, enabling the modules 8–28 to perform the functions described herein. As discussed above, the modules 8–28 preferably all communicate with and access data from the central database 30. The modules 8–28 may also store the results of their analyses and calculations in the central database 30 for utilization by other modules. This allows the data to be consolidated and shared among the project team.

With continued reference to FIG. 1, environmental data 32 is entered into the central database 30. All incoming environmental data 32 preferably goes through stringent quality-assurance/quality-control (QA/QC) 34 procedures to ensure that only data that meets a data management plan 40 is entered into the central database. A data management plan 40 outlines and defines the processes and procedures associated with the collection, distribution, and reporting of environmental data gathered from the project site. Known QA/QC procedures (e.g., determining standard field definitions, avoiding duplicate values, maintaining data integrity and formatting data values to the correct standards) may be used for the QA/QC process 34.

The environmental data 32 entered into the central database 30 when the system 5 is first used for a site is preferably the initial manual and/or automatic readings from site monitoring systems 36. As described above, these readings may be taken from, for example, field sensors, emission monitoring stations, monitoring wells, soil extraction points, etc, and communicated over a network connection to the central database 30. However, if the system 5 is adopted for use with an already ongoing project, as will often be the case, there will already be a veritable archive of various environmental data for the site. In this situation, the initial environmental data 32 entered into the central database 30 includes this existing data. By including all the existing data, the system 5 allows users to analyze project trends to reveal complex relationships in the site's environmental data.

As the project continues, however, there may be a continuous live update 38 of environmental data from the site monitoring systems 36. Together, the site monitoring systems 36 and continuous live data update 38 provide a continuous monitoring system 39. The EDMS application may include a module that runs the continuous monitoring system 39, receiving the continuous live data update 38 from the site monitoring systems 36 and generating the webpages seen in FIGS. 10a–10b. Certain site monitoring systems 36 such as sensor equipment are preferably in communication with the central database 30 through a wired or wireless network. This sensor equipment may include multiple types that detect various types of contaminants such as chemical, biological, radiological and explosive agents. Preferably, these site monitoring systems 36 are able to transfer their readings directly to the system allowing for the latest environmental information to be available when performing analyses. These site monitoring systems 36 may include a user machine (e.g., a computer as described below) that is programmed to read the necessary environmental data (e.g., measurement(s)) and communicate the readings for entry into the central database 30. Alternatively, a project team member may read the necessary environmental data from the site monitoring system 36 and manually enter the readings into the central database 30 (e.g., using a hand-held PC). In this manner, the system 5 is dynamically updated with current environmental data 32 so that the analyses, conducted using the system 5, are up-to-date.

By being able to incorporate environmental data directly from site monitoring systems such as sensor equipment, an embodiment of the system 5 allows for better control of the remedial process and quicker response to site-related crises. Since the data is recorded electronically at the time of collection, it is immediately available over the Internet for analysis and reporting. The recorded data can be used to create charts of various historical activities at the project site. An embodiment of the system 5 allows for immediate notification of responsible parties through conventional methods of electronic communication such as email or text messaging via cell phones in the event of an alarm is triggered since the readings are being automatically entered to the system. This alarm can be triggered when a certain chemical has passed a pre-determined threshold limit.

The procedure of collecting data remotely through sensors can be applied to another alternative embodiment of the system 5 in the homeland security embodiment. Continuous collection of data at strategic target locations can detect changes in the amount of chemical/radiological/biological/explosive agents in the area allowing for early detection and the triggering of alert messages leading to early response times.

Figure 2:
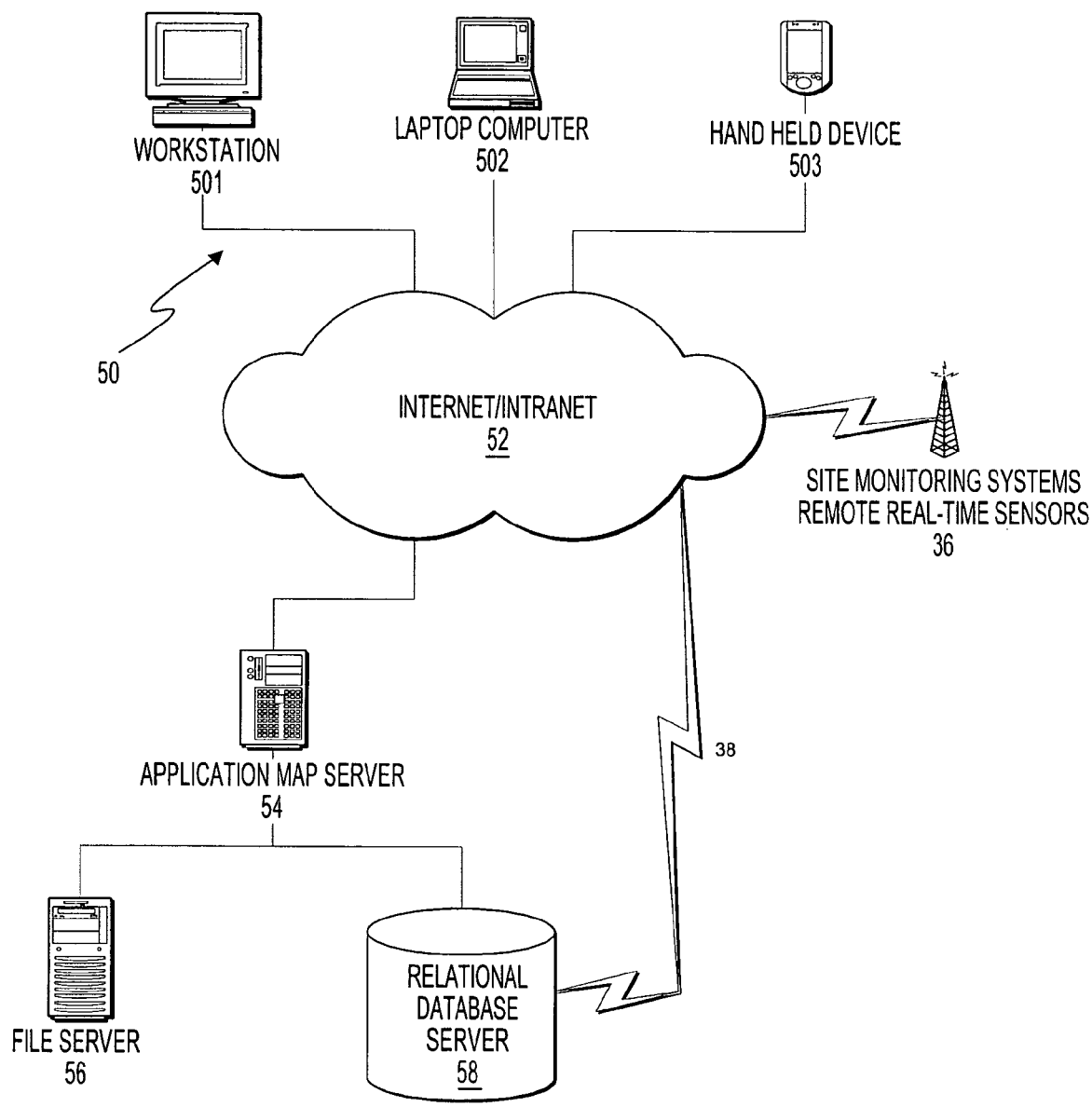
FIG. 2 is a diagram of hardware for a system for a cradle-to-grave investigation and cleanup of hazardous waste impacted property/media according to an embodiment operated remotely over a computer network.

With reference now to FIG. 2, illustrated is an embodiment of the hardware and network components of the system 5. Preferably any user machine 50, such as workstation 501, laptop computer 502, or handheld PC 503, that includes a processor, memory, secondary storage, input, display and supports a web browser may access the system 5 through the Internet or an intranet or other similar network (indicated as Internet/Intranet 52 in FIG. 2). When accessing the system 5, requests from the web browser of a user's machine 50 are transferred to the application map server 54. The application map server 54 preferably includes the EDMS application, including modules 8–28, described above. The application map server 54, running the EDMS application in response to requests from the user machine 50 web browser, preferably generates the maps and webpages of the EDMS application, including the screens described herein and illustrated in FIGS. 5a to 16e. Likewise, the application map server 54 preferably accesses and retrieves information such as files, documents and schedules from file server 56 and data from relational database server 58 based on incoming requests and as required by the EDMS application. The relational database server 58 preferably hosts the central database 30, which stores the environmental data described above. Site monitoring systems 36 provide the continuous live update of data 38, for example, by transmitting data through the Internet 52. The transmitted data is stored in the relational database server 58.

In an embodiment, the application map server 54 is built upon ESRI's® MapObjects development components using Microsoft® Visual Basic programming language, or other languages, but is not limited thereto. The file server 56 may be built upon a LINUX platform, or other O/S platforms, but is not limited thereto. The relational database server 58 may built upon Microsoft® SQL Server, or other database servers, but is not limited thereto. The application map server 54, file server 56 and relational database server 58 are preferably connected to the Internet/Intranet 52 in a conventional manner, such as via a local computer network, which may include one or more firewalls, routers and related devices (not shown). The operation of the Internet, computer networks, servers and user machines are well known to those of ordinary skill in the art and are not further elaborated upon here.

Figure 3:
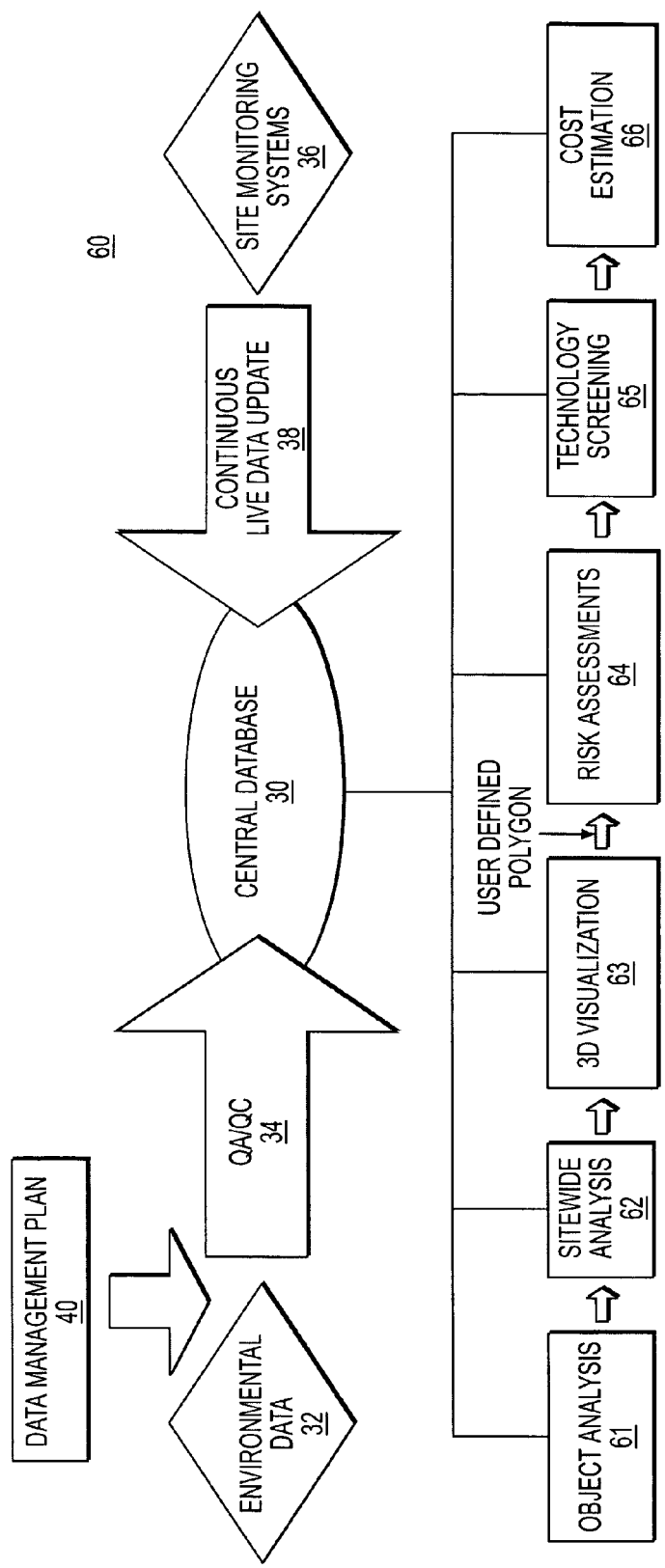
FIG. 3 is a flow diagram illustrating operation of an embodiment of a system for a cradle-to-grave investigation and cleanup of hazardous waste impacted property/media.

With reference now to FIG. 3, illustrated is a flow diagram showing how the system 5 may be used to fulfill the entire remedial investigation/feasibility study process seamlessly using information from the central database 30. Specifically, the flow diagram illustrates a method 60 of operation of processes or steps performed by the EDMS application of the system 5. These processes preferably correspond to the modules 8–28 illustrated in FIG. 1. As illustrated in FIG. 3, each process preferably communicates with the central database 30 to retrieve and/or store site data, as do the modules 8–28. Likewise, as shown, each process preferably passes information or data (e.g., computational results) to the next process.

With continuing reference to FIG. 3, the method 60 includes object analysis (step 61). The object analysis 61 is preferably performed by the object analysis function 10 of the analysis module 8. The object analysis 61 preferably retrieves object data from the central database 30, performs object data analyses, and displays object data and the analyses' results, preferably via the GIS & data element 24, as requested by a user through the GIS map 72 and the central webpage 70 of the EDMS application. A sitewide analysis (step 62) preferably performs analysis on the entire site's environmental data and may also display the sitewide data and analysis' results. The sitewide analysis 62 is preferably performed by the site analysis function 12 of the analysis module 8. Together, the object analysis 61 and sitewide analysis 62 support and provide the data query and analysis (EDMS Central) aspect of the system 5, as illustrated in FIG. 3.

With continuing reference to FIG. 3, a 3D visualization (step 63) preferably visualizes the site environmental data and analysis' results. The 3D visualization 63 preferably receives a ROI definition and performs 3D modeling of ROI-specific or site-wide data and results to display the 3D nature and extent of selected data in the site media. The 3D visualization is preferably performed by the 3D viewer module 24. Together with the data query and analysis aspect (e.g., the object analysis 61 and sitewide analysis 62) of the system 5, the 3D visualization 63 supports and provides a remedial investigation aspect of the system 5, as illustrated in FIG. 3, by allowing the user to understand the site conditions below the ground surface.

As described above, a user may preferably select a ROI in the 3D display for further study and assessment. Preferably, the selected ROI is defined by a user defined polygon. The 3D visualization 63 preferably calculates the mass, volume, and impact area of the contamination in the user defined polygon and passes this data to the risk assessment module 26. The risk assessment module 26 preferably calculates, in real-time, potential risks to human health derived from the site contamination and/or acceptable environmental cleanup levels (health based remedial goals (HBRGs)) (step 64). These calculations are preferably performed, as described above, by the risk assessment module 26. If ecological or radiological screening modules as well as ecological or radiological data are present, similar calculations may be performed for ecological and radiological risks.

With continued reference to FIG. 3, the risk assessment module 26 preferably passes the PRGs or results of its calculations (e.g., the HBRGs) to the remediation module 28 and the remedial technology screening 281 function. The remedial technology screening 281 screens and selects appropriate remediation technologies (step 65). The appropriate remediation technologies screened and selected by the remediation technology screening 281 function are preferably passed to the cost estimation 283 function.

The cost estimation 283 preferably estimates the cost of the remedial technologies (step 66), based on multiple parameters such as the type of contaminant, its concentration and remedial goal, mass, volume, impact area calculations, to name a few, from the risk assessment step 64. A final remedial technology may be selected based on the technology screening step 65 and cost estimation step 66. Together, the risk assessments 64, technology screening 65, and cost estimation 66 steps support and provide a feasibility study aspect of the system 5, as shown in FIG. 3. Together, the remedial investigation aspect and the feasibility study aspect enable the system 5, and hence the EDMS application, to provide cradle-to-grave investigation and cleanup of hazardous waste impacted property.

Figure 4:
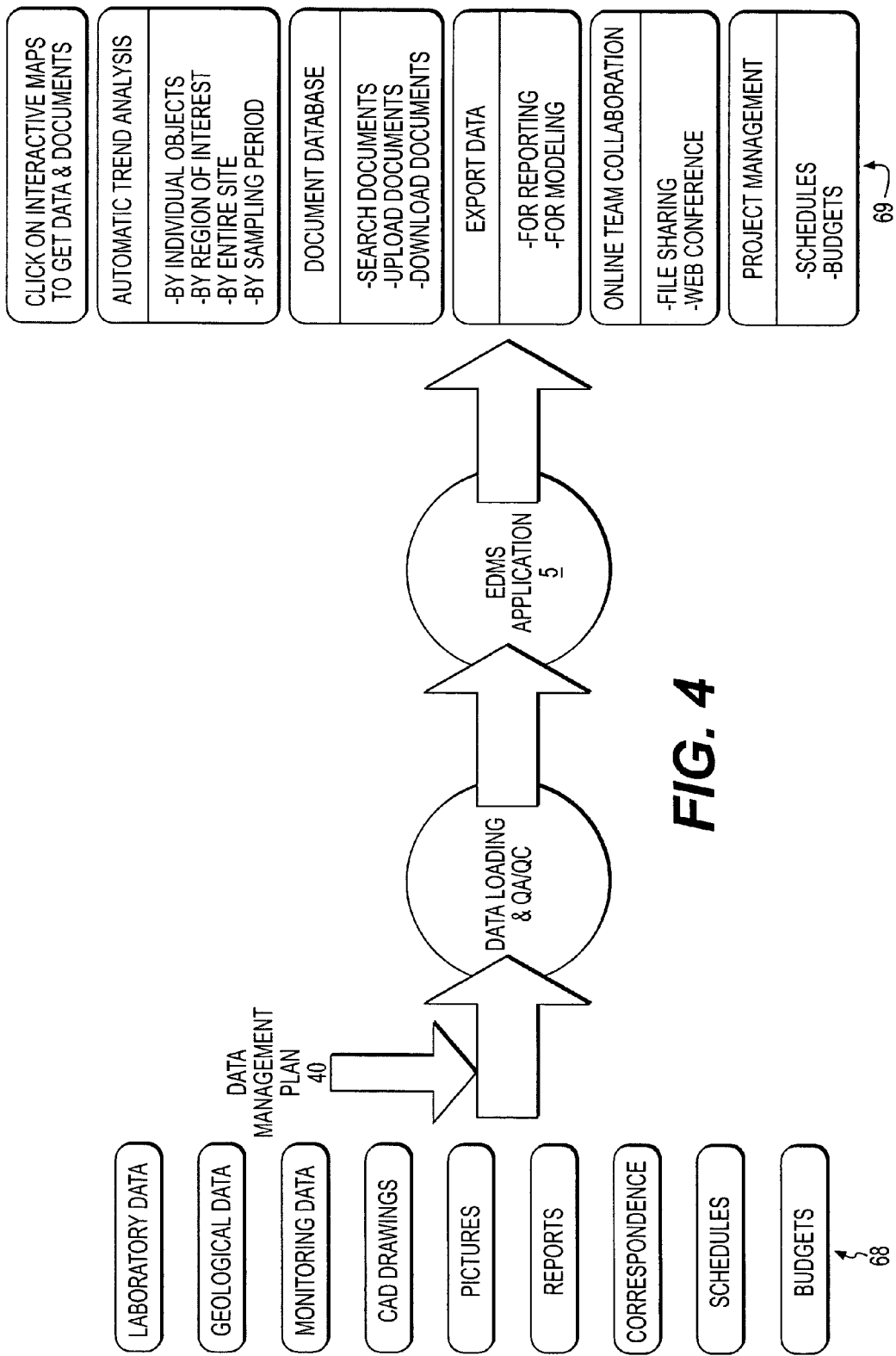
FIG. 4 is a diagram that illustrates consolidation of different types of project files by an embodiment of a system for a cradle-to-grave investigation and cleanup of hazardous waste impacted property/media to provide the results that are needed to bring the project site to agency approved closure.

With reference now to FIG. 4, shown is a diagram illustrating various project data and documents 68 that can be loaded into the system 5 and various uses 69 of the data and documents 68 by the EDMS application. As shown, the data and documents may include laboratory data (Lab. Data), geophysical data (Geo. Data), monitoring well data (Mon. Data), CAD drawings, pictures, reports, correspondence, schedules, budgets, etc. The data and documents 68 are preferably loaded into the system 5, as described above using data loading for data in electronic format (e.g. continuous live update 38 of data) and using QA/QC procedures for converting old, paperbound "legacy" environmental data.

Legacy environmental data originate from different sources in a variety of project data types and formats. In order to enter such data and documents into the system 5 in an organized and efficient manner, a data management plan 40 is developed. A data management plan 40 outlines and defines the processes and procedures associated with the collection, distribution, and reporting of environmental data gathered from the project site. The purpose of the data management plan 40 is to clearly communicate to the project team the project data format and transmittal requirements. Receipt of the data in the specified format will facilitate the inclusion and entry of the data into the system 5 and use of the data by the EDMS application.

The data and documents 68 are preferably stored in the file server 56 and the database server 58 (e.g., in the central database 30). The EDMS application, which consolidates various software components as described above (e.g., the modules 8–28, the GIS map, the databases, etc.), preferably analyzes and displays the data and documents 68 as described above. The various uses 69 may include, as shown, clicking on interactive maps (e.g., GIS map or 3D display) to get data and documents by individual objects (e.g., monitoring well) or by entire site; automatic trend analysis; document database functions, including searching, browsing, uploading and downloading; exporting data, including reporting (displaying) and modeling data and analysis results; online team collaboration, including file sharing and web-conferences, and project management, including scheduling and budgeting. Still other uses are described herein and/or apparent to one of ordinary skill in the art.

With reference now to FIG. 5*a,* shown is a screen illustrating an exemplary central webpage 70 of the EDMS application. The central webpage 70 shown includes the GIS map 72 for the current site, a site data section 74, a object data section 76, a select map layers section 78, an object search section 80, an object finder section 82, a module tab section 84 and a module button section 86.

The GIS map 72 shown is a geo-referenced aerial image or view (e.g., aerial/satellite photograph or a drawn map) of the project site. A geo-referenced aerial image displays the image in its true world coordinate space. The GIS map 72 includes hyperlinked objects 720 (described above) and building/structure outlines 722 overlaid on the image. When an object 720 or building/structure outline 722 is selected, the GIS map 72 displays a label 724 for the selected object 720 or building/structure 722 and displays the selected object's 720 data in the object data section 76. Objects 720 may be selected by clicking on the linked object 720 or as described below.

The GIS map 72 includes such functions as zooming (zoom in and zoom out), panning, printing, and other standard navigation functions. One other function available is an identify tool 726 that may be used to select an object 720 on the GIS map 72. The identify tool 726 is used to select objects by clicking on the object of interest on the GIS map 72 to obtain more information about the object which will appear in the object data section 76. The GIS map 72 may also include an overview map 728 that shows the area of the GIS map 72 in relation to the overall site.

The select map layers section 78 shown in FIG. 5a enables a user to select various layers of display on the GIS map 72. Since the system 5 has the ability to have a large variety of site information available, it is more efficient to organize the different map layers into categories. The select map layers section 78 enables selection of map layers organized into categories such as environmental data, new development(s), existing development(s), and base map information (see FIG. 11a). The GIS and data element 14 generate and display the GIS map 72 based on this selection. Map layers relating to environmental data such as monitoring wells and soil boring logs are organized in the environmental data category. Map layers that represent the existing and proposed site conditions are contained in the New Development and Existing Development categories. The Base Map Information category contains layers that represent the entire site such as aerial photography, site boundary and streets. The number of layer categories may change depending on the project and the different types of map layers used in the project.

With continued reference to FIG. 5a, in the environmental data category as well as the other categories, different types of objects, each representing a layer of display, may be turned on or off, e.g., by using an available checkbox 782. If a layer is turned off, the corresponding objects will not be displayed on the GIS map 72. This enables a user to focus on certain types of monitored contaminants or certain site monitoring systems 36, for example. Turning layers on and off will also help in managing the amount of information displayed on the map. Object layers can also be made active or inactive using, e.g., using a radio button 780. In the embodiment shown, object data is only obtained for display and analysis from layers that are active using the identify tool 726 and only one layer can be active at one time.

The object search section 80 and object finder section 82 enable a user to search for and select an object 720 on the GIS map 72. The object search section 80 preferably includes a text box for entering an object name and a search button for initiating a search of the GIS map 72 for the object named in the text box. The GIS and data element 14 may perform the search. The object search function searches for all objects in the entire project matching the object name in the text box. If the named object 720 is found in the GIS map 72, the GIS and data element 14 causes the GIS map 72 to zoom in and center on the selected object 720 and the object data for the selected object 720 is displayed in the object data section 76. Likewise, the object finder section 82 preferably includes an object pull-down menu or other menu displaying a list of available objects. The object pull down menu may only list all the objects in the current active layer only. If an object 720 is selected from the object pull-down menu, the GIS map 72 preferably zooms in and centers on the selected object 720 and the object data for the selected object 720 is displayed in the object data section 76.

With continued reference to FIG. 5a, the module tab section 84 shown includes tabs corresponding to the modules 14–22, as described above. Selection of these tabs (e.g., by clicking) preferably provides access to these modules. Specifically, a GIS & Data tab 741 preferably provides access to the GIS map 72, and hence the GIS and data element 14, and the sections shown in FIG. 5a.

The module button section 86 shown includes tabs and/or buttons corresponding to the site analysis function 12 and modules 24–28. As described above, selection of these tabs/buttons preferably provides access to these modules. Some of these modules are accessed through webpages or other GUIs separate from the central webpage 70. An analysis manager ("AM") button 862 preferably provides access to the site analysis module 12. A 3D viewer ("3D") button 864 preferably provides access to the 3D viewer module 24 and a 3D display (e.g., see FIGS. 12a–12b). A risk assessment ("RA") button 866 preferably provides access to the risk assessment module 26 and a series of risk assessment webpages (e.g., see FIGS. 13a–13e). A remedial technology ("RT") button 868 preferably provides access to the remediation module 28 and a series of remediation webpages (e.g., see FIGS. 16a–16f).

The module button section 86 may also include a remote methane monitoring ("RMM") button 860 that provides direct access to a continuous monitoring system 39. Selection of the RMM button 860 accesses webpages or other GUIs (e.g., see FIGS. 10a–b) displaying measurements from remote methane (or other COPCs) monitoring sensors. Preferably, these measurements are displayed in real-time.

The site data section 74 preferably displays site data. This site data is preferably retrieved from the central database 30 and/or generated (as analyses' results) by the site analysis function 12, as described above. As shown in FIG. 5a, the site data section 74 includes selectable tabbed listings 740 for general information, contact information and compliance. The general information tab shown includes the site name, description, owner, address, total number of monitoring wells, active wells, offsite wells, and other similar information that can provide an overall description of the site. The contact information tab includes contact information such as name, title, affiliation,, address, email, fax, phone, etc for the project site's team members. The compliance tab includes reference information to help identify the site by the US EPA and other agency identifiers. The type of information included in this tab is specific to each site. This tab preferably includes information such as Site EPA ID Code, Site EPA Region, Site SIC Code(s) as well as applicable laws, ordinances, regulations, standards, permits and any other site compliance date desired.

With continuing reference to FIG. 5a, the object data section 76 preferably displays object data corresponding to a selected object 720 on the GIS map. The object data is preferably retrieved from the central database 30 and/or generated (as analyses' results) by the object analysis function 10, as described above. The object data section 76 shown includes selectable tabbed listings 760 for general information, field testing and analytical. The general information shown includes the object name, owner, purpose, water zone or aquifer, log file name, status, diameter, diameter units, depth, depth units, and other similar information. The log file name is preferably hyperlinked so that the log file name may be selected to directly access the log file (e.g., a log file can be the boring log file of a monitoring well showing the different soil layers and well screening levels). Other files can be linked to the object using this similar method of hyperlinking making files easily accessible from one location.

Figure 11A:
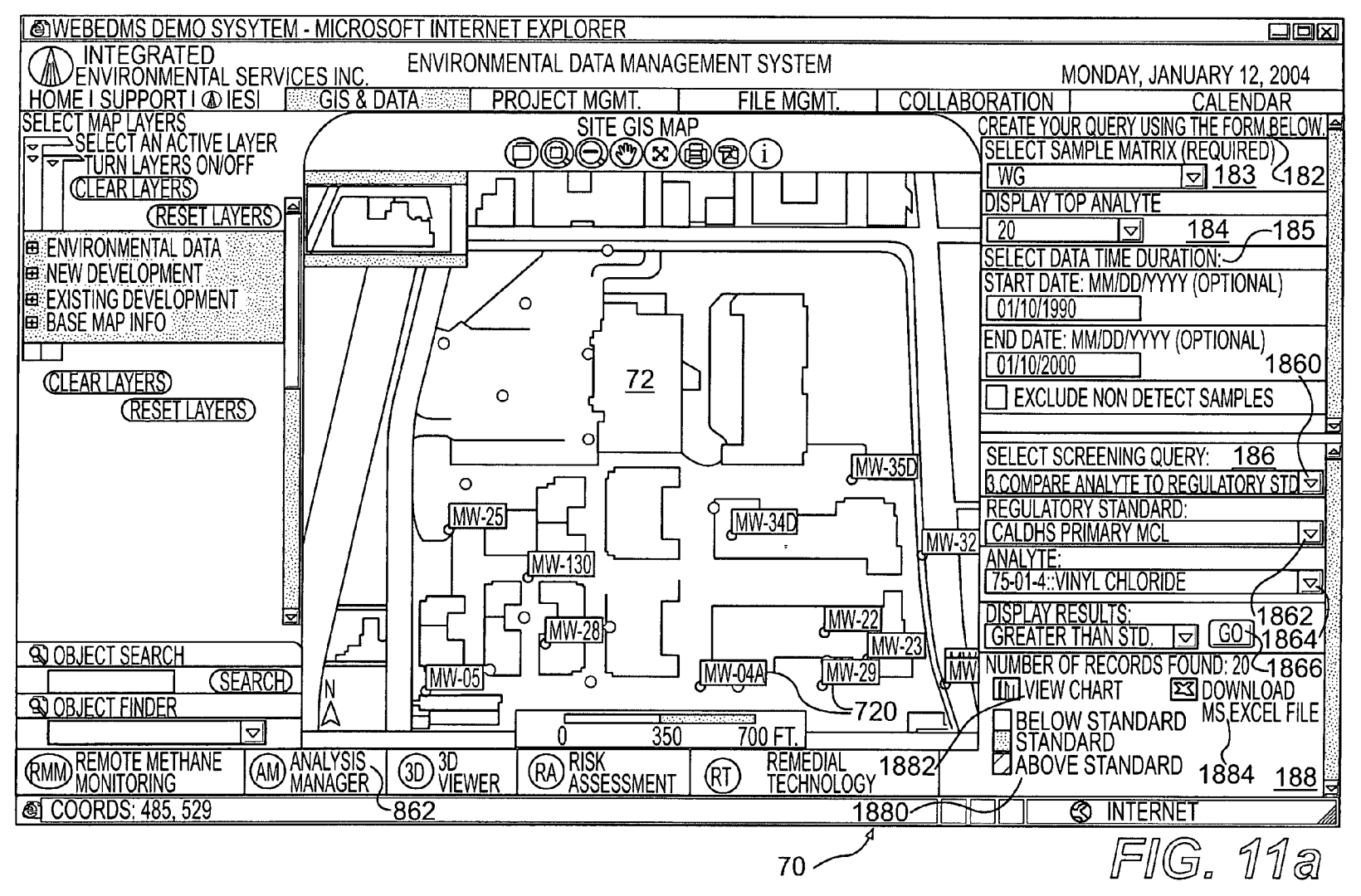
Figure 11B:
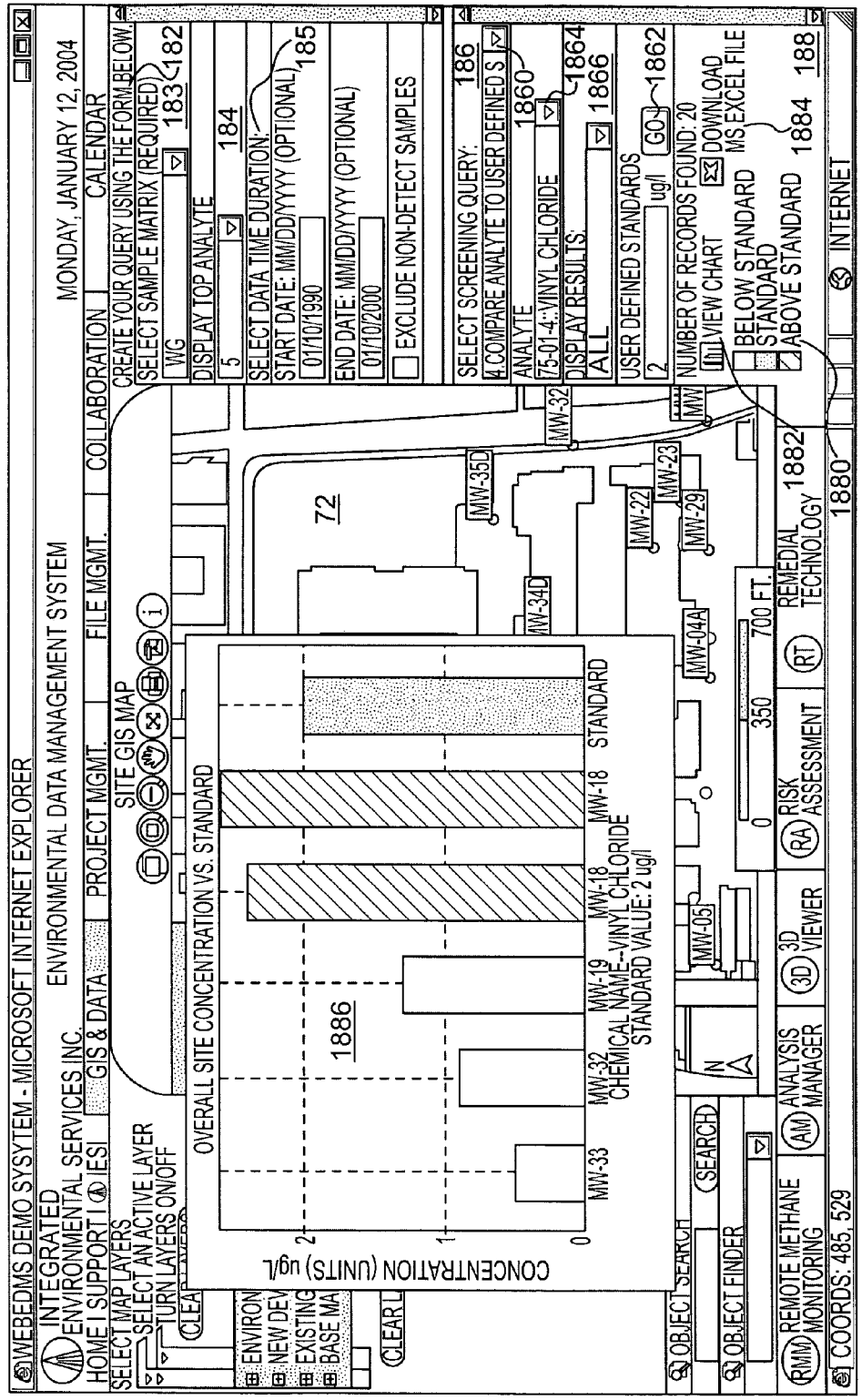

As shown, the general information also includes an export data button 762, a documents button 764 and an analyze button 766. The export data button 762 may be selected to open a window that enables the object data to be exported (e.g., all data corresponding to that particular object is exported to an Microsoft Excel® spreadsheet file format so that it can downloaded by the user). The documents button 764 may be selected to open a file management webpage that provides access to documents linked to the selected object 720 (see, e.g., FIG. 7). The analyze button 766 may be selected to access the object analysis function 10. Selection of the analyze button enables the user to select various object analysis options provided by the object analysis function 10. These options are similar to options provided by the site analysis function 12 accessible by selecting the analysis manager button 862 (e.g., as seen in FIGS. 11a–11b).

Figure 5B:
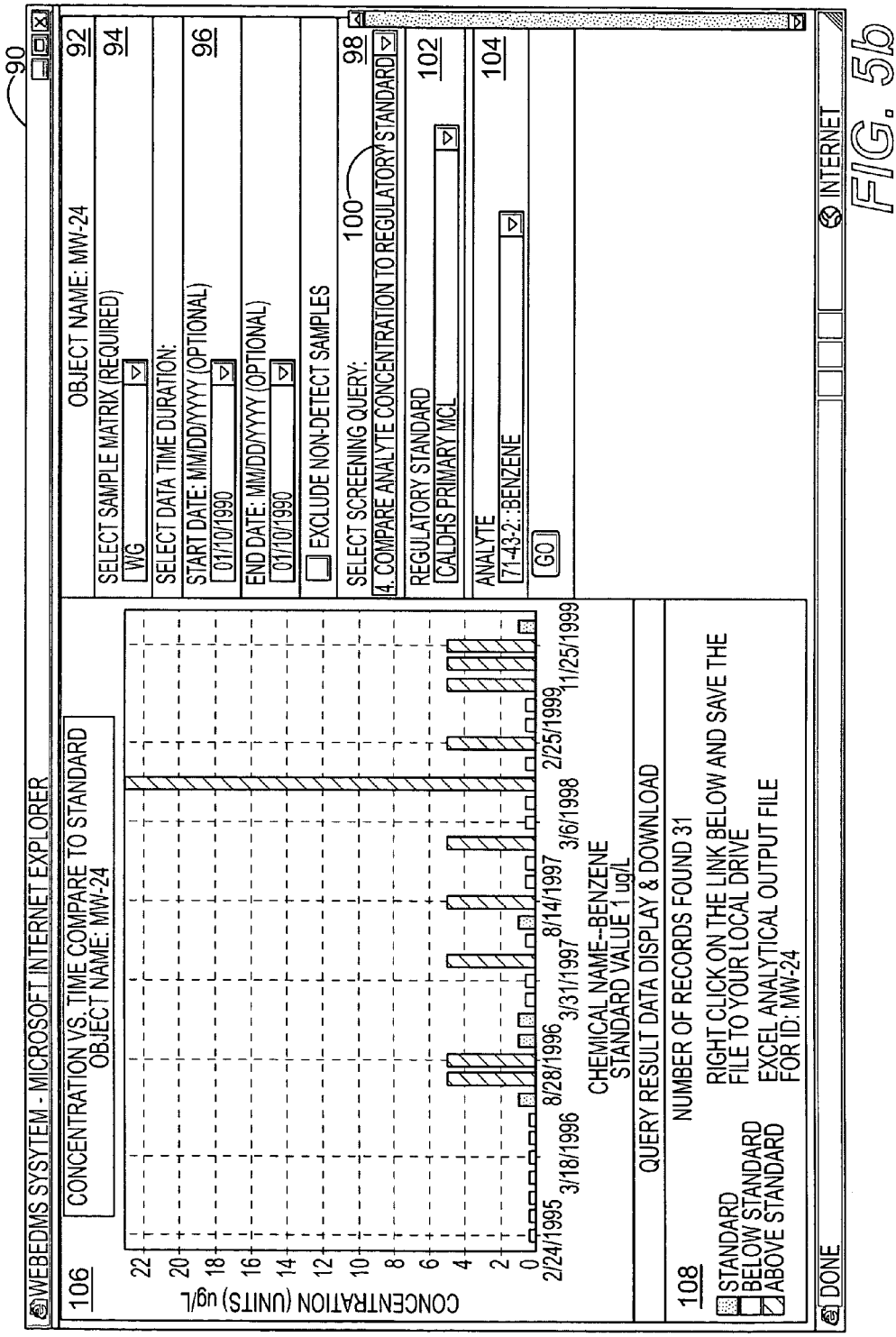
FIG. 5b is a screen shot illustrating an exemplary object analysis interface and kinds of analysis that can be performed on individual environmental objects.

FIG. 5b illustrates an object analyze webpage 90. The object analysis function 10 limits the query to one identified object while the site analysis function 12 reviews data for many objects at one time. Both analysis tools allow for the comparison of data in three categories: temporal (e.g., what happens to chemical concentration levels over time?), spatial (e.g., are elevated concentrations of chemicals present in a particular area?) and regulatory (e.g., where do concentrations exceed clean-up goals or regulatory standards?). The operation of the object analysis function 10 accessed by the analyze button 766 is similar to the operation of the site analysis function 12 accessed by the analysis manager button 862, which is described below with reference to FIGS. 11a–b.

The object analyze webpage 90 shown is used to analyze a single object. The object analysis function 10 may perform a temporal data comparison of analyte readings detected by the selected object and a screening of the contaminant readings. Accordingly, the object analyze webpage 90 includes a data comparison section 92. The data comparison section 92 preferably includes a sample matrix pull-down menu 94 and a data time duration section 96. The sample matrix pull-down menu 94 enables selection of a sample matrix. The sample matrix is the medium (e.g., groundwater (WG), soil (SO) or soil gas (SG)) in which the data comparison is performed.

The select data time duration section 96 enables selection of a time period for the temporal comparison. The select data time duration section 96 may include a start-date text box, an end-date text box, and an exclude non-detect samples checkbox. The select time duration section 96 can be left blank, in which case there will be no temporal limit placed on the comparison.

The object analysis function 10 retrieves contaminant readings, from the selected object, over the selected time period and according to the selected sample matrix. If the exclude non-detect samples check box is checked, these temporal comparison results exclude non-detect samples. Non-detect samples are samples with detection limits that are not known.

With continued references to FIG. 5b, the object analyze webpage 90 shown also includes a data-standards/limits comparison section 98. The data-standards/limits comparison section 98 shown includes a select screening query pull-down menu 100, a standard/limit selection pull-down menu 102, and an analyte selection pull-down menu 104. An analyte is a contaminant that the analysis module 8 has determined is present at the site. The data-standards/limits comparison section 98 enables a user to enter a query comparing an analyte to a regulatory standard, a user-defined standard, or some other limit. The data-standards/limits comparison determines whether the detected analyte is below, at or above the standard or limit, on an entire site basis.

The screening query pull-down menu 100 enables the selection of the type of comparison (e.g., method and analyte, analyte, analyte to regulatory standard, analyte to user-defined standard). For example, the comparison selected in FIG. 5b is an analyte to regulatory standard comparison. The standard/limit selection section 102 varies according to the type of comparison selected. With the analyte to regulatory standard comparison selected, section 102 is a pull-down menu enabling selection of a specific regulatory standard for the comparison. The analyte selection pull-down menu 104 enables selection of the analyte to be compared. The analytes listed in the pull-down menu 104 are determined by the object analysis function 10 from the selected objects environmental data stored in the central database 30. The data-standard/limits comparison section 98 preferably includes a go button that is selected by the user to perform the comparison.

When the data-standard/limits comparison is performed, the object analysis function 10 may generate a chart 106 graphically indicating the results of the data-standard/limit comparison for the selected analyte. As shown, the chart 106 depicts the amount of concentration for readings of the selected analyte (in the example shown, the contaminant Benzene) read at a selected object (in the example shown, object MW-24) over the time-period selected in the select data time duration section 96 compared to the standard selected in the standard/limit selection section 102. The chart 106 shown includes a color-coded key 108 that indicates whether a concentration of the selected analyte is below, at or above the standard/limit for the selected object. The chart 106 may also include a button that may be selected to download a file with the results of the comparison. Preferably, the results are downloaded into a spreadsheet file.

Figure 5C:
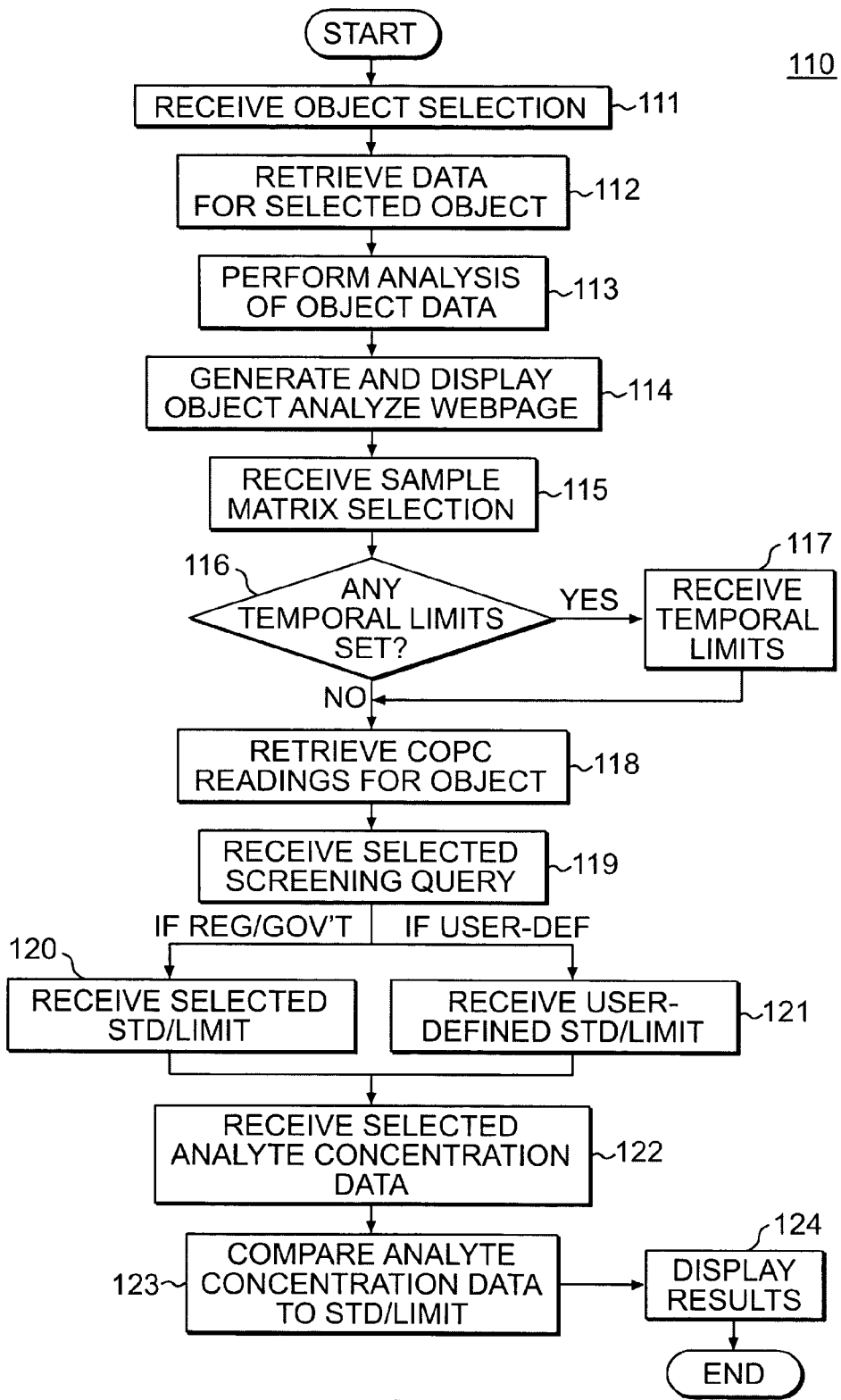
FIG. 5c is a flowchart illustrating an embodiment of an object analysis method.

With reference now to FIG. 5c, shown is a flowchart illustrating an exemplary object analysis method 110. The object analysis method 110 shown includes steps performed by the object analysis function 10 as described herein with reference to FIGS. 5a and 5b. The object analysis function 10 receives an object selection (block 111). An object may be selected using the central webpage 70, the GIS map 72, and in other manners described herein. The object analysis function 10 retrieves object data for the selected object, preferably from the central database (block 112). The object analysis function 10 may only retrieve current data for the selected object, retrieving additional, historic data as needed in the method 110. The object analysis function 10 may perform a basic analysis of the current data (block 113) for display in the object data section 76.

If the analyze button 766 is selected, the object analyze webpage 90 may be generated and displayed (block 114). The object analysis function 10 receives a sample matrix selection (block 115). The object analysis function determines if any temporal limits are set (block 116). If set, the temporal limits are received (block 117). The object analysis function 10 may retrieve contaminant readings for the selected object (block 118). The contaminant readings retrieved are limited by the temporal limits, if set.

A selected screening query is received (block 119). If a regulatory/governmental standard or limit, a selected standard/limit is received (block 120). If a user-defined standard or limit, a user-defined standard/limit is received (block 121). The user-defined standard may be a user-entered contaminant concentration (e.g., in µg/L). The object analysis function 10 receives a selected analyte for the comparison (block 122). The object analysis 10 performs detailed analysis comparing the selected analyte concentration data from the selected sample matrix to the selected or user-defined standard/limit over the time period defined per the temporal limits (block 123). After calculating, the object analysis function 10 displays the comparison results (block 124) as described above. The display step may include displaying the results in chart 106 and/or downloading to a spreadsheet file.

With reference again to FIG. 5a and the object data section 76, the field testing tab displays field testing data about the selected object. Field testing data will only be applicable for specific objects such as monitoring wells, soil borings, and other sampling points. Using monitoring wells as an example, field testing information that are available preferably includes gauging date, time and method, depth to water depth of well, water elevation and corrected elevation. By selecting a gauging date, field information for that object will be displayed. The analytical tab presents analytical information about the selected object. The analytical tab preferably displays information such as matrix, date, analyte name, concentration and standard laboratory flags. By selecting the type of matrix (i.e., soil or groundwater) and a date, the results of that sampling date will be displayed. The analytical tab will show the analytes that were analyzed and the concentration of each analyte along with its corresponding laboratory code (i.e., U=not detected, J=estimated). The object analysis function 10 may perform the analysis of data received from the selected object to provide this data.

Figure 6:
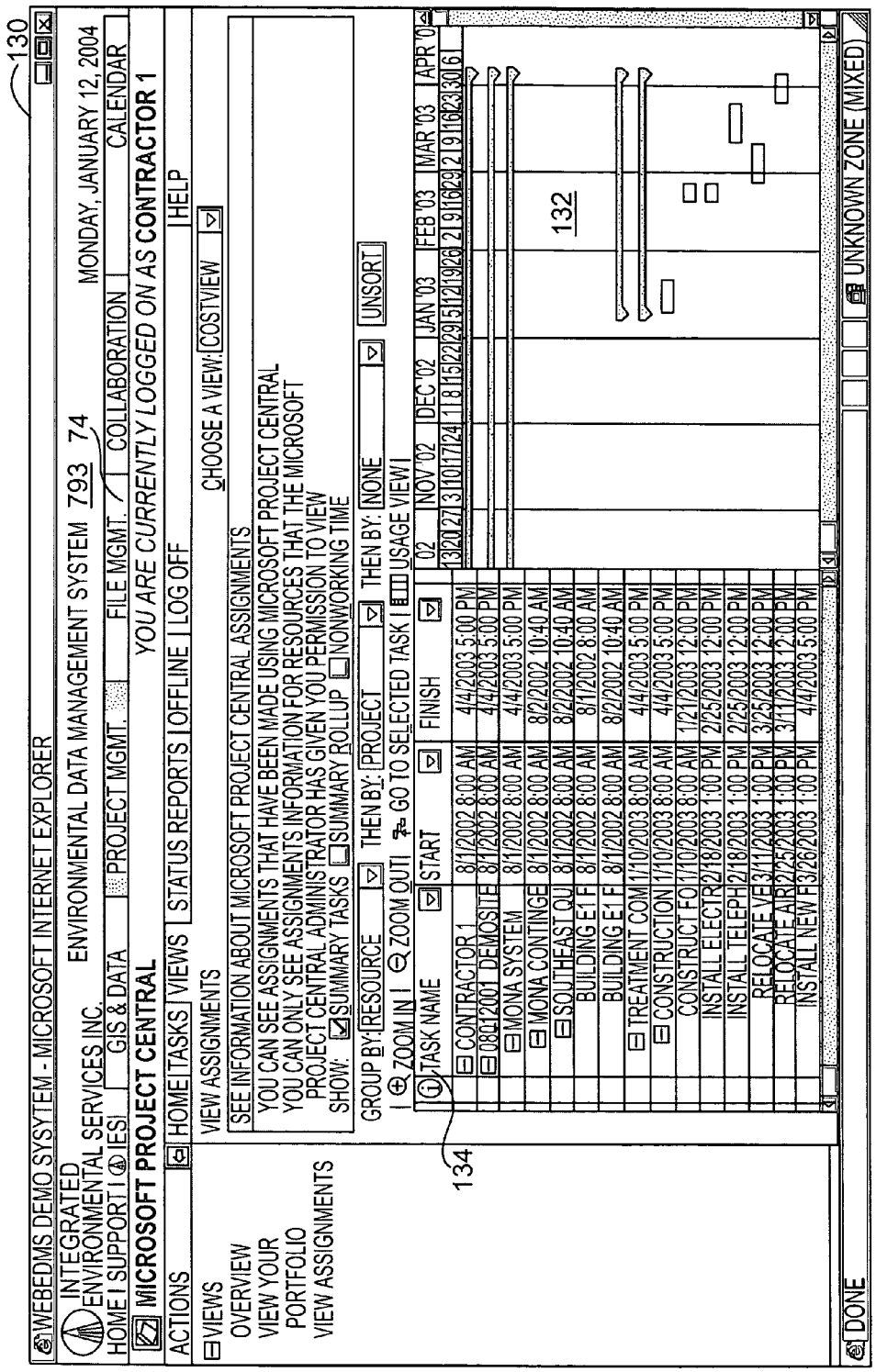
FIG. 6 is a screen shot illustrating an interface for a project management element of an embodiment.

With reference now to FIG. 6, shown is a screen illustrating an exemplary project management webpage 130. The project management webpage 130 may simply be the central webpage 70 displaying options provided by the project management element 18. As such, the project management webpage 130 preferably includes the module tab section 84. The project management webpage 130 may be accessed by selecting a project management tab 743.

The project management element 18 is preferably based on Microsoft® Project Central. The project management element webpage 130 may include an assignment task lists section 134 and gantt chart section 132 displaying the duration of each task in a gantt chart format. The assignment task list section 134 preferably displays the tasks assigned to the current team member that has logged into the system, in this case, Contractor 1. The assignment task list 134 displays information about each specific task such as task name, start time and end time as well as percentage complete, and actual work complete. The assignment task list section 134 may also include other sections such as obtaining status reports of tasks from the various project team members. Other functions available in the project management element 18 are similar to what is normally available in the Microsoft® Project Central application.

Figure 7:
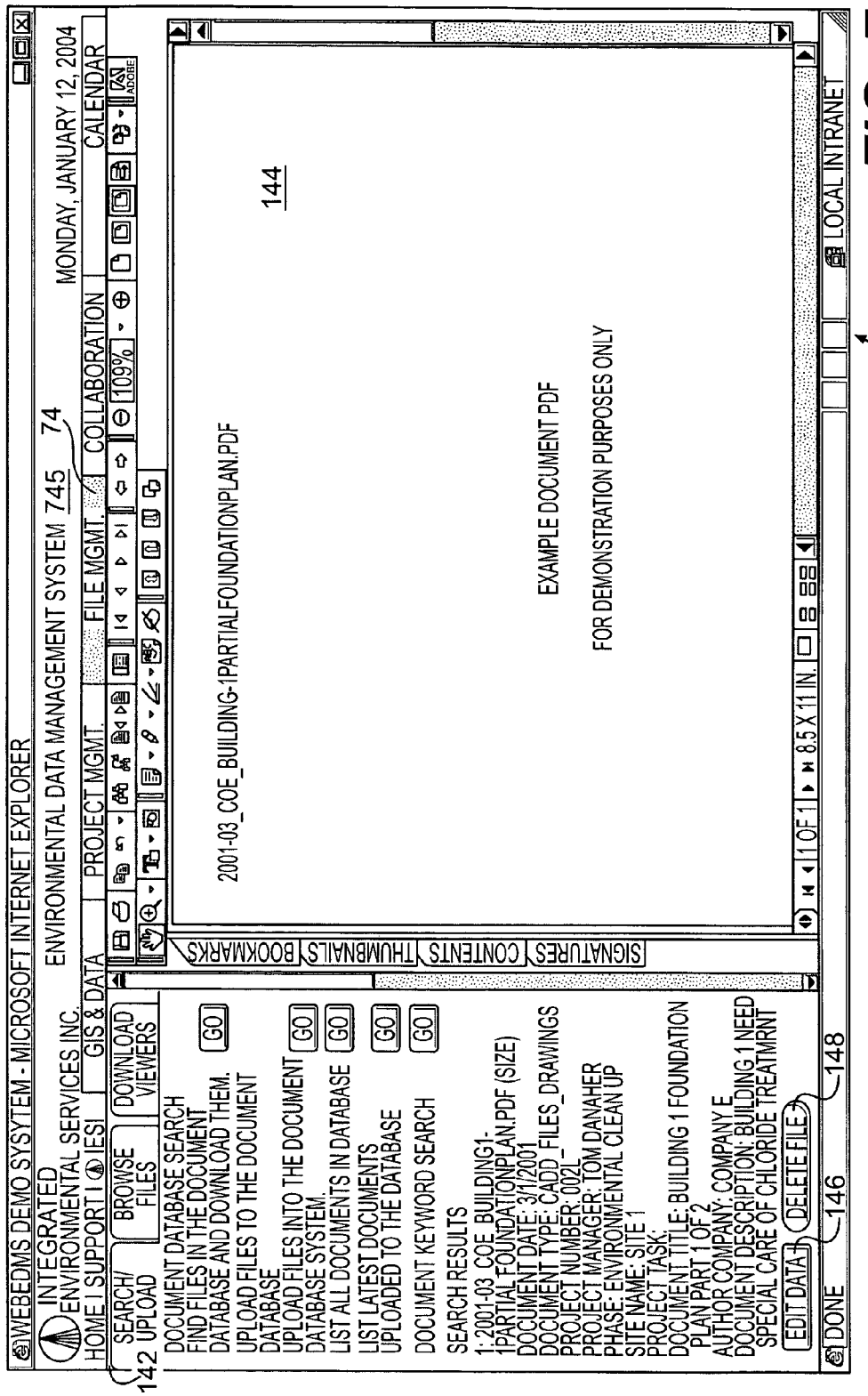
FIG. 7 is a screen shot illustrating an interface for a file management element of an embodiment with various ways to search and retrieve files.

With reference now to FIG. 7, shown is a screen illustrating an exemplary file management webpage 140. The file management webpage 140 may simply be the central webpage 70 displaying file management element 16 options. As such, the file management webpage 140 preferably includes the module tab section 84. The file management webpage 140 may be accessed, for example, by selecting a file management tab 745 or selecting the documents button 764 in the object data section 76. The file management webpage 140 preferably also includes a file management section 142 and a document display section 144.

The file management section 142 preferably includes selectable tabbed listings corresponding to options provided by the file management element 16. The file management section 142 includes tabs for searching/uploading of document files, browsing document files and downloading viewers. The search/upload tab preferably includes "go" buttons for searching a document database (e.g., on the file server 56), uploading files to the document database, listing all documents in the document database, listing latest uploaded documents, and performing a keyword search of all the documents in the document database. The file management section 142 preferably includes a search results area that displays the results of the document search or the document lists. The search function of the file management function allows the documents to be searched in a variety of ways including by date range, author company, title, type, and description to name a few. In addition, the search function has an advanced feature that is able to search for keywords within files and documents obtained through optical character recognition (OCR) technology and return the results in the results area.

The file management section 142 also preferably includes an edit data button 146 and a delete file button 148. Selecting the edit data button 146 allows document data (e.g., name, type, related project information, author, document description, etc.) to be edited. Selecting the delete file button 148 deletes the document and its record from the document database. In order to edit information pertaining to a document, a user may be required to have the necessary login privileges as part of the security measures in place to protect the integrity of the data.

The document display section 144 displays a document found as a result of a document search or selected from the document lists in the file management section 142. Preferably, the documents in the document database are in portable document format (pdf) format and the document display section 144, therefore, preferably incorporates a pdf viewer.

The file management section 142 shown allows selection of an upload function that will allow authorized users the ability to upload documents directly to the database. Uploading documents to the database may require certain security privileges as well. Once a document has been uploaded, it is immediately available to the rest of the project team. The document file name is automatically created based on the creation date and the author company. By automatically creating unique file names using a standard naming convention, the documents are easy to organize and avoid duplicate file names.

The browse files tab function allows the documents to be searched via a directory tree structure. Documents are organized in folders in the tree structure and can be viewed in the document display section 144 by clicking on the document. The download viewer tab preferably provides links to download third party viewers used to display the documents correctly in their native format within the browser window.

Figure 8:
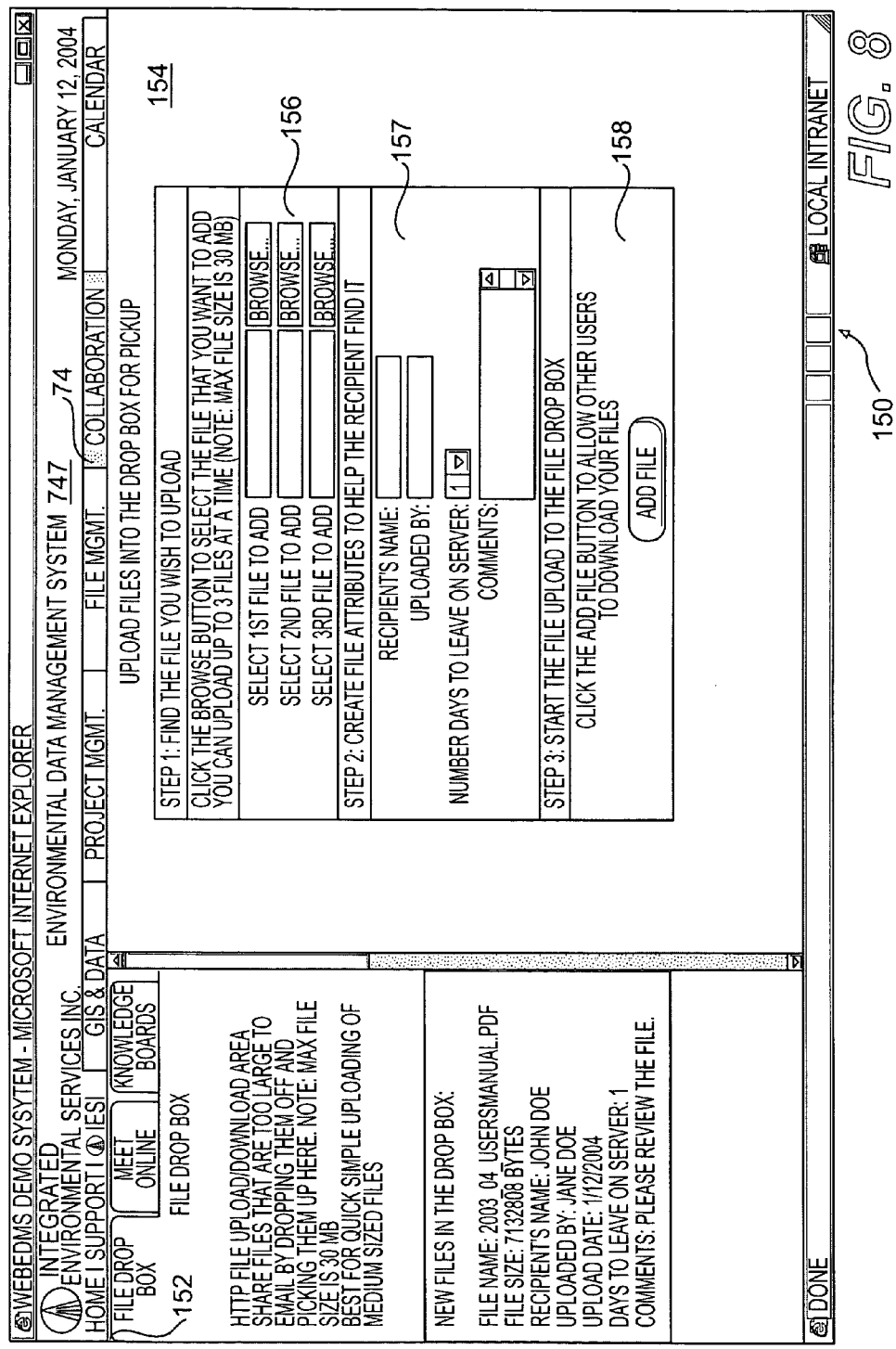
FIG. 8 is a screen shot illustrating an interface for a collaboration element of an embodiment where team members can upload files to share with others.

With reference now to FIG. 8, shown is a screen illustrating an exemplary collaboration webpage 150. The collaboration webpage 150 may simply be the central webpage 70 displaying collaboration element 20 options. As such, the collaboration webpage 150 preferably includes the module tab section 84. The collaboration webpage 150 may be accessed, for example, by selecting a collaboration tab 747 on the central webpage 70. The collaboration webpage 150 preferably also includes a collaboration menu section 152 and a menu display section 154.

The collaboration menu section 152 includes selectable tab listings corresponding to options provided by the collaboration element 20. The collaboration menu section 152 includes a file drop box tab, meet online tab and knowledge boards tab. The file drop box tab provides an option for project team members to transfer and share temporary files such as working copies or draft files. Selection of the file drop box tab displays a new files drop box section and an upload files section in the menu display section 154. In the upload files section, there are three subsections in order to upload a file. The select file section 156 allows the user to select a file to upload to the drop box. The user may select up to three files to upload. In the file attributes subsection 157, attributes can be included to the uploaded files to make it easier for other project team members to locate and pick up shared information. The upload file subsection 158, will begin the upload file process. Once the files have been successfully uploaded, each file and its corresponding attributes will appear in the new files drop box section.

The meet online tab preferably provides a link to an online meeting service provider. This link can be used by project team members to start setting up an online meeting session. The knowledge boards tab preferably provides forums to project team members so that they can share project knowledge with each other. Forums can be set up for different topics and team members can post or reply messages for each topic in the forum. Posting and replying to messages in a forum setting facilitates project coordination as the discussions can be followed on any of the topics.

Figure 9:
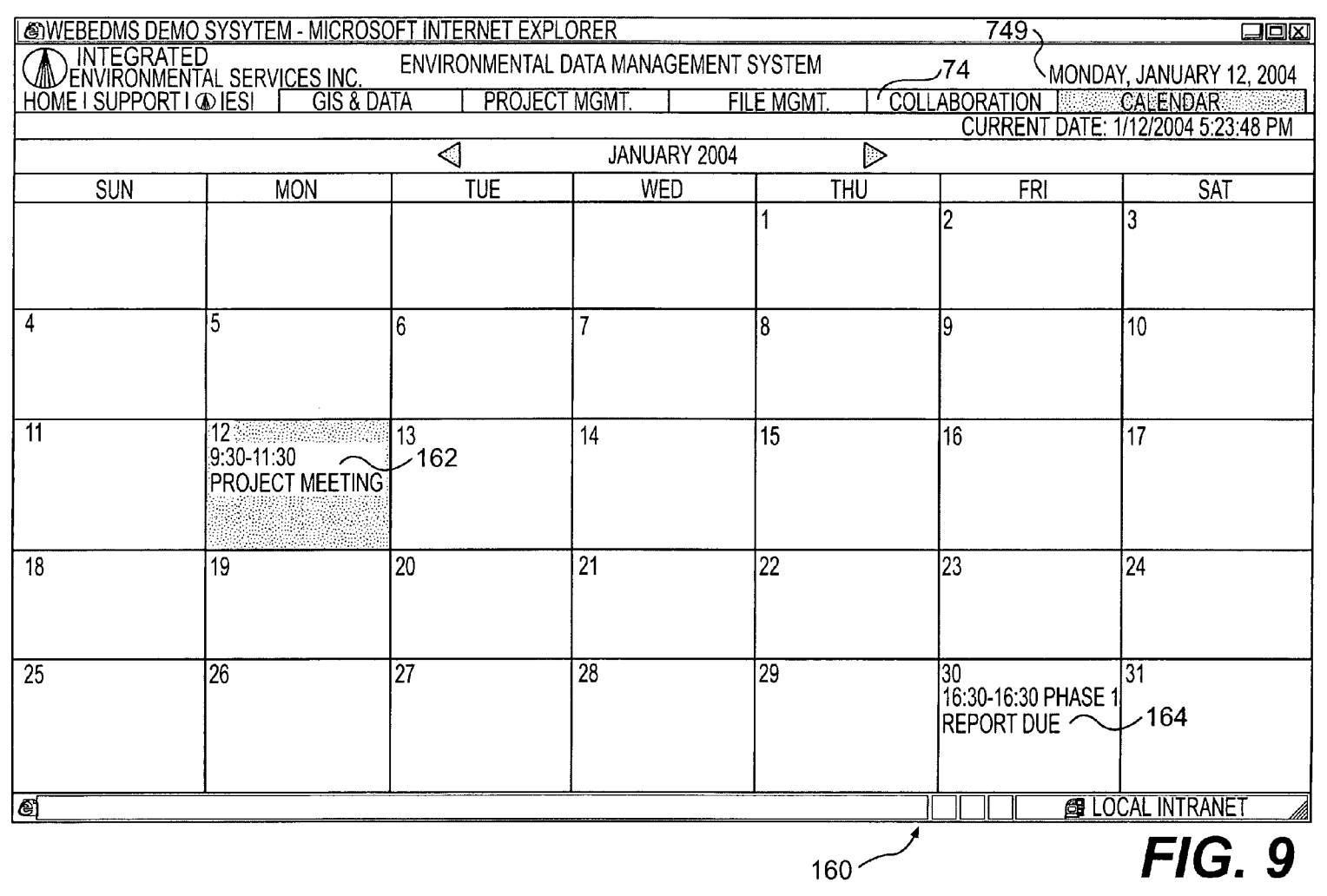

With reference now to FIG. 9, shown is a screen illustrating an exemplary calendar 160. The calendar 160 may simply be the central webpage 70 displaying calendar element 22 options. As such, the calendar 160 shown includes the module tab section 84. The calendar 160 may be accessed, for example, by selecting the calendar tab 749.

The calendar element 22 provides a means to highlight milestones, and a simple way to share meeting schedules among team members 162 or keep track of project deadlines 164. The calendar 160 preferably displays the current month and has forward and backward arrows to move from month to month. Calendar items such as appointments, meetings and project deadlines can be added by clicking on the date in the upper left corner of the date box. Items added to the calendar 160 will preferably cause the calendar element 22 to generate an email that will be sent to the project team members involved in the item.

Figure 10A:
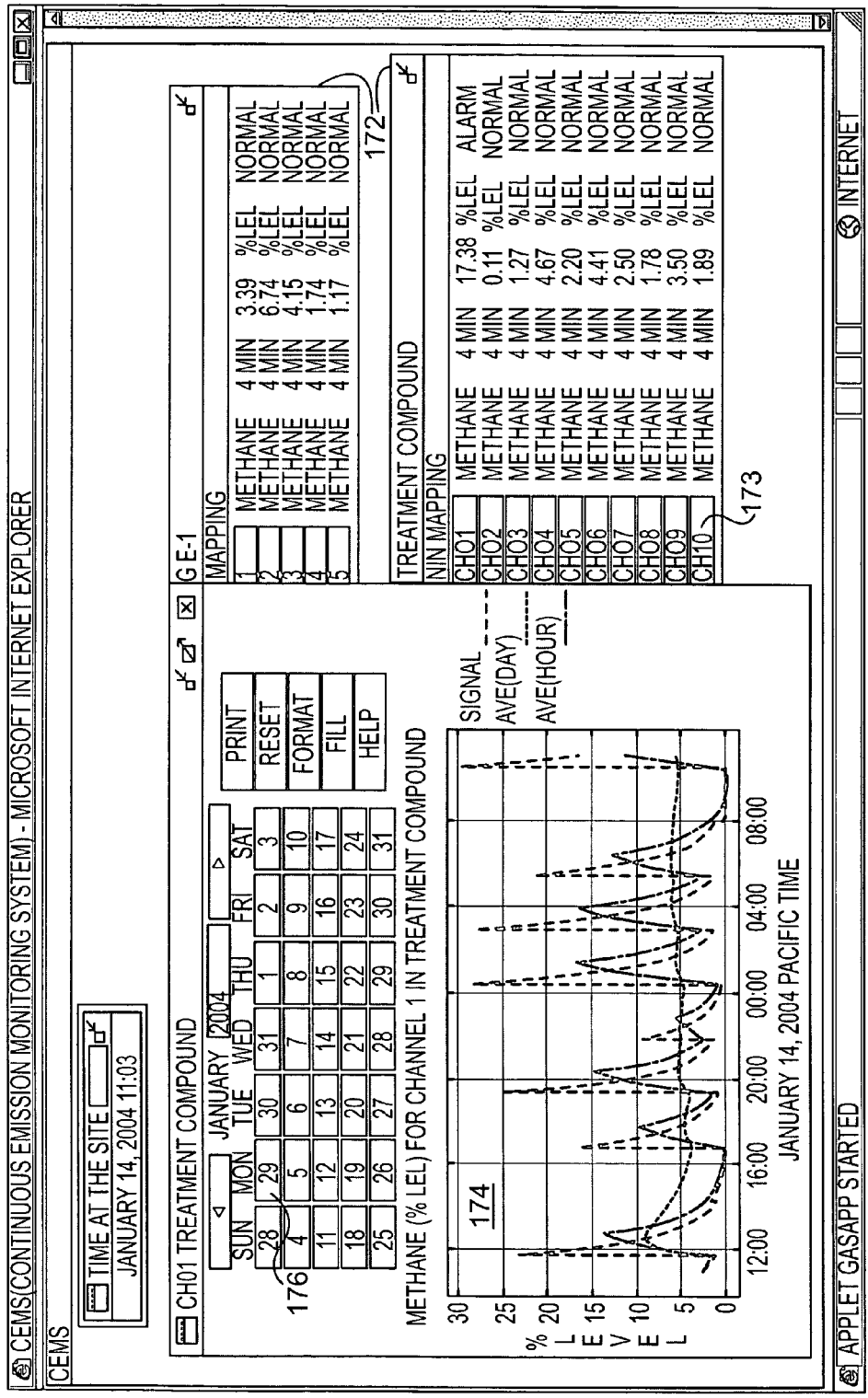
FIGS. 10a–b are screen shots illustrating an interface for a remote monitoring system that receives data continuously through sensors transmitting data in real-time.

With reference now to FIG. 10a, shown is a screen illustrating an exemplary webpage 170 to the continuous monitoring system 39. The continuous monitoring system 39 may be accessed by selecting the RMM button 860, which causes the webpage 170 to be displayed. In this example, the continuous monitoring system 39 is monitoring the presence of methane remotely through a site monitoring system 36 that includes methane sensors located strategically around individual buildings. The data readings collected continuously (i.e., the continuous live data update 38) by the sensors are preferably recorded electronically at the time of collection and stored directly into the central database 30. The data is available immediately over the network (i.e., LAN/WAN or Internet/Intranet) for analysis and reporting.

The continuous monitoring system webpage 170 shown in FIG. 10a displays the current time at the site and a separate window 172 for each building at the site where monitoring sensors have been installed. Each window 172 may display the name of the chemical (e.g., methane) or other COPC, the percentage of the lower explosive limit (LEL) for that chemical and a status column for each monitoring sensor in the building. The status will preferably change from "Normal" to "Alarm" when a chemical is detected at ten percent of its corresponding LEL. Specific information about an alarm for a specific sensor can be obtained by clicking on the sensor corresponding to the alarm. A new window 173 including a chart 174 containing the current reading, hourly average, and daily average and a calendar 176 may be displayed by selecting one of the sensors in a window 172. The calendar 176 enables display of the historical activity for the selected sensor.

Figure 10B:
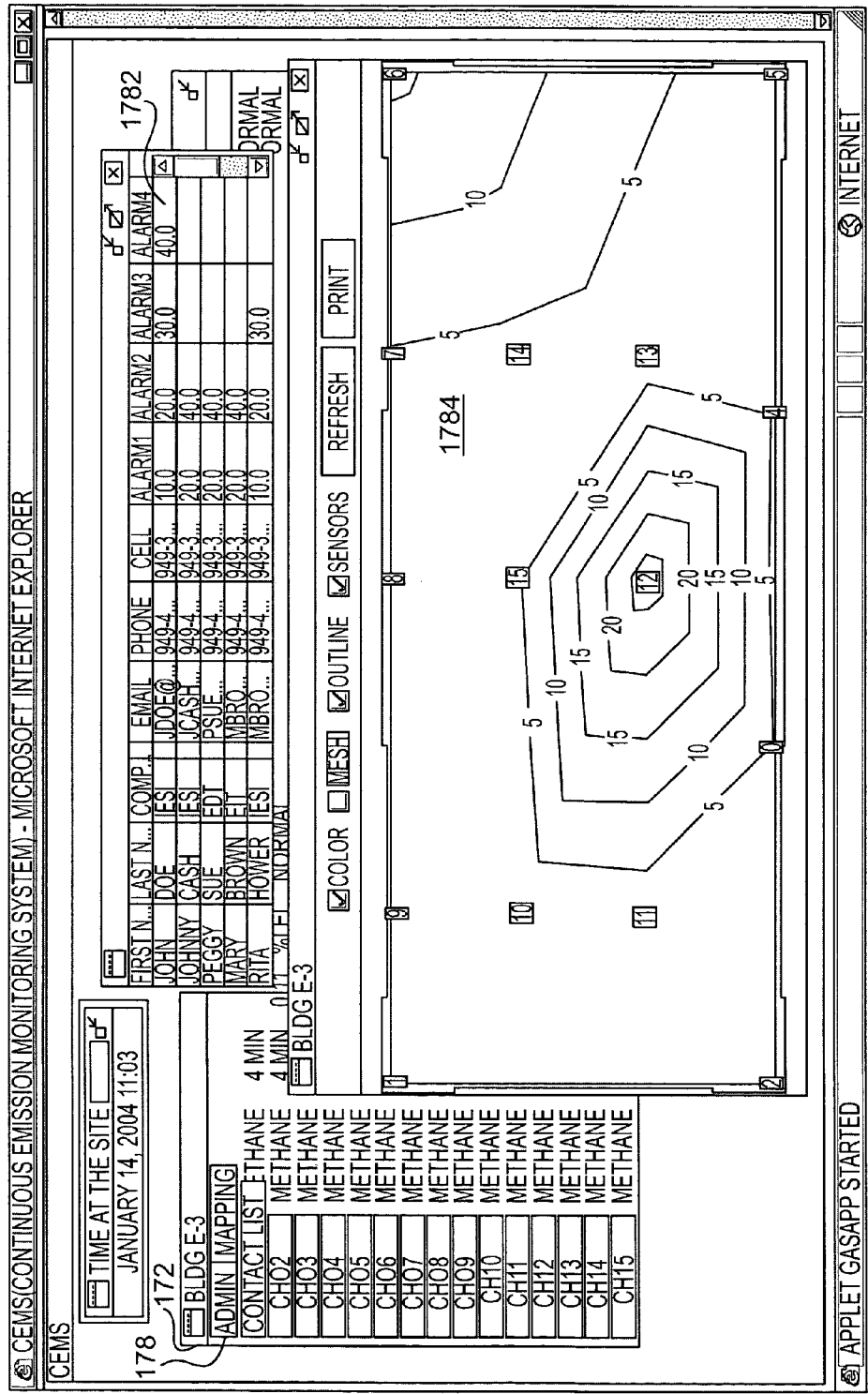

With reference now to FIG. 10b, the window 172 includes a menu 178. The menu 178 provides access to a contact list 1782 and a contour map 1784 for the building. The contact list 1782 preferably includes the contact names of the people that will need to be contacted should a problem arise. The system 5 (e.g., the collaboration element 20) will preferably email or send a text message via cell phones to the individuals on that list in the event an alarm is triggered. This will allow the contacts to monitor the site situation real-time via the Internet and take appropriate measures to prevent any potential crisis. Accordingly, the continuous monitoring system 39 may be used in a homeland security embodiment to monitor and provide alerts for detected chemical, biological, radiological, etc., concerns.

In addition to charting individual sensors (see chart 174), the sensor data within a building can be used to generate a contour map 1784 to quickly identify hot spots or potential problem areas. The contour map is preferably color coded to display the areas where there are high levels of concentration of a particular chemical (i.e., methane in this example).

With reference now to FIG. 11a, shown is a screen illustrating exemplary types of analysis that can be performed on the entire site on the central webpage 70. The central webpage 70 shown in FIG. 11a includes a data comparison section 182, a select date time duration section 184, a data-standards/limits comparison section 186, a comparison results key section 188, and the GIS map 72, (i.e., a spatial data comparison section). These sections and the corresponding comparisons are preferably accessed and displayed on the central webpage 70 through selection of the analysis manager ("AM") tab 862. The site analysis function 12 of the analysis module 8 preferably performs the data comparisons.

The data comparison section 182 preferably enables a user to enter temporal limits on a query that will cause the analysis module 8 to compare environmental data temporally and display the results of the comparison. The data comparison section 182 shown includes a sample matrix pull-down menu 183, and a display top analyte pull-down menu 184. The sample matrix pull-down menu 183 enables selection of a sample matrix for the temporal data comparison. The sample matrix allows the user to select in which medium to do the comparison (e.g., groundwater (WG), soil (SO) or soil gas (SG)). The display top analyte pull-down menu 184 enables selection of a limit on the number of analyte readings displayed according to the selected sample matrix. An analyte is a contaminant that the analysis module 8 has determined, preferably from the environmental data in the central database 30, is present at the site. In this embodiment, only the top analyte concentration readings up to the selected limit will be displayed.

The select data time duration section 185 enables selection of a time period for the temporal comparison. Preferably, the select data time duration section 185 includes a start-date text box, an end-date text box, and an exclude non-detect samples check box. The time duration section 185 can be left blank, in which case there will be no temporal limit placed on the comparison.

The site analysis module 12 preferably compares contaminant readings, on a per site basis, over the selected time period, according to the selected sample matrix and displays the top analyte concentration readings, as limited by the selected limit. If the exclude non-detect samples check box is checked, these temporal comparison results exclude non-detect samples. Non-detect samples are samples with detection limits that are not known.

The data-standards/limits comparison section 186 shown in FIG. 11*a*, enables a user to enter a query comparing an analyte to a regulatory standard, a user-defined standard, or some other limit. The data-standards/limits comparison determines whether the detected analyte is below, at or above the standard or limit, on an entire site basis. The data-standards comparison section 186 preferably includes a select screening query pull-down menu 1860, a standard/limit selection pull-down 1862, an analyte selection pull-down menu 1864 and a display results pull-down menu 1866. The select screening query pull-down menu 1860 preferably enables the selection of the type of comparison (e.g., method and analyte, analyte, analyte to regulatory standard, analyte to user-defined standard). The comparison selection shown in FIG. 11*a* is an analyte to regulatory standard comparison.

The standard/limit selection section 1862 varies according to the type of comparison selected. With the analyte to regulatory standard comparison selected, as shown in FIG. 11*a*, section 1862 may be a pull-down menu enabling selection of a specific regulatory standard for the comparison. If the analyte to user defined standard comparison is selected, the standard/limit selection section 1862 may be a text-box in which the user can define concentration levels (e.g., in μg/L) (see, e.g., FIG. 11*b*). This user-defined standard function allows users to contemplate results of relaxed regulation or analysis based on higher standards than those set by the regulatory agencies. Sometimes, standards for a given site may be negotiated higher than the regulatory standards.

The analyte selection pull-down menu 1864 enables selection of the analyte to be compared. The analytes listed in the pull-down menu 1864 are determined from the site's environmental data. The display results pull-down menu 1866 preferably enables the selection of a limit on the displayed results (e.g., analyte concentration greater than standard, less than standard, all). The data-standard/limits comparison section 186 preferably includes a go button that is selected by the user to initiate the comparison.

The results of the data-standard/limit comparison are preferably displayed on the GIS map 72. Specifically, if compared on a per entire site basis, then all the objects 720 that have detected the selected analyte are displayed or otherwise highlighted on the GIS map 72. If a top analyte limit or temporal limit is selected in the temporal comparison section, then the results of the data-standard/limit comparison will be so limited. For example, the GIS map 72 may display only the objects 720 detecting the top analyte results or otherwise highlight these objects 720.

With continued reference to FIG. 11*a*, the comparison results key section 188 shown includes a color key 1880 that indicates with different colors which objects detected concentrations of the selected analyte below, at or above the standard/limit. Preferably, the key assigns a color for each of these levels and the objects 720 displayed on the GIS map 72 are colored accordingly. Further, only the names of those objects 720 that meet the selected limit (e.g., greater than the standard) are displayed on the GIS map 72, as shown in FIG. 11*a*. As a result, the GIS map 72 enables a spatial comparison of the location of readings of the selected analyte on the site, and the levels of these readings. In this manner, the GIS map 72 is a spatial comparison section.

With reference now to FIG. 11*b*, the comparison results key section 188 also includes a view chart button 1882 and a download results file (e.g., Microsoft Excel® spreadsheet file) button 1884. The view chart button 1882 may be selected to trigger the display of a chart 1886 graphically indicating the results of the data-standard/limit comparison. As shown, the chart 1886 depicts the objects with the top-five concentrations of the selected analyte, with the amount of each concentration, and the amount of a user-defined standard-allowed concentration. The chart 1886 may also color-code the concentration results shown per the color key 1880. The download results file button 1884 may be selected to download a file with the results of the comparison. Preferably, the results are downloaded into a spreadsheet file.

Figure 11C:
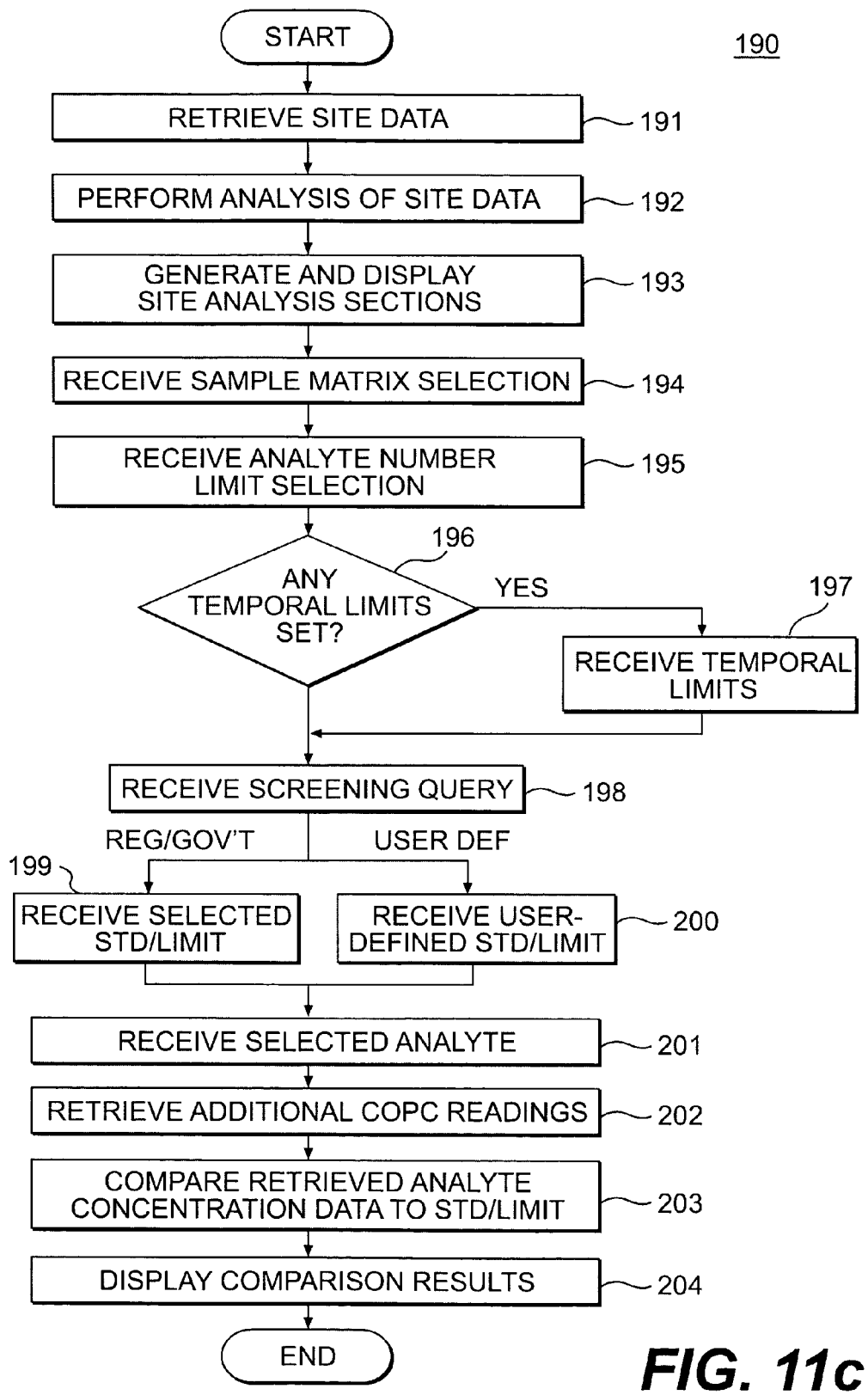
FIG. 11c is a flowchart illustrating an embodiment of a site analysis method.

With reference now to FIG. 11*c*, shown is a flowchart illustrating an exemplary site analysis method 190. The site analysis method 190 shown includes steps performed by the site analysis function 12 as described herein with reference to FIGS. 11*a* and 11*b*. The site analysis function 12 retrieves site data for the current site, preferably from the central database (block 191). The site analysis function 12 may retrieve the site data when the central webpage 70 is displayed or in response to selection of the analysis button 862. The site analysis function 12 may only retrieve current data for the site, retrieving additional, historic data as needed in the method 190. The site analysis function 12 may perform a basic analysis of the current data (block 192) for display in the site data section 74.

If the analysis button 862 is selected, the site analysis sections 172–178 may be generated and displayed (block 193), e.g., on the central webpage 70. The site analysis function 12 receives a sample matrix selection (block 194). An analyte number limit selection may be received (block 195), based on a selection in the display top analyte pull-down menu 1722. The site analysis function 12 determines if any temporal limits are set (block 196). If set, the temporal limits are received (block 197).

A selected screening query is received (block 198). If a regulatory/governmental standard or limit, a selected standard/limit is received (block 199). If a user-defined standard or limit, a user-defined standard/limit is received (block 200). The user-defined standard may be a user-entered contaminant concentration (e.g., in μg/L). The site analysis function 12 receives a selected analyte for the comparison (block 201). The site analysis function 12 may retrieve additional contaminant readings in the sample matrix for the selected analyte (block 202), limited by the analyte number limit and the temporal limits, if any. The site analysis function 12 compares the retrieved analyte concentration data to the selected or user-defined standard/limit (block 203). After calculating, the site analysis function 12 displays the comparison results (block 204) as described above. The display step may include displaying the results in the GIS map 72, on a chart 1886 and/or downloading to a spreadsheet file.

With reference now to FIG. 12*a*, shown is a screen illustrating an exemplary 3D display webpage 210. The webpage 210 preferably includes a 3D display section 216, a display control 212, a find chemicals (or other contaminants) section 214, a chemical data section 218, a pipe analysis section 220, and a data export section 222. The 3D display section 216 includes a 3D display 2166 of the extent and characteristics of the contaminant concentration and a number of viewing options 2160.

The viewing options 2160 include: a pan tool, which enables the user to pan around the site, viewing the 3D display 2166 from different angles; a z-axis tool, which enables the user to exaggerate the z-axis of the 3D display; a sample period tool, which enables the user to decide data from which sample period to analyze, dynamically causing the 3D display 2166 to show the changes in the extent and characteristics of the contaminant concentration over time; a select area tool, which enables the user to select a ROI (e.g., by dragging and clicking to define a user-defined polygon in the 3D display); a reset tool, which enables the user to reset to the default view of the 3D display 2166; and a print tool, which enables the user to print the 3D display. An example of a ROI is illustrated by the cross-hatched area in FIG. 12a.

With continued reference to FIG. 12a, the display control 212 preferably enables the user to toggle the display of contaminants, wells (or other site monitoring systems), soils, pipes and other structures or substances on the 3D display 2166. For example, the display control 212 preferably includes a chemical checkbox 2120, a wells checkbox 2122, a soils checkbox 2124, a pipes checkbox 2126 and a groundwater checkbox 2128. Only those items checked on are displayed on the 3D display 2166. If the chemical checkbox 2120 is toggled on, then checkbox(es) for the chemical(s) selected in the find chemicals section 214 are displayed. In the example shown, the chemical selected is benzene, and the benzene checkbox is toggled on.

The find chemicals section 214 preferably enables the user to select the chemical(s), or other contaminant(s), that will be displayed on the 3D display 2166. Accordingly, the find chemicals section 214 preferably includes a chemical text box 2142 in which the selected chemical can be entered. The find chemicals section 214 may also include a browse button that enables the user to select the chemical(s) from a pop-up list of chemicals. The find chemicals section 214 may also include a media button 2140 that enables the user to select the media type (e.g., soil, groundwater), a display pipes button 2146 to toggle display of pipes in the 3D display 2166 and a "Go" button 2144 which initiates the display of the extent and characteristics of the selected contaminant concentration.

The chemical data section 218 preferably includes a chemical (or other contaminant) data tab 2180 and a pipe data tab 2182. The chemical data tab 2180 preferably lists the computed mass, volume, and impact area of sub-surface (or above-surface for air) contamination of the selected chemical(s) or other contaminant. As discussed above, the 3D viewer module 24 preferably performs this computation. If a ROI is selected, the chemical data tab 2180 preferably displays the computed mass, volume, and impact area of sub-surface (or above-surface for air) contamination of the selected chemical(s) or other contaminant in the ROI only. The pipe data tab 2182 preferably displays associated information for each pipe segment such as manufacturer, type of pipe, material, length, installation date, diameter, depth below ground, etc.

With continuing reference to FIG. 12a, the pipe analysis section 220 preferably includes a pipe document button 2200, a pipe maintenance button 2202 and a pipe budget button 2204. The pipe document button 2200 preferably provides access to a file management webpage 146 for pipe documents. The pipe maintenance button 2202 preferably provides access to a webpage displaying pipe maintenance data. The pipe budget button 2204 preferably provides access to a webpage displaying pipe budget data.

The data export section 222 preferably enables export of the chemical or other contaminant computation results (from the chemical data tab section 2180) to the risk assessment module 26 and/or the remediation module 28. Accordingly, the data export section 222 preferably includes a export to risk assessment button 2220, that is selected to export the computation results to the risk assessment module 26 and an export to remediation technology button 2222, that is selected to export the computation results to the remediation module 28.

With reference to FIG. 12b, shown is a 3D display visualizing the extent of a color-coded chemical (e.g., benzene) plume 224 below the ground surface. The extent of the chemical plume is determined by the ROI (see FIG. 12a). The 3D viewer module 24 may calculate the size and the characteristics of the plume and generate the 3D display from the chemical data tab 2180 computations. The color bar scale 226 is preferably used as a key to show the difference of concentration values in the plume.

With reference now to FIG. 13a, shown is a screen illustrating an exemplary risk assessment webpage 230. The risk assessment webpage 230 preferably provides access to the risk assessment functions performed by the risk assessment module 26. The risk assessment webpage 250 is displayed when the risk assessment button 866 or the export to RA button 2220 is selected. The risk assessment webpage 230 shown includes a site name pull-down menu 232, a job name pull-down menu 234, a ROI name pull-down menu 236, a media selection section 238, a COPC-selection section 240, a toxicity factors section 242, a receptor selection section 244, an exposure pathway selection section 246, a risk characterization section 248, a HQ threshold section 250, a ILCR threshold section 252 and a proceed button 254. The selections made on the risk assessment webpage 230 preferably provide site environmental, physical and biological data needed for performing screening level human health risk assessments according to methods and algorithms developed by the US EPA.

The site name pull-down menu 232 preferably includes a list of hazardous waste sites that the system 5 is monitoring. The user selects a site for performing the risk assessment, and the computations described above for the selected site are preferably used. The job name pull-down menu 234 preferably includes a list of job names for the selected site. A job is a discrete health risk assessment and/or cleanup criteria development project on the selected site. The user selects a job. The ROI name pull-down menu 236 preferably includes a list of ROIs defined for the selected site. The user preferably selects a ROI for the risk assessment, and the computations described above for the selected ROI are preferably used.

With continued reference to FIG. 13a, the media selection section 238 preferably provides a media menu and a media-type menu (e.g., pull-down menus). The media menu includes a list of media (e.g., soil, surface water, groundwater, ambient air) in the selected site or ROI. The media-type menu includes a list of specific types of selected media. For example, if soil is the selected media, silt, clay, silty-clay, sand etc., may be choices of the specific type of selected media. Some selected media will not have multiple corresponding specific types. The user selects a media and, if applicable, a specific type of media. The risk assessment is then performed for the selected media and specific type of media.

The COPC-selection section 240 enables the selection of which COPC(s) the risk assessment will be performed. The COPC's may be manually selected or automatically selected. Accordingly, the COPC-selection section 240 includes buttons (e.g., radio buttons) for electing to manual-select COPCs or electing automatically-selected COPCs, including, e.g., all-detected COPCs, COPCs with a maximum concentration greater than Industrial Preliminary Remedial Goal (Ind PRG) (Max Conc.>Ind. PRGs), and COPCs with a maximum concentration greater than the Federal Maximum Contaminant Levels (MCL) (Max Conc.>MCL). The COPC-selection section 240 also includes a COPC menu that includes a list of the COPCs for the selected site or ROI. If manual-selection is elected, then the user may select one or more COPCs from the COPC menu. The risk assessment will be performed on the selected COPCs. If any of the other buttons are selected, the COPCs for the risk assessment will be automatically selected. If all-detected COPCs is selected, then the risk assessment will be performed on all the detected COPCs. If Max Conc.>Ind. PRGs is selected, then the risk assessment will be performed on the COPCs that have a concentration exceeding the industrial preliminary remedial goal in the media. If Max Conc.>MCL is selected, then the risk assessment will be performed on the COPCs that have a concentration exceeding the federal maximum contaminant level.

With continuing reference to FIG. 13a, the toxicity factors section 242 enables the selection of the risk assessment algorithm. As described above, the risk assessment algorithm is preferably used by the risk assessment module 26 to process the site's or ROI's environmental data (e.g., the selected media, COPC, computed contaminant mass, volume, and/or area, etc.) to determine health risks and/or HBRGs for a selected receptor(s) and a selected pathway(s). Accordingly, the toxicity factors section 242 includes buttons (e.g., radio buttons) for selecting federal or state toxicity factors to use in the risk assessment algorithm. As such, the toxicity factor section 242 also includes state menu (e.g., a pull-down menu) that includes a list of the states, one of which that may be selected by the user if state toxicity factors are selected.

The receptor selection section 244 enables the selection of one or more receptors for the risk assessment or HBRG calculations. The receptor selection section 244 includes a receptor scroll menu. The receptor scroll menu includes a list of types of receptors. The user selects one or more receptors for the risk assessment. A receptor is any human or ecological component which is or may be affected by a contaminant from a contaminated site. See, e.g., "EPA Terminology Reference System," incorporated herein by reference.

The exposure pathway selection section 246 enables the selection of one or more pathways for the risk assessment. The pathway selection section 246 shown includes a pathway scroll menu. The pathway scroll menu includes a list of types of pathways. The user selects one or more pathways for the risk assessment. A pathway is the physical course a chemical or pollutant takes from its source to the exposed organism. See, e.g., "EPA Terminology Reference System."

With continued reference to FIG. 13a, the risk characterization section 248 enables the user to characterize the type of risk calculation. This characterization determines the type of output produced (e.g., risk output 261 or HBRG output 263 as shown in FIG. 1) and may limit or qualify the output. The risk characterization section 248 includes buttons (e.g., radio buttons) for selecting a HBRG output 263 or a risk output 261. The risk characterization section 248 also includes an environmental data statistical treatments menu. The environmental data statistical treatments menu includes selectable listings such as 95% upper confidence limit, average concentration and maximum concentration of selected COPCs; if a risk output 261 is selected, the risk is based on the selected statistical treatment of the data.

The threshold section preferably includes of the HQ threshold 250 and the ILCR threshold 252. The HQ threshold 250 includes a hazard quotient (HQ) threshold menu. The incremental lifetime cancer risk (ILCR) threshold 252 includes an ILCR threshold menu. The HQ threshold menu lists various HQ thresholds. The ILCR threshold menu lists various ILCR thresholds. These thresholds determine how the risks or HBRGs are calculated.

Once the above-described selections are made and the proceed button 254 is selected, a receptor parameter webpage 260 is displayed, as shown by the screen of FIG. 13b. (In alternative embodiments, receptor parameters are not viewed or changed and selection of the proceed button 254 causes the selected output (risk or HBRG) to be generated by the risk assessment module 26.) The receptor parameter webpage 260 enables the user to review receptor specific exposure parameters. The receptor parameter webpage 260 includes a receptor parameters section 262, a parameters key section 269, a return to previous step button 264, a make changes button 266, and continue button 268. The receptor parameters section 262 includes a list of the receptors selected on the risk assessment webpage 230 and the exposure parameter values for the selected receptors. The exposure parameters are default US EPA defined model exposure characteristics used for the selected receptors in the risk assessment. These default parameters may be stored in the central database 30. The parameters include carcinogenic and non-carcinogenic model characteristics. The parameters key section 269 includes a key for the parameter values in the receptor parameters section 262. The return button 264 returns the user to the risk assessment webpage 230. The make changes button 266 navigates the user to a modify receptor parameters webpage 260 as shown in FIG. 13c. The continue button 268 navigates the user to a risk (webpages 280–330) or HBRG report (webpages 350–370).

With reference now to FIG. 13c, if the user selects the make changes button 266 on the receptor parameters webpage 260, a screen illustrating a modify receptor parameters webpage 270 is displayed. The modify receptor parameters webpage 270 enables the user to modify the receptor exposure parameters. As such, the modify receptor parameters webpage 270 includes a receptor parameters section 272, a parameters key section 269, an accept changes button 274 and a cancel changes button 276. The receptor parameters section 272 includes a list of the selected receptors and the exposure parameter values as above, but lists the exposure parameter values in text boxes. As such, the exposure parameter values in the text boxes can be changed. The accept changes button 274 is selected to save any changes and return to the receptor parameter webpage 260. The cancel changes button 276 is selected to cancel any changes and return to the receptor parameter webpage 260.

If a risk output is selected in section 248 of the risk assessment webpage 230, then selection of the continue button 268 on the receptor parameter webpage 260 causes the risk assessment module 26 to perform a risk assessment that generates a preliminary risk report. With reference now to FIG. 13d, shown is a screen illustrating a portion of a first page of an exemplary preliminary risk report 280 generated by the risk assessment module 26 based on selections made on the risk assessment webpage 230. Specifically, the preliminary risk report 280 is a Receptor and Pathway specific HQ/ILCR report for COPCs at a site (e.g., "Carson Town Center"), for job "South Quadrant," in silt-type soil, for dermal contact and indoor air inhalation pathways, for commercial worker, construction worker, and residential adult receptors, using a 95% upper confidence limit of measured COPC concentrations, a HQ threshold of 1.0 E+0 and a ILCR threshold of 1.0 E-4. The preliminary risk report 280 includes a title section 282 and a HQ, ILCR risk calculation section 284.

The title section 282 lists the information describing the report 280, as described above. The risk calculation section 284 lists the receptor, the pathway, the COPC 2840, the COPC concentration (determined from the environmental data for the site or ROI) 2842, the HQ calculation 2844 and the ILCR calculation 2846. The risk calculation section 284 may include multiple pages. Accordingly, the preliminary risk report 280 may also include a section that indicates the page number of the risk calculation section 284 and the total number of pages and that enables navigation (e.g., one or more page navigation buttons (e.g., next page, previous page, last page, first page, etc.)) to the other pages of the risk calculation section 284.

Figure 13E:
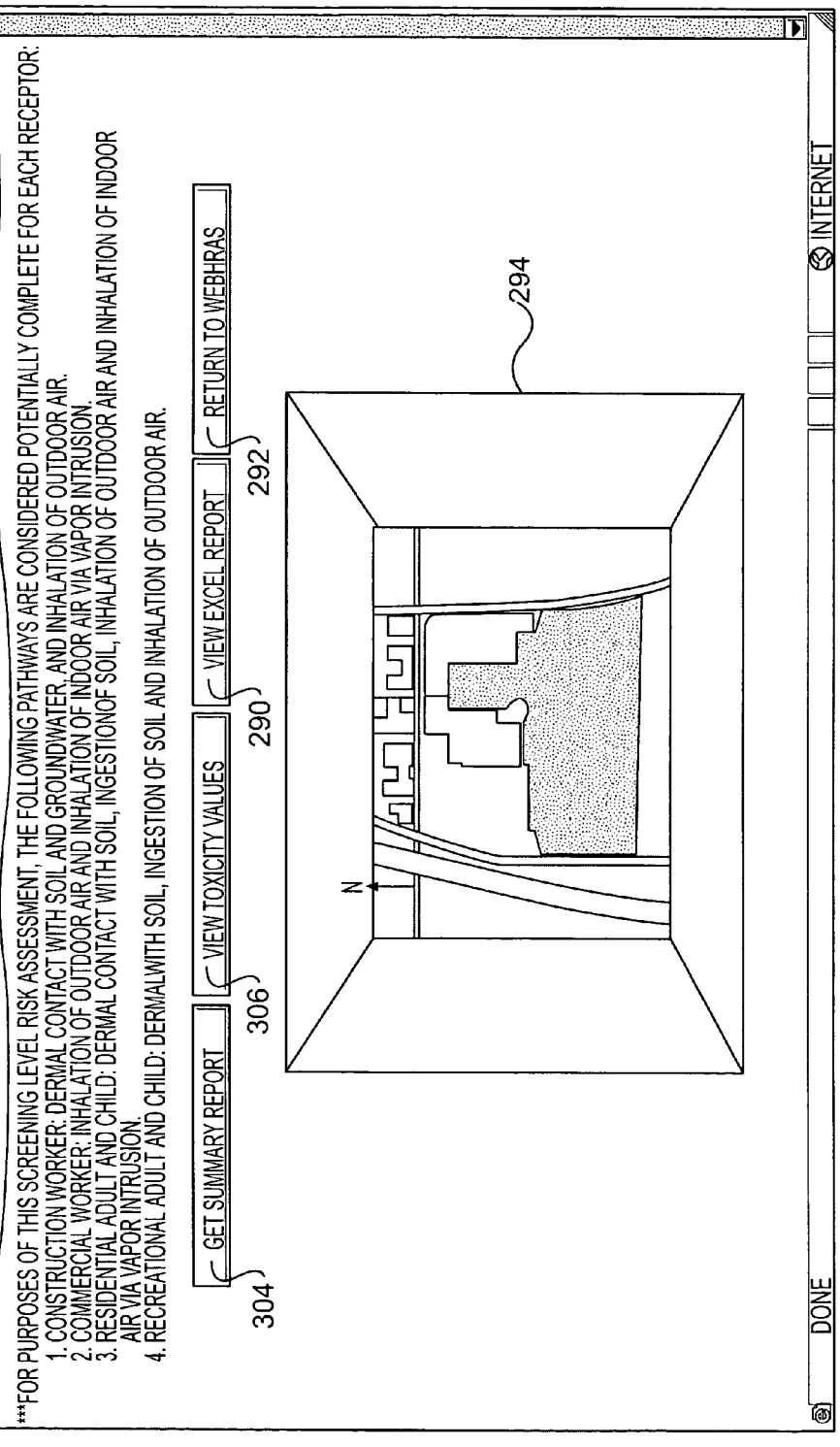

The preliminary risk report 280 shown includes a get summary report button 286, a view toxicity values button 288, a view Excel report button 290, a return to webHRAS button 292 and a map of the ROI 294 as defined in the 3D viewer module 24. The get summary report button 286 opens up an exemplary summary report webpage 300 as shown in FIG. 13e. The view toxicity values button opens up an exemplary webpage 320 as shown in FIG. 13g. Selection of the view Excel report button 290 displays the information in the risk calculation section 284 (see FIG. 13d) as a Microsoft Excel® spreadsheet format report 325 that can be downloaded as shown in FIG. 13h. The return to webHRAS button 292 causes a return to the risk assessment webpage 230.

With reference again to FIG. 13e, shown is a screen illustrating a portion of a first page of an exemplary summary risk report 300 generated by the risk assessment module 26 based on selections made on the risk assessment webpage 230. The summary report 300 summarizes the total risk by pathway for all COPCs shown in the risk calculation section 284 of the preliminary risk report 280. The summary risk report includes a title section 282, a report section 302, a return to preliminary report button 304, a view transaction log button 306, a view Excel report button 290, a return to webHRAS button 292 and a map of the ROI 294 as defined in the 3D viewer module 24.

The title section 282 includes the same information (other than the title itself) as the title section of the preliminary risk report webpage 280. The summary risk report section 302 preferably lists the receptors 3020, exposure pathways 3022, and COPCs 3024 selected. The summary risk report section 302 preferably also presents the chemical-, receptor- and pathway-specific hazard quotient 3026 calculated based on the user-identified site conditions (set on the risk assessment webpage 230 and described in title section 282). Lastly, the summary risk report presents the cumulative pathway-specific HQ 3028 and cumulative receptor-specific HQ 3030. Similarly, the incremental lifetime cancer risks (ILCR) derived from each COPC for each receptor and exposure pathway identified are calculated and summarized 3032 on webpage 300.

Figure 13F:
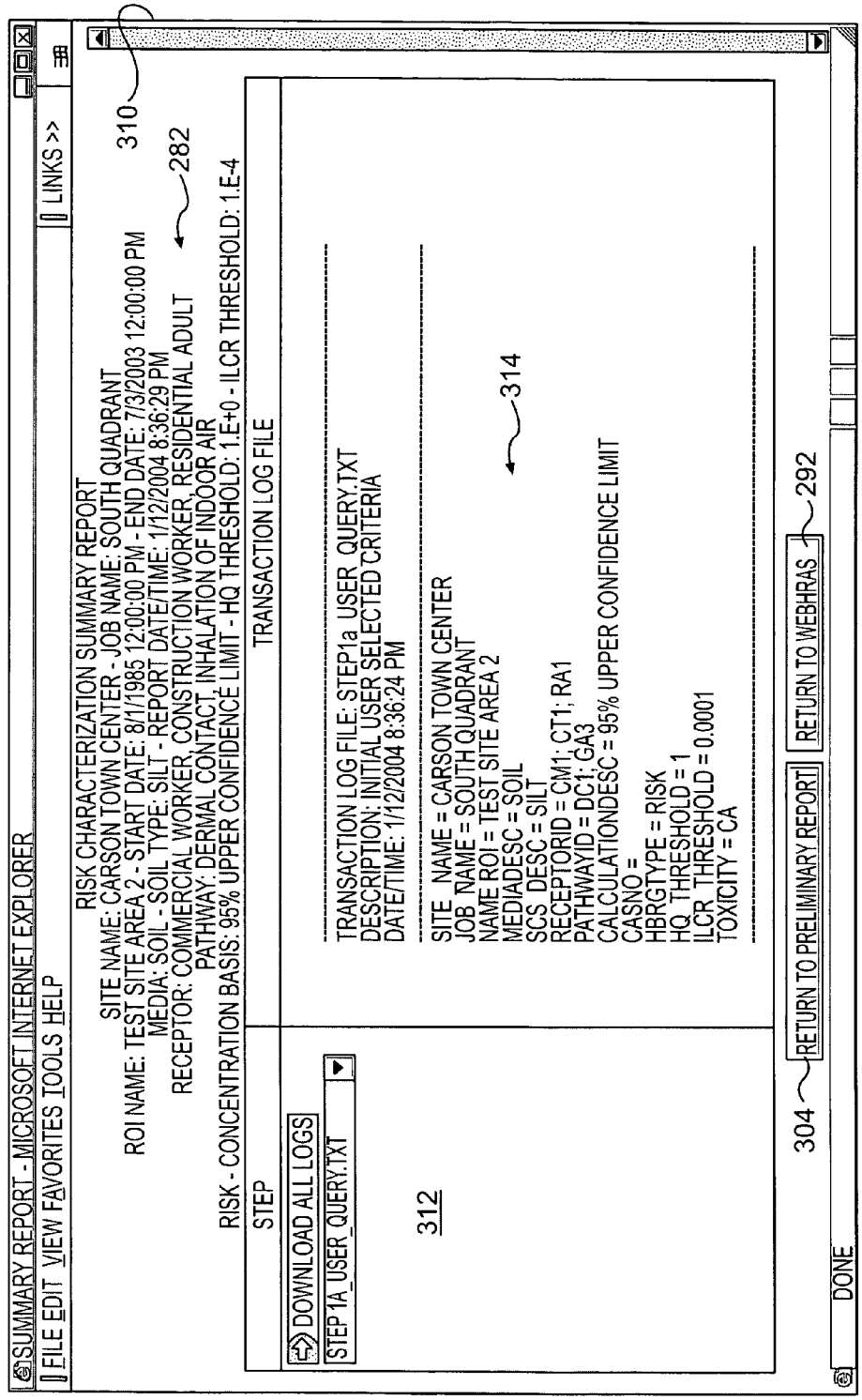

The view transaction log button 306 opens a new exemplary transaction log webpage 310 as shown in FIG. 13f. The transaction log webpage 310 includes the title section 282, a transaction step section 312 and the transaction log file section 314. The transaction step section 312 contains a pull down list of all the steps taken to reach the final risk calculation. By selecting a step, the transaction log file for the corresponding step will be displayed in the transaction log file section 314. For QA/QC purposes, the transaction log file preferably contains all the input parameters and calculations that were performed to arrive at the final risk calculation. The transaction log webpage also includes a return to preliminary report button 304 to return the user to the preliminary report webpage 280, and a return to webHRAS button 292 to return the user to the risk assessment webpage 230.

With reference again to FIG. 13e, the view Excel report button 290 preferably displays the information in the report section 302 in a Microsoft Excel® spreadsheet report that can be downloaded. The return to webHRAS button 292 will preferably go back to the risk assessment webpage 230.

The toxicity values used report 320 as shown in FIG. 13g includes a title section 282, a report section 322, a return to preliminary report button 304, a view Excel report button 290, a return to webHRAS button 292 and a map showing the ROI 294 as defined in the 3D viewer module 24. The toxicity value used report 320 displays the toxicity values for each COPC and receptor/pathway based on the selection of the toxicity factors section 242 in the risk assessment webpage 230. The title section 282 includes the same information (other than the title itself) as the title section of the preliminary risk report 280. The report section 322 includes a table listing the selected receptor, pathway and COPC, the toxicity name, the toxicity description and the toxicity value. The report displays the receptor- and pathway-specific toxicity values for each COPC according to the selection of the toxicity factors section 242 in the risk assessment webpage 230. The view Excel report button 290 will preferably display the information in the report section 322 in a Microsoft Excel® spreadsheet format that can be downloaded. The return to webHRAS button 292 will preferably go back to the risk assessment webpage 230.

With reference now to FIG. 14a, if a HBRG output is selected in section 248 on the risk assessment webpage 230, as shown, then selection of the continue button on the receptor parameter webpage 260 (see FIG. 13b) will cause the risk assessment module 26 to perform a risk assessment that generates a preliminary HBRG report.

With reference to FIG. 14b, shown is a screen illustrating an exemplary preliminary HBRG report 350 that has a similar layout as the preliminary HQ/ILCR report 280 in FIG. 13d except all COPC concentrations 3522 are set to unity (mg/kg). The preliminary HBRG report 350 includes a title section 282 and a report section 352 and a page indication/selection section. The title section 282 lists the information describing the preliminary HBRG report 350. The report section 352 lists the receptor, the pathway, the COPC 3520, the COPC concentration (determined from the environmental data for the site or ROI) 3522, the HQ (non-cancer risk) calculation 3524 and the ILCR (cancer risk) calculation 3526. The report section 352 may include multiple pages. Accordingly, the preliminary risk report 280 may also include a section that indicates the page number of the report section 352 and the total number of pages and that enables navigation (e.g., one or more page navigation buttons (e.g., next page, previous page, last page, first page, etc.)) to the other pages of the risk calculation section 284.

The preliminary HBRG report 350 also includes a get summary report button 286, a view toxicity values button 288, a view Excel report button 290, a return to webHRAS button 292, and a map of the region of interest 294 as defined in the 3D viewer module 24. The get summary report button 286 opens up an HBRG summary report 360, as shown in FIG. 14c. The view toxicity values button 288 opens up an toxicity value used report, which preferably includes the same sections and the same type of information shown in the toxicity report shown in FIG. 13g. The toxicity value used report displays the receptor- and pathway-specific toxicity values for each COPC based on the selection of the toxicity factors section in the risk assessment webpage 230. The view Excel report button 290 displays the information in the report section 352 of the preliminary HBRG report 350 in a Microsoft Excel® spreadsheet format that can be downloaded. The return to webHRAS button 292 causes a return to the risk assessment webpage 230.

With reference now to FIG. 14c, shown is a screen illustrating a portion of a first page of the exemplary summary HBRG report 360 generated by the risk assessment module 26 based on selections made on the risk assessment webpage 230. The HBRG summary report 360 summarizes results of non-carcinogenic (HQ-based) 3626 and carcinogenic (ILCR-based) 3628 HBRG calculations. The summary HBRG report includes a title section 282, a report table section 362, a return to preliminary report button 304, a view final HBRG report 364, a view transaction log button 306, a view Excel report button 290, a return to webHRAS button 292 and a map of the region of interest 294 as defined in the 3D viewer module 24.

The title section 282 includes the same information (other than the title itself) as the title section of the preliminary HBRG report 350. The non-carcinogenic HBRGs calculated for each COPC, each receptor, and exposure pathway identified are calculated and summarized in the HQ-based HRBG section 3626 of summary HBRG report 360. The summary HBRG report table 362 presents the receptors 3620, exposure pathways 3622, and COPCs 3624 selected. The summary HBRG report table 362 also presents the chemical-, receptor- and pathway-specific non-carcinogenic (HQ-based) HBRG 3630 calculated based on the user-identified site conditions (set on the risk assessment webpage 230 and described in title section 282). Lastly, the lowest of pathway-specific non-carcinogenic HBRGs is selected and labeled as the HBRG for all pathways 3632. The carcinogenic (ILCR-based) HBRGs calculated for each COPC, each receptor, and exposure pathway identified are calculated in the same manner and summarized in the ILCR-based HRBG section 3628 of summary HBRG report 360.

The return to preliminary report button 304 in FIG. 14c is selected to take the user back to the initial preliminary HBRG report 350. The selection of the view final HBRG report button 364 triggers the creation and display of a final HBRG report 370 as shown in FIG. 14d. The view transaction log button 306 is selected to view a transaction log of all the input parameters and calculations that took place behind the scenes to arrive at the final Risk or HBRG calculation. The view Excel report button 290 displays the information in the table section 362 of the HBRG summary report 360 in a Microsoft Excel® spreadsheet format that can be downloaded. The return to webHRAS button 292 causes a return to the risk assessment webpage 230.

With reference now to FIG. 14d, if the view final HBRG report button 364 is selected, a final HBRG report 370 is generated and displayed by the risk assessment module 26. The most conservative (i.e., the lower) of the calculated HQ-based and ILCR-based HBRG for each COPC shown in the summary HBRG report 360 is compared and presented as initial HBRG 3724 in the final HBRG report 370. The final HBRG report 370 includes a title section 282, final report table section 372, a return to summary button 374, a view Excel report button 290, a return to webHRAS button 292 and a map of the region of interest 294 as defined in the 3D viewer module 24.

The title section 282 includes a descriptive title of the final HBRG report, including the site name and job name and is the same as that of the title section of the preliminary HBRG report 350. The final report table section 372 includes a table listing the selected receptor(s) 3720, the selected COPCs 3722, that selected COPCs initial HBRG calculation 3724, soil saturation 3726 and a final HBRG calculation 3728 which is the most conservative (the lower value of 3724 and 3726) calculated value. The final HBRG value 3728 represents the COPC-specific goal that needs to be achieved through remediation efforts in order to consider the subject COPC poses no acceptable risk to human health. The return to summary button 374 is selected to return to the HBRG summary report 360. The view Excel report button 290 displays the information in the report table section 372 of the final HBRG report 370 in a Microsoft Excel® spreadsheet format that can be downloaded. The return to webHRAS button 292 causes a return to the risk assessment webpage 230.

The above described summary risk report 300 and final HBRGs report 370 are preferably calculated in real-time, on the web, within minutes. The embodiments described herein allow the user to compare the cumulative HQ 3028, cumulative ILCR 3032, and final HBRGs 3728 to regulatory standards and identify the species and location of COPC(s) that exceed the standard. This allows the project team to design a remedial system to reduce the COPC concentration accordingly in the environment so that the subject COPC will no longer pose unacceptable risk to the receptor and the site therefore, can be closed.

As described above, FIGS. 15a–b are flowcharts illustrating an exemplary risk assessment method 380. The risk assessment method 380 illustrates steps performed by the risk assessment module 26 as illustrated in FIGS. 14a–14e. The risk assessment button 866 or the export to RA button 2220 is selected (block 381). The selection of the risk assessment button 866 triggers the risk assessment module 26 to display the risk assessment webpage 250. The risk assessment module 26 may receive a site, job and/or ROI selection (block 382), e.g., using sections 252–236 on the risk assessment webpage 250. The risk assessment module 26 receives a media type selection (block 383). The risk assessment module 26 determines if COPC(s) for the risk assessment are manually or automatically selected (block 384). If manually selected, the risk assessment displays a list of available COPCs (block 385) and receives a manual selection of the COPCs (block 386). If automatically selected, the risk assessment module 26 receives the automatic selection parameters (e.g., all COPCs, COPCs greater than industry goals, COPCs greater than maximum federal standards, etc.) (block 387).

A state or federal toxicity factor selection is received (block 388). If a state toxicity standard, the selection also includes the selection of the specific state. The risk assessment module 26 receives a selection of one or more receptors (block 389) and one or more pathways (block 390). These two steps develop a conceptual exposure model, identifying the receptors and their pathways that will lead to exposure to the COPCs. A threshold selection is received (block 391). The threshold selection may include a HQ and a ILCR threshold selection. The risk assessment module 26 determines whether HBRGs or risk selection is received (block 392). A risk selection may also include the selection of an environmental data statistical treatment, such as a 95% upper confidence limit.

With continued reference to FIG. 15a, if a risk selection is received, the risk assessment module 26 performs a risk assessment, producing risk assessment reports. The risk assessment module 26 retrieves and may display default receptor parameters for the selected receptors (block 393). The receptor parameters are used to perform the risk assessment for the selected receptor(s). A user may change the receptor parameters for the current risk assessment. The risk assessment module 26 receives and saves any changes to the receptor parameters (block 394).

The risk assessment module 26 retrieves site, job, ROI, media, and selected COPC data based on the received selections (block 395). The retrieved data includes, for example, site location information (e.g., name, address, cite, state, country, etc.), site characteristics (e.g., wind speed and direction, equivalent threshold wind speed, vegetative cover fraction, receptor exposure intervals, etc.), geo-hydrologic characteristics (e.g., soil porosity, soil density, soil temperature, water filled porosity, dry bulk density, etc.), ROI characteristics (e.g., size, COPCs present, geo-hydrologic characteristics, etc.), and COPC concentrations. If the COPCs are automatically selected, the risk assessment module 26 may utilize the site analysis function 12 to determine which COPCs in the site (or ROI) meet the automatic selection parameters.

After retrieving the data, the risk assessment module 26 performs the risk assessment (block 396), per the selected toxicity factors, receptor(s), pathway(s), and environmental data statistical treatment. The risk assessment module 26 may generate and display a preliminary report (block 397), e.g., preliminary risk report 280. The risk assessment module 26 may also generate and display a summary report (block 398), e.g., summary risk report 300. The risk assessment module 26 may also generate and display a spreadsheet version of the preliminary report and/or summary report. As described above, the risk assessment module 26 also keeps a transaction log and may generate and display transaction log. Likewise, the risk assessment module 26 may generate and display a toxicity values used report. The risk assessment module 26 may also download any of these reports as a file. Likewise, the risk assessment module 26 may also map the risk assessment results on the GIS map 72 of the site, illustrating the levels of risk on the site or ROI.

If a HBRGs selection is received, the risk assessment module 26 performs HBRGs calculations, producing HBRGs reports. The risk assessment module 26 may retrieve, display and change receptor parameters (e.g., blocks 393–394). With reference now to FIG. 15*b*, the risk assessment module 26 retrieves site, job, ROI, media, and selected COPC data based on the received selections (block 399). After retrieving the data, the risk assessment module 26 performs the HBRGs calculations (block 400), per the selected toxicity factors, receptor(s), pathway(s), and health risk thresholds. The risk assessment module 26 may generate and display a preliminary report (block 401), e.g., preliminary HBRG report 350. The risk assessment module 26 may generate a summary report (block 402), e.g., summary HBRG report 360. Likewise, the risk assessment module 26 may generate a final report (block 403), e.g., final HBRG report 370.

As with the risk assessment, the risk assessment module 26 may also generate and display a spreadsheet version of the preliminary, summary, and final HBRG reports. Likewise, the risk assessment module 26 may generate and display transaction log and a toxicity values used report. The risk assessment module 26 may also download any of these reports as a file. The risk assessment module 26 may also map the HBRG results on the GIS map 72 of the site, illustrating, e.g., where the COPC concentrations exceed the HBRGs and where the areas affected by COPC exceed HBRGs. The risk assessment module 26 may communicate the HBRGs results to the remediation module 28 for the remediation calculations.

With reference now to FIG. 16*a*, shown is a screen illustrating an exemplary remediation webpage 410. The remediation webpage 410 is used to initiate the above-described remediation technology screening process performed by the remediation module 28. The remediation webpage 410 is displayed by the remediation module 28 in response to the selection of the remedial technology button 868 on the central webpage 70 or with selecting the export to RT button 2222 on the 3D display webpage 210. The remediation webpage 410 includes the following sections: region of interest selection 412, score limit selection 414, report type 416 and transaction report 418. The region of interest (ROI) selection section includes a region of interest (ROI) pull down menu 4120 to select a particular region of interest that has already been defined and display its corresponding information 4122.

The ROI pull-down menu 4120 includes a list of ROIs that have been defined for the site. The user selects a ROI and the remediation screening process is performed based on the environmental data (e.g., COPCs, PRGs, contaminant mass, volume, and/or area, etc.) contained in the selected ROI and the feasibility study criteria developed by the US EPA. Alternatively, the remediation screening process may be performed on a sitewide-basis. The score limit selection 414 includes a score limit pull down 4140. The score limit pull-down menu 4140 enables the user to require that the reports only display remediation technologies with scores greater than or equal to a selected score limit (e.g., with 2.0 the most applicable technology and 0.0 the least applicable). Accordingly, the score limit pull-down menu 4140 includes a listing of score limits from lowest to highest (e.g., 0.0 to 2.0). The report selection section 416 includes an initial screening button 4160, a comprehensive screening button 4162 and a cost calculator button 4164. The transaction report section 418 includes a transaction report button 4180 that will initiate the creation of the transaction report.

If the initial screening button 4160 is selected, an initial screening report 420 (e.g., as shown in FIG. 16*b*) is generated and displayed by the remedial technology screening module 281. The initial screening report 420 has a heading 422 that includes site data and information generated in previous steps such as the selected ROI, media type, contaminant type, a unique identification number for each plume (plume ID), date/time, and a table with applicable remedial technology or technologies 424, each technologies score (ranking) 426, and required site specific data/information in order to run the comprehensive remedial technology screening 428. The remediation module 28 screens each remedial technology by applying the site data and the information gathered above to the known parameters of the technology, preferably using the remedial technology selection approach and algorithms from the US EPA's *Remediation Technologies Screening Matrix and Reference Guide, $4^{th}$ Edition*. Based on this screening, the remediation module 28 generates a score for the remedial technology indicating the technology's level of applicability for remediation. For example, a remedial technology with a high effectiveness in cleaning up benzene in silt will score higher for a ROI with benzene and silt than for a remedial technology with a low effectiveness for benzene in silt. The baseline rankings may be set based on industry standards and/or user preferences. The initial screening report 420 shown in FIG. 16*b* is a .pdf document that may be downloaded.

If the comprehensive screening button 4162 is selected, a comprehensive screening report 430 (e.g., as shown in FIG. 16c) is generated and displayed by the remediation module 28. The comprehensive screening report 430 has a heading 432 that includes the selected ROI, media type, contaminant type, plume ID, date/time, and a table with applicable remedial technology or technologies 434, ranking 436, technology limitations (if any) 438, and a estimate of time for remediation for each remedial technology 440. The comprehensive screening report 430 is generated using the user-defined site specific conditions, preferably obtained from the environmental data in the central database 30, again preferably using the remedial technology selection approach and algorithms from the US EPA's *Remediation Technologies Screening Matrix and Reference Guide*, $4^{th}$ *Edition*. Specifically, the estimate of time (e.g., a rough order of magnitude estimate of time in years) is calculated based on input parameters 428, other site data, and known parameters for each remedial technology. The comprehensive screening report 430 lists the applicable technologies in order of preference. The comprehensive screening report 430 is more final in terms of remedial technology selection than the initial screening report as it uses site specific parameter inputs and reaches final conclusion with respect to the applicability (see columns 438, 440) of a specific remedial technology 442 to the defined plume 432. The comprehensive screening report 430 shown in FIG. 16c is also a .pdf document that may be downloaded.

If the cost calculator button 4164 is selected, a cost calculator 450 (e.g., as shown in FIG. 16d) is generated and displayed by the remediation module 28. The cost calculator 450 is a tool for calculating a cost estimate for any applicable remedial technology listed in the comprehensive screening report 430. The cost calculator 450 shown lists everything included in the comprehensive screening report 430 and the impact area and volume (i.e., the area and volume of the COPC(s) in the ROI) 452. The cost calculator 450 also includes a time estimate column 454, a unit price column 456, a unit column 458 and a cost estimate column 460. The time estimate column 454 displays the rough order of magnitude of time it will take the associated remedial technology to complete the removal of contaminants at the site. The unit price column 456 includes a unit-price text box for each applicable remedial technology, allowing the user to enter a unit-price for each applicable remedial technology. Alternatively, the unit price column 456 may display unit prices from a database, or other commercial or government sources, of unit prices for remedial technologies. The unit column 458 includes a unit-type pull-down menu for each applicable remedial technology. The unit-type pull-down menu allows the user to select the unit type (e.g., $m^3$, $m^2$, $ft^3$, $ft^2$, etc.) corresponding to the unit price. The unit type selection also determines what computation (e.g., volume, area, mass, etc.) from the 3D display is used for calculating the cost estimate. The cost estimate column 460 includes the cost estimate for each applicable remedial technology that the user causes to be calculated. The cost estimate column calculates the estimated cost for each applicable remedial technology based on the estimate time 454, the unit price entered 456 and the unit type 458.

The transaction report button 4180 on the remediation webpage 410 generates a transaction report 470 as shown in FIG. 16e. The transaction report 470 includes a header section 472 and a reports section 474. The header section 472 contains information about the selected ROI from the region of interest pull down menu 4120. The reports section 474 contains links to the transaction logs to both the initial screening and comprehensive screening reports. The transaction logs detail each process utilized by the remedial technology screening module 281 to arrive to the final technology screening. A screenshot of an exemplary transaction log 480 is shown in FIG. 16f.

FIG. 17 is a flowchart illustrating an exemplary remediation method 490. The method 490 illustrates steps performed by the remediation module 28 as illustrated in FIGS. 16a–16f. The method 490 preferably begins upon selection of the remedial technology button 868 or the export data to RA button 2222, which preferably causes the remediation module 28 to generate the remediation webpage 410. The method 490 may include objectives such selecting all applicable remedial technologies, determining a subset of applicable technologies as feasible remedial technologies, performing a final evaluation of the feasible technologies, performing a cost estimation for applying the final feasible technologies and enable the selection of the desired remedial technology to be used.

To achieve these objectives, the remediation module 28 receives a selection of a ROI (block 491) for the current site. A score limit, limiting the selection of remedial technologies to technologies scoring above the score limit, may be set (block 492) based on a user selection. The remediation module 28 retrieves site data (e.g., site condition, contaminant types, and impacted media) (block 493). The site data may be retrieved from the central database 30. Based on the retrieved site data relevant to the selected ROI, the remediation module 28 generates and displays an initial screening report (block 494), e.g., initial screening report 420. The remediation module 28 may retrieve the applicable remedial technologies from the central database 30. The initial screening report includes applicable remedial technologies, limited by the score limit, if a score limit is set. The remediation module 28 may score each remedial technology based on known parameters of the technology, site data, industry standards, etc.

With continued reference to FIG. 17, the remediation module 28 generates and displays a comprehensive screening report (block 495), e.g., comprehensive screening report 430. Generating the comprehensive screening report may include retrieving and/or receiving additional, more detailed site data (e.g., contaminant concentrations, geo-hydrological properties, the presence or absence of non-aqueous phase liquid (NAPL), etc.), and further information regarding the applicable remedial technologies, to perform the more comprehensive screening. Generating the comprehensive screening report may also include estimating the time to remediate for each remedial technology based on the site data and known parameters of the remedial technologies. The remediation module 28 generates and displays a cost calculator (block 496), e.g., cost calculator 450, that includes the remedial technologies in the comprehensive screening report. The cost calculator 450 enables the user to select on which remedial technologies to perform a cost estimation (block 497). Based on the results of the cost estimation, the user may select the desired remedial technology (block 498).

As noted above, the method 490 may also include generating and displaying transaction logs (e.g., see FIGS. 16e–d). Further, the reports generated and displayed above may also be downloaded as files. Additionally, the remediation module 28 may graph cost estimates over time, using the magnitude of time and cost estimates shown in the comprehensive screening report.

Embodiments of the system 5 can also include 3D visualization of above-ground structures such as buildings, above-ground site conditions such as air dispersion modeling, and risk assessments specifically targeted for ecology and radiology. A tracking module may be incorporated into the system 5 to track manifest shipments of contaminated media removed from the site to record the remediation progress at the project site. Other additions to the system 5 may include plotting or printing precision engineering drawings for site cleanup process; automatic email and/or cell phone alerts to responsible parties when monitoring levels have reached a predetermined level and a builtin project management system with graphical illustration of the project schedule to plan, coordinate, and track progress of specific tasks in the cleanup process.

Another alternative embodiment of the system 5 is a homeland security embodiment. The homeland security embodiment utilizes the real-time, online and web-based aspects of the system 5 and the EDMS application to monitor sensor readings of radiological, chemical, biological and explosive ingredients in the environment; warn and report about detected weapons of mass destruction (WMD) threats and manage responses thereto. For example, instead of a hazardous waste site, the homeland security site monitored by the webEDMS may be a subway, a government building, a sporting arena, an intersection, a city block, etc. Instead of monitoring wells, the homeland security site may have sensors detecting chemical, radiological, biological or explosive agents. The central database 30 preferably includes baseline environmental data (e.g., toxicity of an agent, safe explosive levels, alarm trigger concentrations, etc) for the homeland security site. The sensors provide live updates to the system 5 that are processed by the EDMS application and stored in the central database 30. Storing the live updates in the central database 30 enables real time displays of measured concentrations across a large area or user-defined ROI in GIS maps as well as trend analysis and pattern studies. The EDMS application may include regulatory standards for safe levels of possible chemical, radiological, biological or explosive agents of concern (AOCs). The EDMS application monitors the live updates from the sensors (e.g., using the continuous monitoring system 170) and continuously compares the live updates to the regulatory standards (e.g., using the analysis module 8). If the live updates exceed or get within a certain percentage of the regulatory standard, the EDMS application determines the location of the associated sensor(s), generates a warning (e.g., email, text messages via cell phones, etc) and a report, and displays the sensor(s) location in the GIS. A user may access a 3D display of the AOC contamination, conduct a risk assessment and run response and remediation scenarios to determine emergency response and cleanup possibilities, respectively. The same embodiment may be used to study what-if scenarios and conduct strategic planning by loading in user-selected hypothetical data and sensor readings.

As noted above, the embodiments described herein are applicable to chemicals as well as other contaminants. Throughout the above description, the term "chemical" is often used alone. It is apparent from the description herein that "chemical" is interchangeable with other types of contaminants (e.g., chemical, radiological, biological, explosive, or AOCs). The functions, analyses, calculations, monitoring, displays, etc. described above as being performed with chemicals may also be performed with other types of contaminants as well.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

The invention claimed is:

1. A system for environmental data management, comprising:
   an application including:
   a mapping module that generates an interactive graphical mapping interface of the site, the interactive mapping interface including links to environmental data from a site and related documents;
   an analysis module that analyzes the environmental data, the environmental data including contaminants of potential concern (COPC) data;
   a risk assessment module that assesses the human health risks caused by COPCs at the site; and,
   a remediation module that screens remedial technology for cleaning up COPCs.

2. The system of claim 1 wherein the application further includes:
   a three-dimensional (3D) viewer module that generates a 3D display of the site and the environmental data.

3. The system of claim 2 wherein the 3D viewer module enables a user to define a 3D region of interest (ROI) on the 3D display.

4. The system of claim 3 wherein the risk assessment module assesses the human health risks caused by COPCs in the ROI.

5. The system of claim 3 wherein the remediation module remedial technology for cleaning up COPCs in the ROI.

6. The system of claim 2 wherein the 3D viewer modules enables a user to define a sampling period on the 3D display.

7. The system of claim 2 wherein the interactive mapping interface includes a link to the 3D viewer module.

8. The system of claim 1 further comprising a central database that stores the environmental data from the site, wherein the application retrieves the environmental data from the central database.

9. The system of claim 8 further comprising a plurality of site monitoring systems that monitor COPC readings on the site, wherein the site monitoring systems periodically communicate COPC readings to the application for storage in the central database.

10. The system of claim 9 wherein the site monitoring systems include one or more of the following: emission monitoring stations, monitoring wells, soil borings, soil vapor collection points, air dike probes, piezometer wells, and vapor extraction wells.

11. The system of claim 9 further comprising a continuous monitoring system module that provides a user interface to the site monitoring systems and real-time COPC readings from the site monitoring systems.

12. The system of claim 11 wherein the interactive mapping interface includes a link to the continuous monitoring system module.

13. The system of claim 1 wherein the analysis module comprises:
   an object analysis module that analyzes environmental data for objects of the site, wherein an object represents a physical location on the site for which environmental data is measured and stored.

14. The system of claim 13 wherein the object analysis module compares COPC concentration data for an object to a standard.

15. The system of claim 14 wherein the object analysis module compares COPC concentration data for an object to the standard over a period of time.

16. The system of claim 14 wherein the standard is a regulatory standard.

17. The system of claim 14 wherein the standard is a user-defined standard.

18. The system of claim 1 wherein the analysis module includes:
a site analysis module that analyzes environmental data on a site-wide basis.

19. The system of claim 18 wherein the site analysis module compares COPC concentration data for the entire site to a standard.

20. The system of claim 18 wherein the site analysis module compares COPC concentration data for a plurality of objects to a standard, wherein an object represents a physical location on the site for which environmental data is measured and stored.

21. The system of claim 1 wherein the environmental data includes historic data and current data.

22. The system of claim 1 wherein the risk assessment module generates a risk output that includes non-carcinogenic risks and incremental lifetime cancer risks.

23. The system of claim 22 wherein the risk assessment module maps the risk output on the GIS map of the site, illustrating the levels of health risk on the site or ROI.

24. The system of claim 1 wherein the risk assessment module calculates health based remedial goals (HBRGs) for the site.

25. The system of claim 24 wherein the HBRGs include remedial goals for maximum threshold levels of allowable remaining non-carcinogenic risks and remaining incremental lifetime cancer risks.

26. The system of claim 24 wherein the risk assessment module maps the HBRGs on the GIS map of the site, illustrating where COPC concentrations exceed the HBRGs on the site or ROI.

27. The system of claim 1 wherein the risk assessment module assesses human health risks based on the environmental data using one or more algorithims recited in a publication chosen from a list consisting of: US EPA's Superfund Exposure Assessment Manual, US EPA's Guidance for Conducting Remedial Investigations and Feasibility Studies Under CERCLA, US EPA's Human Health Evaluation Manual (Part A) Volume I in Risk Assessment Guidance for Superfind, and US EPA's Environmental Evaluation Manual Volume II in Risk Assessment Guidance for Superfund.

28. The system of claim 1 wherein the remediation module screens remedial technologies by ranking an applicability score for each remedial technology.

29. The system of claim 1 wherein the remediation module screens remedial technologies by estimating a clean-up time for each remedial technology.

30. The system of claim 1 wherein the remediation module screens remedial technologies by calculating a cost for each remedial technology.

31. The system of claim 1 wherein the remediation module screens remedial technologies using algorithms from US EPA's *Remediation Technologies Screening Matrix and Reference Guide, 4th Edition.*

32. The system of claim 1 wherein the interactive mapping interface includes links to the analysis module, the risk assessment module, and the remediation module.

33. The system of claim 1 wherein the application further includes a file management module that provides access, management and organization of site data, reports and files and wherein the interactive mapping interface includes a link to the file management module.

34. The system of claim 1 wherein the application further includes a project management module that enables viewing, managing, setting and determining project resources, schedules and deadlines for planning clean-up projects at the site and wherein the interactive mapping interface includes a link to the project management module.

35. The system of claim 1 wherein the application further includes a collaboration module that provides a centralized online area for project team members to share non-project related files, discuss topics, exchange information, and conduct online meetings and wherein the interactive mapping interface includes a link to the collaboration module.

36. The system of claim 1 wherein the application further includes a calendar module that provides a calendar for scheduling projects and other appointments and wherein the interactive mapping interface includes a link to the calendar module.

37. The system of claim 1 wherein the application is a web-based application.

38. The system of claim 1 further comprising an application server that includes:
a memory, wherein the application is stored in the memory; and
a processor, connected to the memory, that runs the application.

39. The system of claim 38 wherein the application server is connected to a network, the system further comprising a plurality of user machines, connected to the network, that provide access to the application run on the application server.

40. The system of claim 39 wherein the network is the Internet.

41. The system of claim 1 wherein the COPCs include one or more contaminants from a list consisting of: chemical, biological, radiological, and explosive contaminants.

42. A system for providing homeland security comprising:
a mapping module that generates an interactive graphical mapping interface of the site, the interactive mapping interface including links to environmental data, the environmental data including contaminants of potential concern (COPC) data;
a plurality of site monitoring systems that monitor COPC readings on the site, wherein the site monitoring systems provide real-time COPC readings; and
a continuous monitoring system module that provides a user interface to the site monitoring systems and the real-time COPC readings from the site monitoring systems.

43. The system of claim 42 wherein the continuous monitoring system provides an alert if the real-time COPC readings exceed a certain level.

44. The system of claim 43 wherein the alert is chosen from a list consisting of:
an email, a text message, an instant message (IM), and a telephone call.

45. The system of claim 43 further comprising an analysis module that analyzes environmental data from the site and determines whether the real-time COPC readings exceed the certain level.

46. The system of claim 42 wherein the continuous monitoring system module generates a contour plot of real-time COPC readings on the site.

47. The system of claim 42 further comprising a three-dimensional (3D) viewer module that generates a 3D display of the site and the real-time COPC readings.

48. The system of claim 42 wherein the COPC data includes data about chemical, biological, radiological and explosive agents from the site.

49. A method for environmental data management, comprising:

analyzing contaminants of potential concern (COPC) data for an object of a site, wherein the object represents a physical location on the site for which COPC data is measured and stored;

generating a three-dimensional (3D) display of the site, wherein the 3D display illustrates concentrations of COPCs at the site;

receiving a selection of a region-of-interest (ROI) in the 3D display;

assessing health risks from COPCs in the ROI; and screening remedial technologies for cleaning up the COPCs in the ROI.

50. The method of claim 49 further comprising receiving a selection of a sampling period in the 3D display.

51. The method of claim 49 further comprising analyzing COPC data for the entire site.

52. The method of claim 50 wherein the analyzing COPC data for objects step includes:

receiving an object selection;

retrieving COPC concentration readings for the selected object;

receiving a screening query selection;

receiving an analyte selection, wherein the analyte is one of the COPCs for the selected object; and analyzing the concentration readings for the selected analyte based on the selected screening query.

53. The method of claim 52 wherein the selected screening query is a standard, and the analyzing the concentration readings step compares the concentration readings for the selected analyte to the standard.

54. The method of claim 53 wherein the standard is a regulatory standard.

55. The method of claim 53 wherein the standard is a user-defined standard.

56. The method of claim 52 wherein the analyzing COPC data for objects step further includes displaying an object analyze webpage.

57. The method of claim 52 wherein the analyzing COPC data for objects step further includes receiving temporal limits, wherein the contaminant readings retrieved are limited by the temporal limits.

58. The method of claim 52 wherein the analyzing COPC data for objects step further includes receiving a sample matrix selection, wherein the contaminant readings are retrieved only for the sample matrix.

59. The method of claim 52 wherein the analyzing COPC data for objects step further includes displaying the results of the analyzing the concentration readings step.

60. The method of claim 49 further comprising generating an interactive graphical mapping interface of the site, the interactive mapping interface including links to the environmental data.

61. The method of claim 51 wherein the analyzing COPC data for the entire site step includes:

retrieving COPC concentration readings for the entire site;

receiving a screening query selection;

receiving an analyte selection, wherein the analyte is one of the COPCs for the entire site; and analyzing the concentration readings for the selected analyte based on the selected screening query.

62. The method of claim 61 wherein the selected screening query is a standard, and the analyzing the concentration readings step compares the concentration readings for the selected analyte to the standard.

63. The method of claim 61 wherein the analyzing COPC data for the entire site step further includes receiving temporal limits, wherein the contaminant readings retrieved are limited by the temporal limits.

64. The method of claim 61 wherein the analyzing COPC data for the entire site step further includes receiving a sample matrix selection, wherein the contaminant readings are retrieved only for the sample matrix.

65. The method of claim 61 wherein the analyzing COPC data for the entire site step further includes displaying the results of the analyzing the concentration readings step.

66. The method of claim 65 wherein the analyzing COPC data for the entire site step further includes receiving an analyte number limit selection, wherein the displaying step limits the results displayed by the analyte number limit selected.

67. The method of claim 65 wherein the displaying step displays the results on an interactive mapping interface.

68. The method of claim 49 wherein the assessing health risks step includes receiving a ROI selection;

receiving a media type selection;

receiving a selection of COPCs for which risk is assessed;

receiving a toxicity factor selection;

receiving a selection of one or more receptors and one or more exposure pathways for the risk assessment;

receiving a threshold selection; and determining whether a risk output or health-based-remedial-goal (HBRG) output is selected.

69. The method of claim 68 wherein the assessing health risks step further includes:

retrieving ROI, media, and selected COPC data based on the received selections;

performing a risk output assessment per the retrieved data and the selected toxicity factors, receptor(s), pathway(s), and threshold;

generating a risk report based on the risk output assessment, wherein the risk report details carcinogenic and non-carcinogenic risks from the selected COPCs in the ROI.

70. The method of claim 68 wherein the assessing health risks step further includes:

retrieving ROI, media, and selected COPC data based on the received selections;

performing a HBRG output assessment per the retrieved data and the selected toxicity factors, receptor(s), pathway(s), and threshold;

generating a HBRG report based on the HBRG output assessment, wherein the HBRG report includes HBRGs for the selected COPCs in the ROI.

71. The method of claim 68 wherein the receiving a selection of COPCs step includes:

determining if COPC(s) for the risk assessment are manually or automatically selected (block 384);

if manually selected, receiving a manual selection of the COPCs; and if automatically selected, receiving automatic selection parameters and selecting the COPCs based on the automatic selection parameters.

72. The method of claim 68 wherein the receiving toxicity factors step includes receiving a federal or state toxicity factor selection.

73. The method of claim 68 wherein the receiving a target threshold selection includes receiving hazard quotient (HQ) and incremental-lifetime cancer risk (ILCR) threshold selections.

74. The method of claim 68 wherein the assessing health risks step further includes receiving and saving changes to receptor parameters.

75. The method of claim 49 wherein the screening remedial technologies step includes:
    receiving a selection of a ROI;
    receiving a selection of a score limit;
    retrieving environmental data, including COPC data, for the selected ROI;
    scoring applicable remedial technologies based on the retrieved environmental data; and
    generating an initial screening report that lists the applicable remedial technologies that are scored at or above the score limit.

76. The method of claim 75 wherein the screening remedial technologies step further includes:
    estimating a clean-up time for each applicable remedial technology in the screening report; and
    generating a comprehensive screening report that lists the applicable remedial technologies and the estimated clean-up time for each.

77. The method of claim 75 wherein the screening remedial technologies step further includes:
    generating and displaying a cost calculator for calculating the costs of cleaning up the COPCs in the ROI with the applicable remedial technologies;
    performing a cost calculation on selected applicable remedial technologies; and
    selecting one of the applicable remedial technologies.

78. A computer-readable medium comprising instructions for performing the method of claim 49.

79. A computer-readable medium comprising instructions for performing the method of claim 51.

80. A computer-readable medium comprising instructions for performing the method of claim 61.

81. A computer-readable medium comprising instructions for performing the method of claim 68.

82. A computer-readable medium comprising instructions for performing the method of claim 69.

83. A computer-readable medium comprising instructions for performing the method of claim 70.

84. A computer-readable medium comprising instructions for performing the method of claim 75.

85. A graphical user interface for environmental data management, comprising:
    an interactive geographic information system (GIS) map of the site, wherein the map includes links to objects displayed on the map, wherein an object represents a physical location on the site for which environmental data is measured and stored;
    a site data section that includes site data;
    an object data section that includes data about a selected object from the site; and
    a plurality of selectable buttons corresponding to modules, including:
    an analysis module that analyzes environmental data from a site, the environmental data including contaminants of potential concern (COPC) data;
    a three-dimensional (3D) viewer module that generates a 3D display of the site and the environmental data.
    a risk assessment module that assesses the human health risks caused by COPCs at the site; and,
    a remediation module that screens remedial technology for cleaning up COPCs.

* * * * *